US012561809B2

(12) United States Patent
Lee et al.

(10) Patent No.: US 12,561,809 B2
(45) Date of Patent: Feb. 24, 2026

(54) COMPUTERIZED TOMOGRAPHY IMAGE PROCESSING

(71) Applicant: Oxford University Innovation Limited, Oxford (GB)

(72) Inventors: Regent Lee, Oxford (GB); Anirudh Chandrashekar, Oxford (GB); Vicente Grau, Oxford (GB); Ashok Handa, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 635 days.

(21) Appl. No.: 17/637,279

(22) PCT Filed: Aug. 21, 2020

(86) PCT No.: PCT/GB2020/052013
§ 371 (c)(1),
(2) Date: Feb. 22, 2022

(87) PCT Pub. No.: WO2021/038202
PCT Pub. Date: Mar. 4, 2021

(65) Prior Publication Data
US 2022/0284584 A1 Sep. 8, 2022

(30) Foreign Application Priority Data

Aug. 23, 2019 (GB) ...................................... 1912149
Feb. 10, 2020 (GB) ...................................... 2001791
(Continued)

(51) Int. Cl.
*G06T 7/11* (2017.01)
*A61B 6/50* (2024.01)
(Continued)

(52) U.S. Cl.
CPC ................ *G06T 7/11* (2017.01); *A61B 6/504* (2013.01); *G06T 3/40* (2013.01); *G06T 7/174* (2017.01);
(Continued)

(58) Field of Classification Search
CPC .......... A61B 6/504; G06T 2207/10081; G06T 2207/20021; G06T 2207/20081;
(Continued)

(56) References Cited

U.S. PATENT DOCUMENTS

| | | | | | |
|---|---|---|---|---|---|
| 10,163,040 | B2 * | 12/2018 | Poole | ........................ | G06T 7/68 |
| 2011/0064292 | A1 * | 3/2011 | Chen | ........................ | G06T 5/50 |
| | | | | | 382/131 |

(Continued)

FOREIGN PATENT DOCUMENTS

| | | |
|---|---|---|
| WO | 2017/059302 A1 | 4/2017 |
| WO | 2018/236905 A1 | 12/2018 |

OTHER PUBLICATIONS

Veit Sandfort et al., "Data augmentation using generative adversarial networks(CycleGAN) to improve generalizability in CT segmentation tasks," Nov. 15, 2019, Scientific Reports |(2019)9:16884,pp. 1-8.*

(Continued)

*Primary Examiner* — Omar S Ismail
(74) *Attorney, Agent, or Firm* — Thomas|Horstemeyer, LLP

(57) ABSTRACT

Methods for training an algorithm to identify structural anatomical features, for example of a blood vessel, in a non-contrast computed tomography (NCT) image are described herein. The algorithm may comprise an image segmentation algorithm, a random forest classifier, or a generative adversarial network in examples described (Continued)

500

Receive a plurality of non-contrast CT images. ~ 510

Receive a plurality of contrast CT images, each contrast CT image corresponding to an non-contrast CT image of the plurality of NCT images. ~ 520

Generate a mask for the targeted region of the non-contrast image using the extracted information from the contrast CT image. ~ 530

Segmenting the plurality of adapted CCT images to generate a corresponding plurality of segmentation masks. ~ 540

Establish a labelled training set, wherein the labelled training set includes pairs of NCT images and segmentation masks. ~ 550 herein. In one embodiment, a method comprises receiving a labelled training set for a machine learning image segmentation algorithm. The labelled training set comprising a plurality of NCT images, each NCT image of the plurality of NCT images showing a targeted region of a subject, the targeted region including at least one blood vessel. The labelled training set further comprises a corresponding plurality of segmentation masks, each segmentation mask labelling at least one structural feature of a blood vessel in a corresponding NCT image of the plurality of NCT images. The method further comprises training a machine learning image segmentation algorithm, using the plurality of NCT images and the corresponding plurality of segmentation masks, to learn features of the NCT images that correspond to structural features of the blood vessels labelled in the segmentation masks, and output a trained image segmentation model. The method further comprises outputting the trained image segmentation model usable for identifying structural features of a blood vessel in an NCT image. Further methods are described herein for identifying anatomical features from an NCT image, and for establishing training sets. Computing apparatuses and computer readable media are also described herein.

15 Claims, 36 Drawing Sheets

(30)          Foreign Application Priority Data

Feb. 10, 2020    (GB) ...................................... 2001792
Mar. 2, 2020     (GB) ...................................... 2002987

(51) Int. Cl.
| | |
|---|---|
| *G06T 3/40* | (2024.01) |
| *G06T 7/174* | (2017.01) |
| *G06T 7/30* | (2017.01) |
| *G06V 10/764* | (2022.01) |
| *G06V 10/774* | (2022.01) |
| *G06V 10/82* | (2022.01) |
| *G16H 30/40* | (2018.01) |

(52) U.S. Cl.
CPC .............. *G06T 7/30* (2017.01); *G06V 10/764* (2022.01); *G06V 10/774* (2022.01); *G06V 10/82* (2022.01); *G16H 30/40* (2018.01); *G06T 2207/10081* (2013.01); *G06T 2207/20021* (2013.01); *G06T 2207/20081* (2013.01); *G06T 2207/20084* (2013.01); *G06T 2207/30048* (2013.01); *G06T 2207/30084* (2013.01); *G06T 2207/30092* (2013.01); *G06T 2207/30101* (2013.01)

(58) Field of Classification Search
CPC . G06T 2207/20084; G06T 2207/30048; G06T 2207/30084; G06T 2207/30092; G06T 2207/30101; G06T 3/40; G06T 7/0012; G06T 7/11; G06T 7/174; G06T 7/30; G06V 10/764; G06V 10/774; G06V 10/82; G16H 30/40
See application file for complete search history.

(56)          References Cited

U.S. PATENT DOCUMENTS

| | | | |
|---|---|---|---|
| 2013/0294667 A1 | 11/2013 | Zheng et al. | |
| 2016/0328855 A1 | 11/2016 | Lay et al. | |
| 2018/0116723 A1* | 5/2018 | Hettrick | A61B 34/10 |
| 2018/0276853 A1* | 9/2018 | Carmi | A61B 6/481 |
| 2018/0374193 A1* | 12/2018 | Park | G06T 7/11 |
| 2018/0374194 A1* | 12/2018 | Park | G06F 18/2178 |
| 2019/0172207 A1* | 6/2019 | Odry | G06V 10/82 |
| 2019/0259153 A1* | 8/2019 | Zhang | G06V 10/82 |
| 2020/0074707 A1* | 3/2020 | Lee | G06V 30/274 |
| 2020/0134876 A1* | 4/2020 | Park | G06T 5/92 |
| 2020/0179539 A1* | 6/2020 | Lewis | A61K 49/0428 |
| 2021/0007690 A1* | 1/2021 | Bronkalla | G06N 3/09 |
| 2021/0090694 A1* | 3/2021 | Colley | G16B 30/00 |
| 2021/0150310 A1* | 5/2021 | Wu | G06T 7/30 |
| 2022/0284584 A1* | 9/2022 | Lee | G06V 10/82 |

OTHER PUBLICATIONS

Sila Kurugol, "Aorta Segmentation with a 3D Level Set Approach and Quantification of Aortic Calcifications in Non-contrast Chest CT," Nov. 10, 2012,2012 Annual International Conference of the IEEE Engineering in Medicine and Biology Society,pp. 2343-2345.*
Julia M. H. Noothouta, "Automatic Segmentation of Thoracic Aorta Segments in Low-Dose Chest CT," Mar. 2, 2018,Proceedings vol. 10574, Medical Imaging 2018: Image Processing; 105741S (2018),pp. 1-4.*
Litjens, Geert, et al. "State-of-the-art deep learning in cardiovascular image analysis." Aug. 12, 2019, JACC: Cardiovascular imaging 12.8 Part 1 (2019),pp. 1549-1565.*
Poirot, Maarten G., et al. "Physics-informed deep learning for dual-energy computed tomography image processing." Nov. 27, 2019 Scientific reports 9.1 (2019),pp. 1-7.*
McCollough, Cynthia H., et al. "Dual-and multi-energy CT: principles, technical approaches, and clinical applications. " Aug. 24, 2015, Radiology 276.3 (2015):, pp. 637-650.*
Bieth, Marie, et al. "Segmentation of skeleton and organs in whole-body CT images via iterative trilateration." Jun. 27, 2017,IEEE transactions on medical imaging 36.11 (2017),pp. 2276-2283.*
Yujia Zhou et al., "Correlation-Weighted Sparse Representation for Robust Liver DCE-MRI Decomposition Registration, "Mar. 20, 2019,IEEE Transactions on Medical Imaging, vol. 38, No. 10, Oct. 2019,pp. 2352-2362.*
Yuankai Huo et al.,"Splenomegaly Segmentation on Multi-Modal MRI Using Deep Convolutional Networks," Nov. 13, 2018, IEEE Transactions on Medical Imaging, vol. 38, No. 5, May 2019,pp. 1185-1193.*
International Search Report and Written Opinion for WO 2021/038202 (PCT/GB2020/052013), dated Feb. 1, 2021, pp. 1-20.
UK Search Report for GB 1912149.0, dated Feb. 20, 2020, pp. 1-10.
Jen-Tang Lu et al: "DeepAAA: clinically applicable and generalizable detection of abdominal aortic aneurysm using deep learning", arxiv .org, Cornell University Library, 201 Olin Library Cornell University Ithaca, NY 14853, Jul. 4, 2019 (Jul. 4, 2019).
Marie Bieth et al: "Segmentation of Skeleton and Organs in Whole-Body CT Images via Iterative Trilateration", IEEE Transactions on Medical Imaging, vol. 36, No. 11, Nov. 1, 2017 (Nov. 1, 2017), pp. 2276-2286.
Julia M H Noothout et al: "Automatic Segmentation of Thoracic Aorta Segments in Low-Dose Chest CT", arxiv.org, Cornell University Library, 201 Olin Library Cornell University Ithaca, NY 14853, Oct. 9, 2018 (Oct. 9, 2018).
S Kurugol et al, "Engineering in Medicine and Biology Society (EMBC), 2013 34th Annual International Conference of the IEEE EMBS", published 2012, IEEE, pp. 2343-2346, Kurugol et al, "Aorta segmentation with a 3D level set approach and quantification of aortic calcifications in non-contrast chest CT".
European Examination Report for Patent Application No. 20 764 732.2, dated Sep. 27, 2024, pp. 1-11.
Kim Wook et al: "Contrast CT image generation model using CT image of PET/CT", 2018 IEEE Nuclear Science Symposium and Medical Imaging Conference Proceedings (NSS/MIC), IEEE, Nov. 10, 2018 (Nov. 10, 2018), pp. 1-3.
Vey Brianna Let al: "The Role of Generative Adversarial Networks in Radiation Reduction and Artifact Correction in Medical Imag-

(56)           References Cited

OTHER PUBLICATIONS ing", Journal of the American College of Radiology, Elsevier, Amsterdam, NL, vol. 16, No. 9, Sep. 1, 2019 (Sep. 1, 2019), pp. 1273-1278.

Tang Chao et al: "Unpaired Low-Dose CT Denoising Network Based on Cycle-Consistent Generative Adversarial Network with Prior Image Information", Computational and Mathematical Methods in Medicine, vol. 2019, Dec. 7, 2019 (Dec. 7, 2019), pp. 1-11.

Yan Zuo et al: "Generative Adversarial Forests for Better Conditioned Adversarial Learning", arxiv.org, Cornell University Library, 201 Olin Library Cornell University Ithaca, NY 14853, May 14, 2018 (May 14, 2018).

Phillip Isola et al: "Image-to-Image Translation with Conditional Adversarial Networks", arxiv.org, Cornell University Library, 201 Olin Library Cornell University Ithaca, NY 14853, Nov. 21, 2016 (Nov. 21, 2016).

* cited by examiner

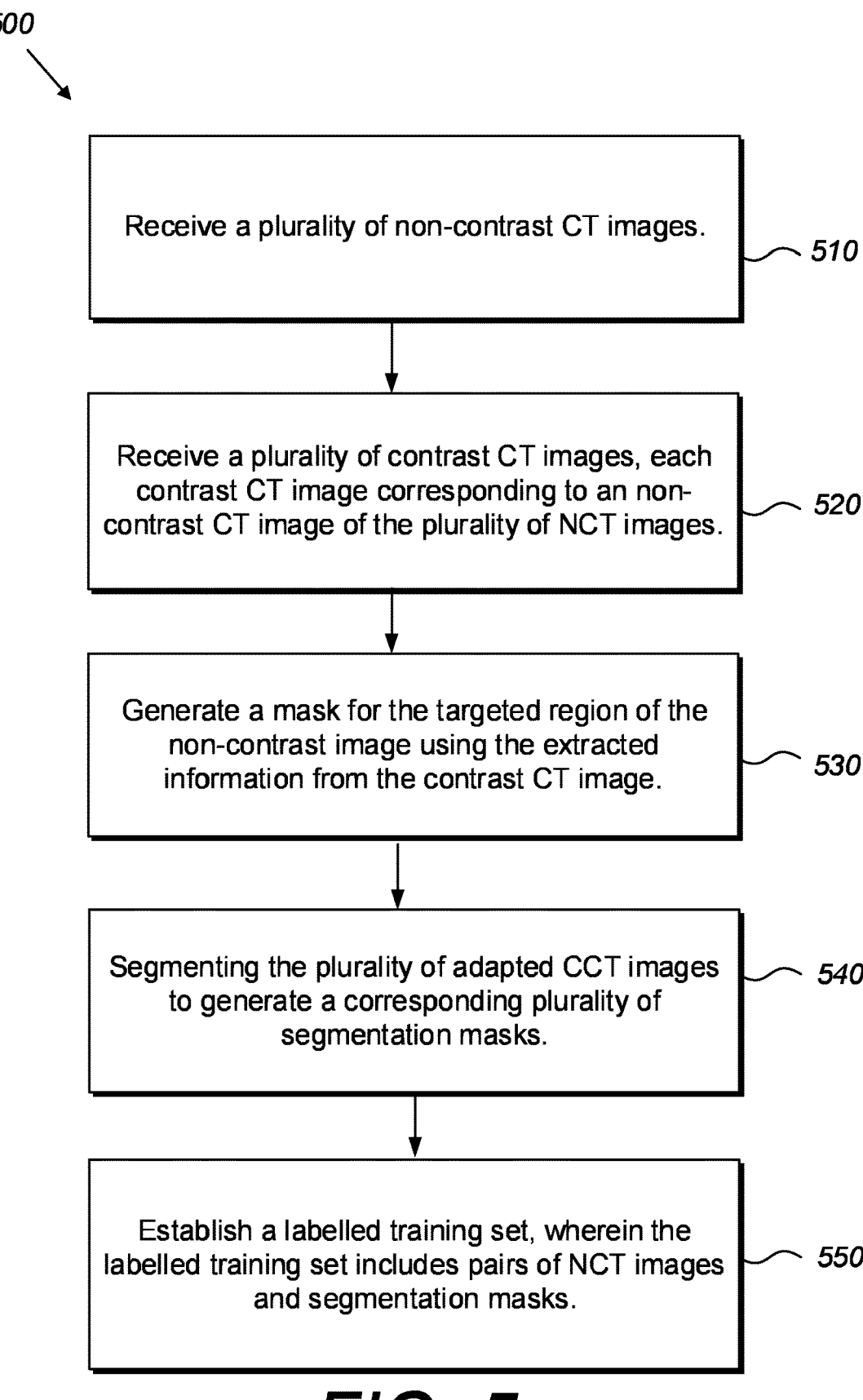

Receive a plurality of non-contrast CT images. ⟶ 510

Receive a plurality of contrast CT images, each contrast CT image corresponding to an non-contrast CT image of the plurality of NCT images. ⟶ 520

Generate a mask for the targeted region of the non-contrast image using the extracted information from the contrast CT image. ⟶ 530

Segmenting the plurality of adapted CCT images to generate a corresponding plurality of segmentation masks. ⟶ 540

Establish a labelled training set, wherein the labelled training set includes pairs of NCT images and segmentation masks. ⟶ 550

Receive a labelled training set. ~ 710

Train a machine learning image segmentation algorithm. ~ 720

Output a trained image segmentation model usable for identifying structural features of a blood vessel in an NCT image. ~ 730

*800*
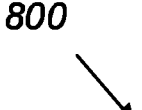
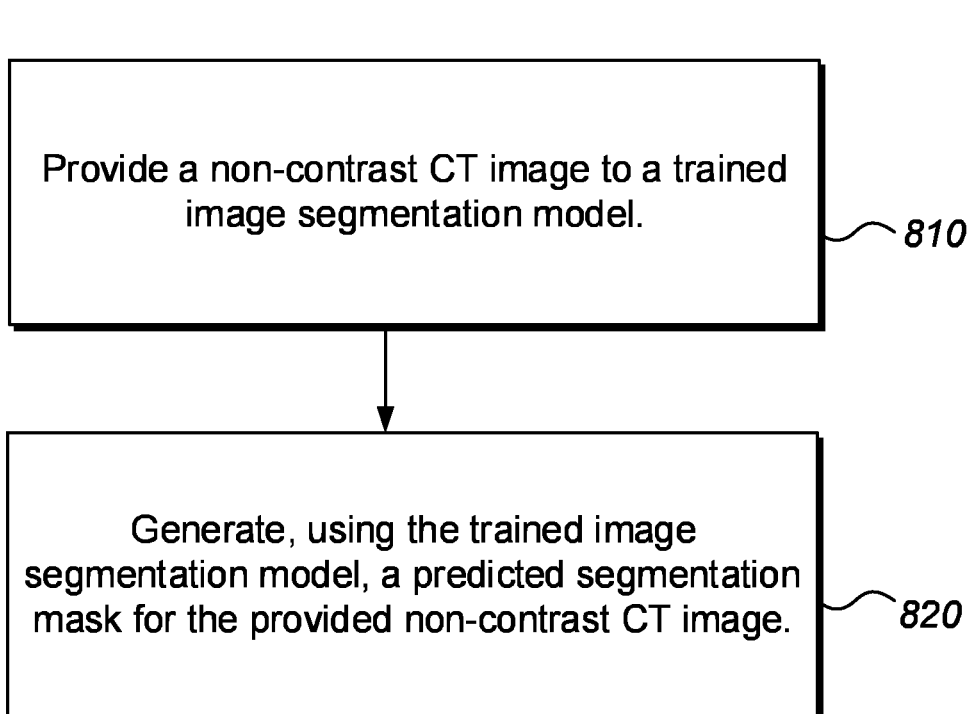
Provide a non-contrast CT image to a trained image segmentation model.
*810*
Generate, using the trained image segmentation model, a predicted segmentation mask for the provided non-contrast CT image.
*820*
FIG. 8

Abdominal Aortic Aneurysm Region
Isotropic Images
[144 x 144 x 96] patches

| Train (n =50) | DICE(%) |
| --- | --- |
| Inner lumen | 84.6 ± 8.6 % |
| ILT/Wall structure | 82.1 ± 17.3 % |

| Test (n =25) | DICE(%) |
| --- | --- |
| Inner lumen | 83.3 ± 9.3 % |
| ILT/Wall structure | 78.6 ± 12.2% |

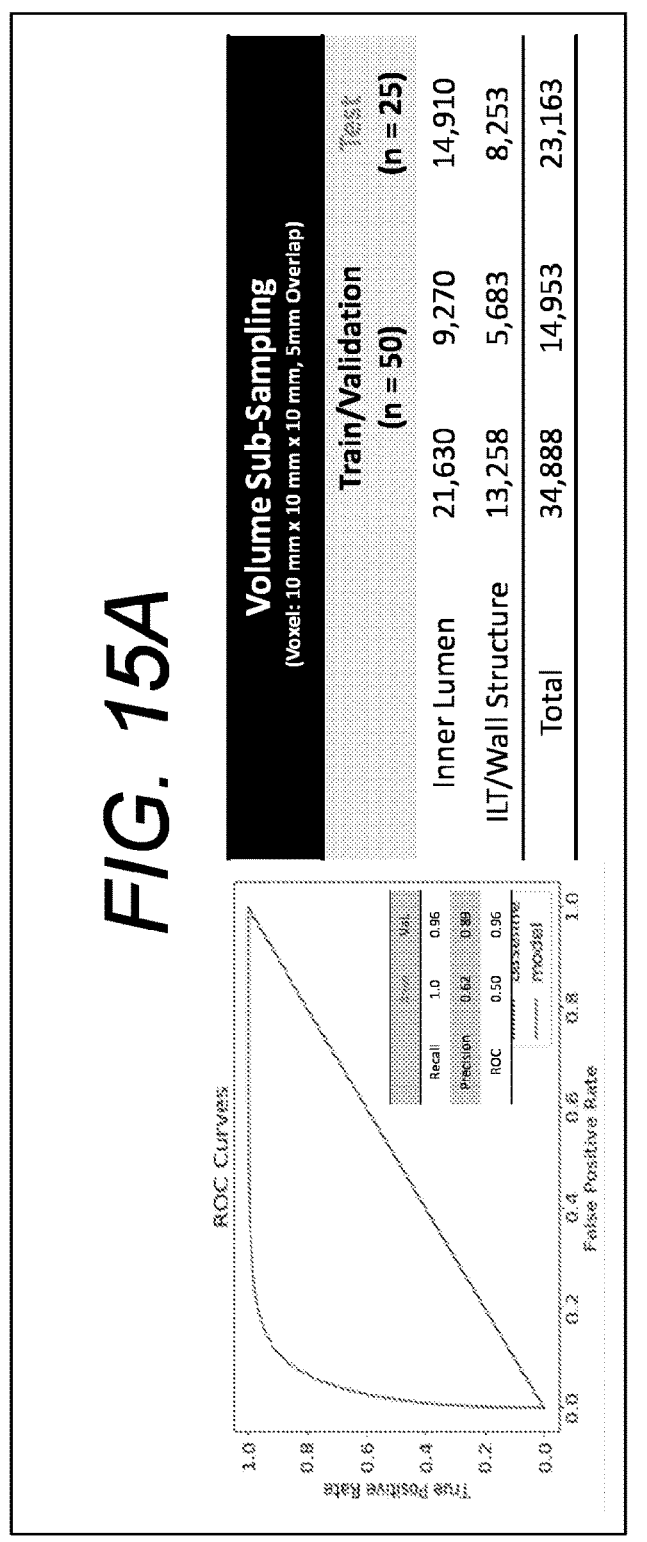
FIG. 15A
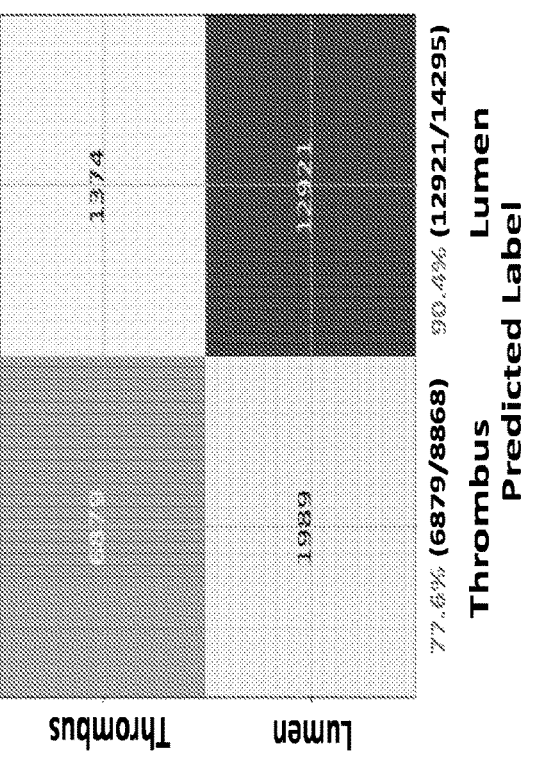
FIG. 15B

Volume Sub-Sampling
(Voxel: 10 mm x 10 mm x 10 mm, 5mm Overlap)

| FOLD 1 | Train/Validation (n = 50) | Test (n = 25) |
|---|---|---|
| Inner Lumen | 21,630 | 14,910 |
| ILT/Wall Structure | 13,258 | 8,253 |
| Total | 34,888 | 14,953 | 23,163 |

Volume Sub-Sampling
(Voxel: 10 mm x 10 mm x 10 mm, 5mm Overlap)

| FOLD 2 | Train/Validation (n = 50) | Test (n = 25) |
|---|---|---|
| Inner Lumen | 27,707 | 11,875 | 19,354 |
| ILT/Wall Structure | 11,836 | 5,072 | 10,567 |
| Total | 39,543 | 16,947 | 29,921 |

Volume Sub-Sampling
(Voxel: 10 mm x 10 mm x 10 mm, 5mm Overlap)

| FOLD 3 | Train/*Validation* (n=50) | Test (n=25) |
|---|---|---|
| Inner Lumen | 31,080    13,320 | 14,572 |
| ILT/Wall Structure | 15,009    6,433 | 6,033 |
| Total | 46,089    19,753 | 20,605 |

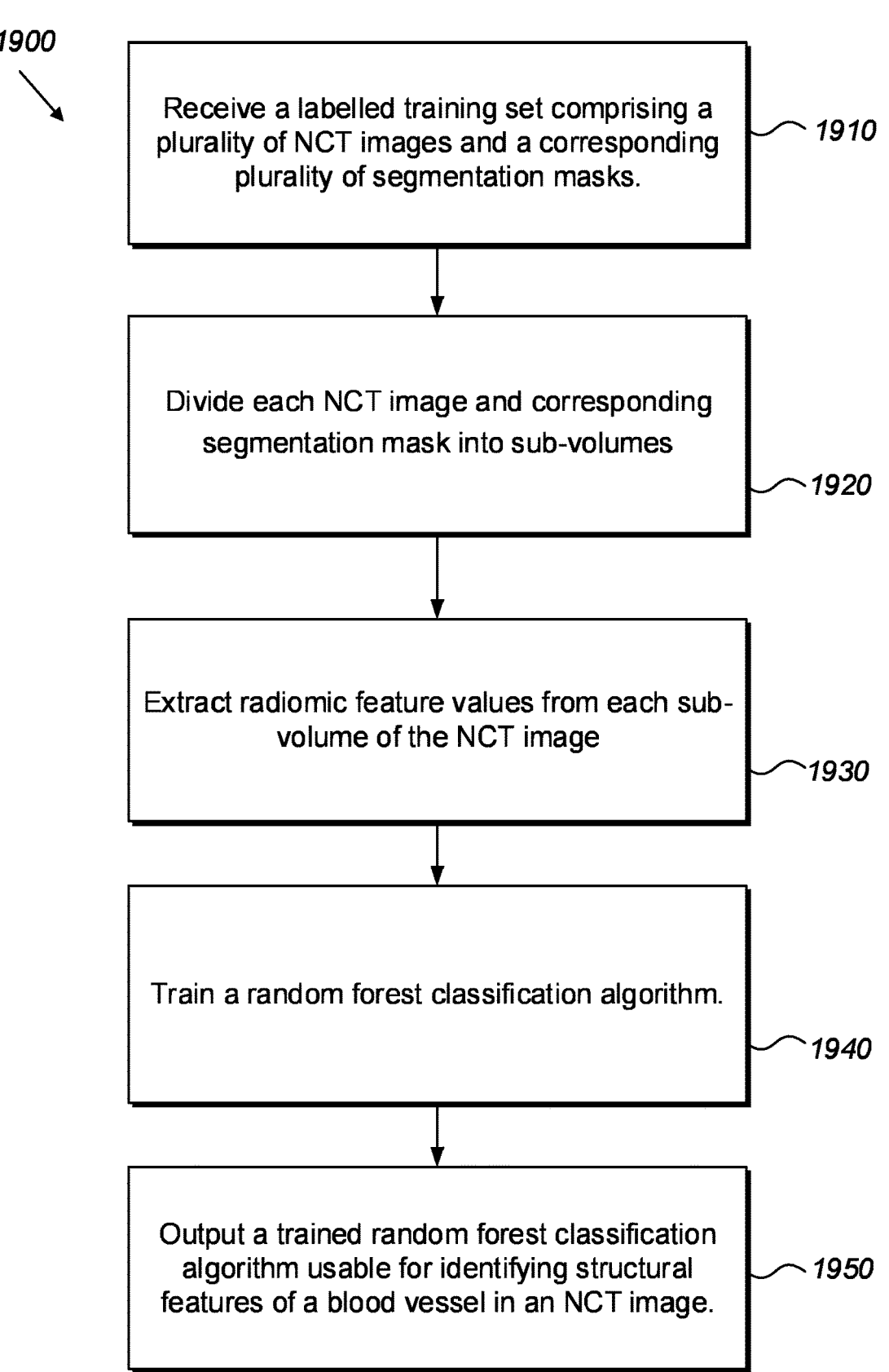

*1900*

Receive a labelled training set comprising a plurality of NCT images and a corresponding plurality of segmentation masks. — *1910*

Divide each NCT image and corresponding segmentation mask into sub-volumes — *1920*

Extract radiomic feature values from each sub-volume of the NCT image — *1930*

Train a random forest classification algorithm. — *1940*

Output a trained random forest classification algorithm usable for identifying structural features of a blood vessel in an NCT image. — *1950*

*FIG. 19*

2000
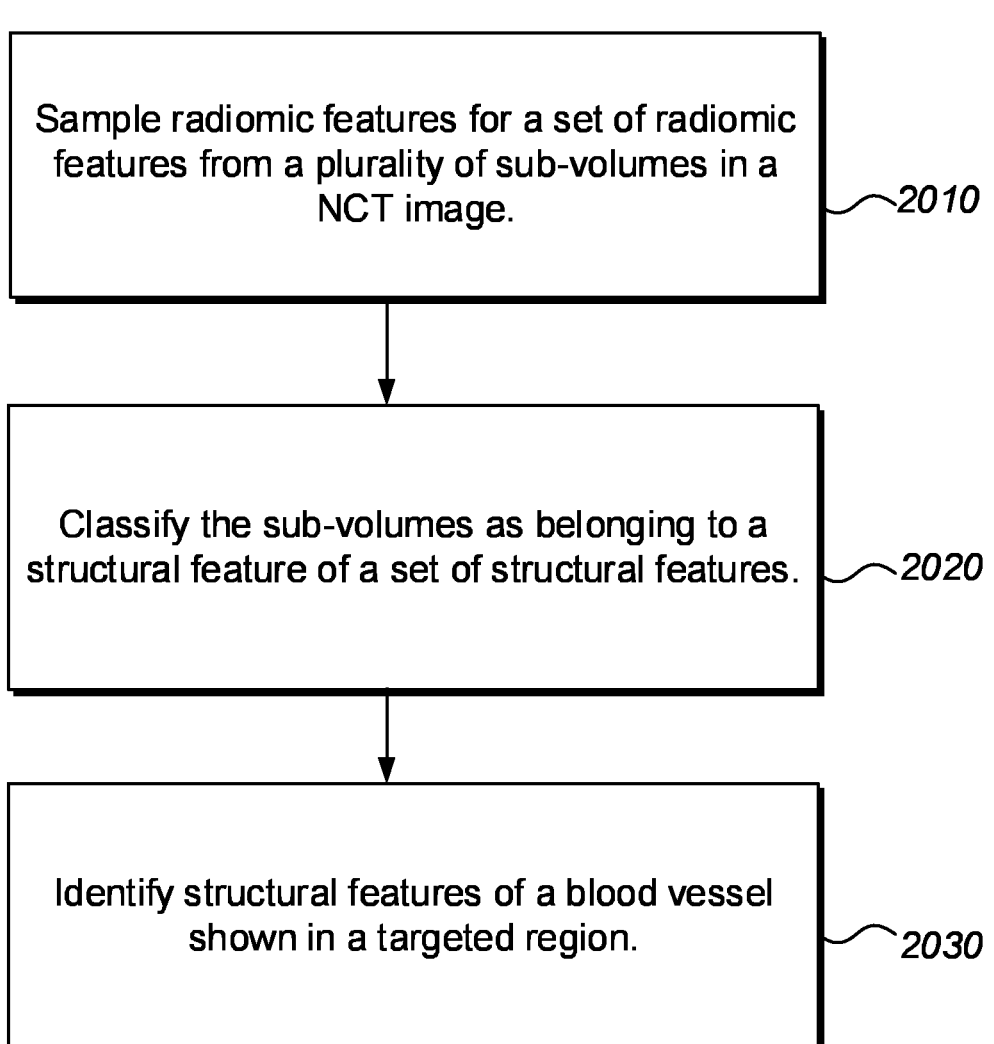
Sample radiomic features for a set of radiomic features from a plurality of sub-volumes in a NCT image.　　2010
Classify the sub-volumes as belonging to a structural feature of a set of structural features.　　2020
Identify structural features of a blood vessel shown in a targeted region.　　2030
*FIG. 20*

| B. | n = 75 | NC2C-CGAN | NC2C-Cycle-GAN |
|---|---|---|---|
| | RMSE | 11.9 ± 7.3 | 11.5 ± 6.9 |
| DICE | Inner | 85.2 ± 11.4 % | 85.6 ± 14.5 % |
| | Comb. | 94.9 ± 4.3 % | 95.4 ± 4.0 % |

3000
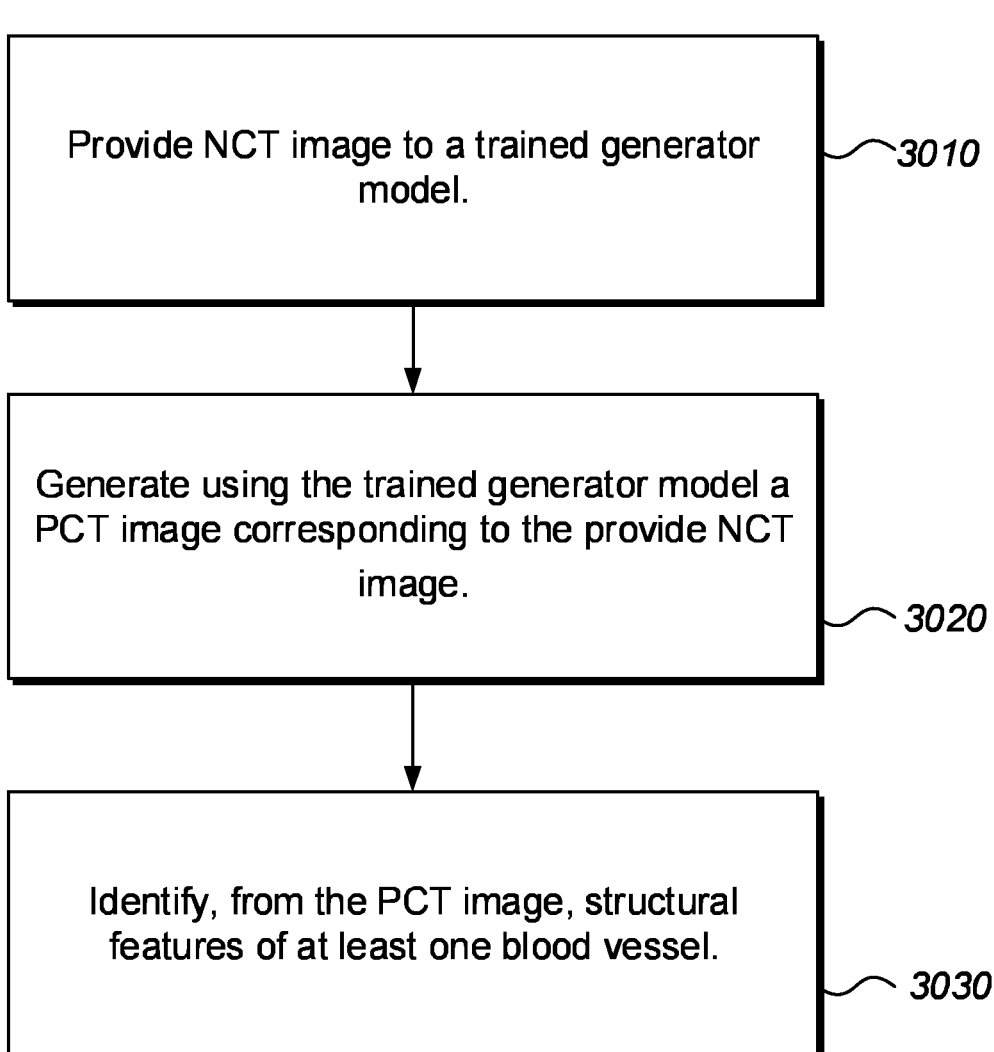
Provide NCT image to a trained generator model. ⌇3010
Generate using the trained generator model a PCT image corresponding to the provide NCT image. ⌇3020
Identify, from the PCT image, structural features of at least one blood vessel. ⌇3030
FIG. 30

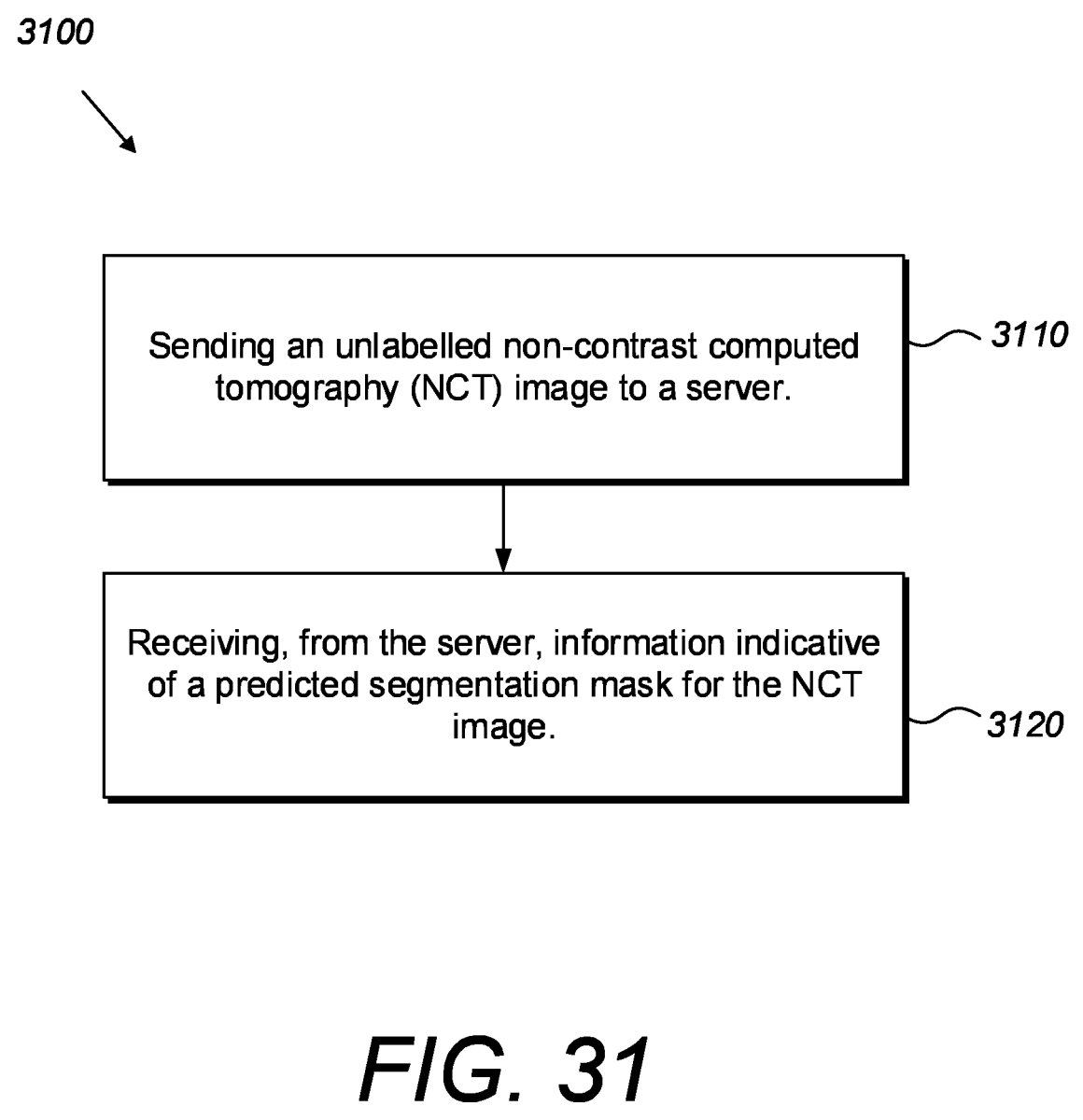

*3100*

Sending an unlabelled non-contrast computed tomography (NCT) image to a server.    *3110*

Receiving, from the server, information indicative of a predicted segmentation mask for the NCT image.    *3120*

FIG. 31

Processor

3310

3300

Machine-readable storage medium

Instructions

3320

COMPUTERIZED TOMOGRAPHY IMAGE PROCESSING

CROSS-REFERENCE TO RELATED APPLICATIONS

This application is the National Stage of International Application No. PCT/GB2020/052013, filed Aug. 21, 2020, which claims priority to GB 1912149.0, filed Aug. 23, 2019, GB 2001792.7, filed Feb. 10, 2020, GB 2001791.9, filed Feb. 10, 2020, and GB 2002987.2, filed Mar. 2, 2020, which are entirely incorporated herein by reference.

TECHNICAL FIELD

The present disclosure relates to computerised tomography (CT) imaging. More particularly, the present disclosure relates to the use of machine learning algorithms in the processing of CT images, and the use of radiomic feature analysis in the processing of CT images.

BACKGROUND

A computerised tomography (CT) scan, sometimes referred to as a CAT scan, is a diagnostic imaging procedure which uses x-rays impinging on a subject, such as the human body, to produce cross-sectional images, sometimes called slices, of a targeted region of the subject. The CT images are usually captured at a range of angles about the subject. The cross-sectional slices are then collated to produce a detailed three-dimensional image of the targeted region of the subject, which can be used to diagnose conditions including damage to bones, injuries to internal organs, problems with blood flow, stroke, and cancer.

An abdominal aortic aneurysm (AAA) is an example of a condition that may be diagnosed using CT images obtained from a CT scan. AAA is a bulging, dilation, or ballooning in the wall of the abdominal aorta, caused due to weakness or degeneration that develops in a portion of the abdominal aorta. Due to the constant pressure on the walls of the abdominal aorta, the aneurysm enlarges, stretching the walls of the artery thinner, thereby compromising the artery wall's ability to stretch any further. At this point, the aneurysm is at risk of rupturing and causing potentially fatal bleeding, just as a balloon will pop when blown up too much. Images obtained from a CT scan can enable medical/surgical professionals to monitor the growth of the aneurysm in the patient and/or make plans for surgical repair of the aneurysm. Of course, CT scans are also beneficial in diagnosing and treating other conditions. In particular, CT angiograms are widely utilised in all fields of cardiovascular surgery/medicine.

In order to make blood vessels such as the abdominal aorta visible on a CT image, a radiocontrast agent (hereafter referred to as a contrast agent) can be introduced into the patient. As the radiodensity of blood and the surrounding tissue is similar it can be difficult for the human eye to distinguish the interface between blood vessels and the surrounding tissue on CT images obtained without a contrast agent. The introduction of a contrast agent helps distinguish or "contrast" selected areas of the body from the surrounding tissue. There are numerous types of contrast agents, most of which are iodine based.

Contrast agents have a chemical structure such that they limit the ability of x-rays to pass or reflect or refract x-rays. As the contrast material only fills the arterial (or venous) spaces to which blood travels, the radiodensity of the contrast agent in the blood in the blood vessels is different to that of the surrounding tissue. As a result, CT images obtained with a contrast agent help distinguish blood vessels and features of the blood vessels from the surrounding tissue. In the case of AAAs, there is usually thrombus lining within the aneurysm sac. Full visualisation of the thrombus morphology, and its relation to the artery wall is important for monitoring the growth of the aneurysm and/or making plans for surgical repair of the aneurysm.

In many situations, as a matter of course, a patient/subject has a non-contrast CT scan (that is, a CT scan when no contrast agent has been provided to the patient) soon after arrival in a hospital or other suitable medical facility. The patient is often later injected with a contrast agent and a contrast CT scan (that is, a CT scan while a contrast agent is inside the subject's body) is performed. In such circumstances, the patient is therefore exposed to x-rays on two occasions; once when the non-contrast CT scan is performed and once when the contrast CT scan is performed. For some patients, who may require repeated hospital visits, the repeated exposure to x-rays is undesirable and may be detrimental to health.

Furthermore, the administration of contrast agents requires the insertion of a needle for injection of the contrast agent into the blood stream. This causes discomfort for the patients and has associated risks such as inadvertent arterial puncture by the needle, and contrast agent leakage outside the veins which can cause skin damage. In addition, the contrast agents can cause renal toxicity and acute kidney injury (contrast induced nephropathy—CIN). The incidence of CIN is as high as 10% after a CT scan obtained with a contrast agent. This is a particular problem in the elderly population who have worse baseline kidney functions, or in patients with declining kidney function/chronic kidney disease. In these patients, there is a small but recognised risk of complete kidney failure induced by CIN, which may lead to renal dialysis. Patients who are allergic to iodine are also unable to have intravenous contrast agents.

The present application addresses several of the problems described above.

SUMMARY

The inventors have recognised that computerised tomography (CT) images obtained without the administration of a contrast agent have enough information embedded within them to be able to distinguish between neighbouring regions.

As used in the present specification and in the appended claims the term "contrast CT image" or "contrast-enhanced CT image" is understood to mean an x-ray image obtained from a CT scan performed on a subject with a contrast agent present within the subject during scanning. Often herein, the term "contrast CT image" and the term "contrast-enhanced CT image" are abbreviated to "CCT image". The term "non-contrast CT image" as used herein is understood to mean an x-ray image obtained from a CT scan performed on a subject in the absence of a contrast agent. Often herein, the term "non-contrast CT image" is abbreviated to "NCT image". In CT scans, the values of voxels are usually given in Hounsfield units, giving the opacity of material to x-rays.

In several examples described herein, reference is made to a pseudo-contrast CT image, often herein abbreviated to "PCT image". A PCT image is understood to mean a generated image resembling a CCT image—that is, a PCT image is a simulated/synthetic/artificial image indicating structural features that would be visible in a CT scan performed on a subject with a contrast agent present within the subject during scanning. In examples described herein, a PCT image may be generated from an input NCT image of a target region to indicate structural features that would have been visible in a CCT image of that target region. A PCT image may be a 2D image or a 3D image (for example a reconstruction of a blood vessel).

According to an aspect of the invention, a method is described herein. The method is suitable for establishing a labelled training set for training a machine learning image segmentation algorithm to identify structural features of a blood vessel in a non-contrast computed tomography (NCT) image. The method comprises receiving a plurality of NCT images, each NCT image showing a targeted region of a subject, the targeted region including at least one blood vessel. The method further comprises receiving a plurality of contrast computed tomography (CCT) images, each CCT image corresponding to an NCT image of the plurality of NCT images and showing the corresponding targeted region of the subject. The method further comprises adapting the plurality of CCT images to substantially align with the corresponding NCT images. The method further comprises segmenting the plurality of adapted CCT images to generate a corresponding plurality of segmentation masks, each segmentation mask labelling at least one structural feature of the at least one blood vessel in the corresponding adapted CCT image. The labelled training set includes pairings of NCT images and segmentation masks, each pairing comprising a segmentation mask and the NCT image to which the adapted CCT image substantially aligns.

According to an aspect of the invention, a method is described herein. The method is suitable for establishing a labelled training set for training a classification algorithm (for example, a random forest classification algorithm) to identify structural features of a blood vessel in a non-contrast computed tomography (NCT) image. The method comprises receiving a plurality of NCT images, each NCT image showing a targeted region of a subject, the targeted region including at least one blood vessel. The method further comprises receiving a plurality of contrast computed tomography (CCT) images, each CCT image corresponding to an NCT image of the plurality of NCT images and showing the corresponding targeted region of the subject. The method further comprises adapting the plurality of CCT images to substantially align with the corresponding NCT images. The method further comprises segmenting the plurality of adapted CCT images to generate a corresponding plurality of segmentation masks, each segmentation mask labelling at least one structural feature of the at least one blood vessel in the corresponding adapted CCT image. The labelled training set includes pairings of NCT images and segmentation masks, each pairing comprising a segmentation mask and the NCT image to which the adapted CCT image substantially aligns.

The inventors have recognised that NCT images may be used in place of CCT images in identifying/visually reconstructing structural features of a blood vessel. As mentioned above, when a patient or other subject arrives at a hospital or other medical facility for a contrast CT scan, a non-contrast CT pre-scan is often taken as a matter of course. The non-contrast CT scan represents a rich data-source, that can be used to provide training data for training a machine learning algorithm according to a method as described herein. In particular, the training set can be used to train a machine learning image segmentation model or a classification algorithm to identify structural features of a blood vessel in a non-contrast computed tomography image.

Advantageously, after training, such a trained model enables the analysis of a blood vessel of interest without the need for the subjects to be injected with contrast agents prior to a CT scan. This in turn means that subjects need not be exposed to unnecessary x-ray radiation from further scans, potential side effects of injected contrast agents, or the pain and discomfort of being injected with a contrast agent. Further advantages would be clear to the skilled person.

The term "training set" as used herein in reference to training an image segmentation algorithm or a classification algorithm is understood to mean the dataset obtained from a plurality of non-contrast and contrast CT images of multiple patients or the same patient which is used to train an image segmentation algorithm or a classification algorithm to label or otherwise identify the features of one or more blood vessels in an NCT image. For example, a contrast CT scan and a non-contrast CT scan of a subject would ordinarily generate several CT images of that subject. In establishing the training set, one or more of such images for the patient may be used. Additionally, one or more CT images from at least one further patient may also be used. The training set may be established from CT scan data for many patients, with many CT images for each patient. A segmentation mask identifying features of a blood vessel in a contrast CT image may be mapped to a non-contrast CT image. The training set may accordingly include an NCT image and a respective segmentation mask.

The machine learning image segmentation algorithm may learn by receiving the NCT image as input and comparing the resultant output to the respective segmentation mask, and then adjusting internal weights and biases via a back-propagation algorithm.

A classification algorithm may also be trained using the training set. Each NCT image and corresponding segmentation mask may be divided into sub-volumes, each sub-volume labelling at least one structural feature of a blood vessel in a corresponding NCT image of a plurality of NCT images. Radiomic feature values for a set of radiomic features may then be extracted from each sub-volume of an NCT image, and the classification algorithm may be trained using the extracted radiomic feature values for each sub-volume of each NCT image and the corresponding sub-volume of the corresponding segmentation masks, to learn features of the NCT images that correspond to structural features of the blood vessels labelled in the segmentation masks.

The methods of establishing labelled training sets may further comprise expanding the training set by applying transformations to the NCT images and corresponding segmentation masks (i.e. adjusting the sheer and/or divergence) in order to further diversify the training set and therefore to improving the ability of the algorithm to learn. Throughout this specification, reference to a training set comprising NCT images and segmentation masks may be understood also to refer to such digitally transformed/augmented expanded datasets.

In computer vision, image segmentation is the process of partitioning a digital image into multiple segments. A goal of segmentation is to simplify and/or change the representation of an image into something that is more meaningful and easier to analyse. Image segmentation is typically used to locate objects and boundaries (lines, curves, etc.) in images. More particularly, image segmentation is the process of assigning a label to pixels/voxels in an image such that pixels/voxels with the same label share certain characteristics or computed properties such as colour or intensity.

A segmentation mask as used herein may be understood to mean a labelling of features in the corresponding CT image from which it was generated. More particularly, a segmentation mask may be understood to mean a labelling of pixels/voxels in at least one region of a corresponding CT image, such that pixels/voxels with the same label share characteristics, and may be mappable back to features in the target region shown in the scan. For example, features of a blood vessel in a contrast CT image may be manually labelled or tagged in some way identifiable to a computer processor, or traditional image segmentation algorithms may be used to pick out the features of the blood vessel of interest. The data concerning the labelling or tagging may be referred to as a segmentation mask. The segmentation mask may be produced from a contrast CT image, which has itself been adapted to align substantially with a corresponding non-contrast image. Accordingly, the segmentation mask may be used as "ground truth" in the machine learning algorithm. Although derived from an adapted CCT image, a segmentation mask is used as the basis for training a machine learning image segmentation algorithm to identify features in an NCT image which would not ordinarily clearly show such features.

A segmentation mask may also be known as a pre-defined segmentation, segmentation data, a segmentation template, segmented contours, a labelled dataset, or a labelled segmentation. Each segmentation mask of the plurality of segmentation masks may comprise a binary segmentation mask, (e.g. in which each region is labelled as a "0" or a "1", or as foreground or background for example). A segmentation mask may not be binary. For example, a segmentation template may contain several labels to distinguish between several different regions. As an example, a segmentation template may include an RGB colouring or any other such labelling.

The phrase "receive a plurality of NCT images" as used herein is understood to mean receiving data representative of one or more non-contrast CT scans. The data may be in any suitable format. The receiving may be performed, for example, by one or more processors of a computing apparatus (such as that shown in FIG. 6). The data may comprise information relating to the measured intensity of the x-rays which is used to reconstruct a non-contrast CT image using various known CT reconstruction techniques. Similarly, "receiving a plurality of contrast computed tomography (CCT) images" is understood to mean receiving data representative of one or more contrast CT scans. The data may be in any suitable format. The receiving may be performed, for example, by one or more processors of a computing apparatus (such as that shown in FIG. 6). The data may comprise information relating to the measured intensity of the x-rays which is used to reconstruct a contrast CT image using various known CT reconstruction techniques.

The term "targeted region" as used herein is understood to mean the region of a subject/patient on a CT image that is of medical/clinical interest to the medical practitioner/surgeon, for example a chest cavity, an abdominal cavity or any other region of interest. For example, in the case of a patient having an abdominal aortic aneurysm (AAA), the targeted region as used herein may be understood to mean a region of focus occupied by the abdominal aorta on the CT image. The targeted region may, of course, include more than one blood vessel. The blood vessel may be any blood vessel, and particularly blood vessels that would appear differently on CCT scans and NCT scans.

The blood vessel may be any suitable blood vessel, for example a vein or an artery. For example, the at least one blood vessel of the targeted region of the non-contrast CT image may include the aorta. For example, the at least one blood vessel of the targeted region of the CT image may include a renal artery. For example, the at least one blood vessel of the targeted region of the CT image may include a mesenteric artery. For example, the at least one blood vessel of the targeted region of the CT image may include an iliac artery.

Structural features may comprise any anatomical or pathological features discernible from a CT scan. For example, structural features may be understood to mean features of a blood vessel having a distinct intrinsic nature identifiable through image segmentation. For example, a structural feature may comprise an arterial or venous wall, an outer diameter or inner diameter of a blood vessel and so on. The structural features of at least one blood vessel may include for example the outer wall or outer lumen and/or the inner lumen of the blood vessel. Structural features may be any anatomical or pathological features discernible from a CT scan (such as calcification, dissection flaps, false lumen, ulcers, atherosclerotic plaque, thrombus etc).

In some examples, the structural features may comprise structural features of an aneurysm, for example an aortic aneurysm. The structural features of the aortic aneurysm may include for example the thrombus, and lumen of the aorta, where the thrombus is predominantly fibrinous and collagenous, with red cells/platelets, whereas the lumen is predominantly filled with red blood cells. Structural features may include one or more boundaries for example.

Structural features may include the outer lumen.

A subject may be understood to mean a human or animal or other suitable organism having blood vessels, or a sample therefrom.

Adapting the plurality of CCT images may comprise orienting the plurality of CCT images to substantially align with the corresponding NCT image. Adapting the plurality of CCT images may comprise scaling the plurality of CCT images to substantially align with the corresponding NCT images. "Adapting" may be understood to mean any digital transformation. In particular, adapting the plurality of CCT images to substantially align with an NCT image may be understood to mean performing any suitable image transformations to the CCT image such that features of the CCT image can be mapped to appropriate regions of the NCT image. Due to the fact that, for example, a contrast-enhanced CT scan may be taken at a different time to the non-contrast CT scan, the subject and/or the subjects blood vessels may not be positioned the same in both scans, and accordingly, some adaption of the CCT images may be required. By adapting the CCT images, one enables the generated segmentation masks to be used for identifying features in the corresponding NCT images. Adapting may comprise performing any spatial transformation to the image. Adapting may comprise aligning the NCT and the CCT scans and overlaying the static components of the two images. Each CT scan may comprise meta-data that dictates the spatial location of each slice relative to an arbitrary point, specific to a CT scanner. Adapting may comprise comparing this information between the CCT and NCT images to generate a rotation matrix. This matrix encodes the information to rotate the NCT image volume from its axis to that of the CCT image volume. Adapting may comprise after rotating the images, comparing the xyz-axis parameters between the image pairs and translating the images to maximize axial alignment.

The labelled training set may comprise pairings of NCT images and segmentation masks, each pairing comprising a segmentation mask and the NCT image to which the adapted CCT image substantially aligns. The segmentation mask thus can be used in labelling pixels/voxels in the corresponding NCT image. The word "pairing" should be interpreted broadly—in particular, a pairing may consist only of the segmentation mask and the corresponding NCT image, or may include further information. The words "tuple", "collection", "grouping" and so on may be understood to mean the same thing.

According to an aspect of the invention, a computer-readable medium is provided. The computer-readable medium has instructions stored thereon which, when executed by one or more processors, cause the one or more processors to implement a method as described herein for establishing a labelled training set. The computer-readable medium may comprise a non-transitory computer-readable medium. The computer-readable medium may comprise, for example, a USB stick, a hard drive, or some other memory unit.

According to an aspect of the invention, a computer-readable medium is provided. The computer-readable medium has stored thereon a labelled training set. The labelled training set comprises a plurality of NCT images, each NCT image of the plurality of NCT images showing a targeted region of a subject, the targeted region including at least one blood vessel. The computer-readable medium further comprises a corresponding plurality of segmentation masks, each segmentation mask labelling at least one structural feature of a blood vessel in a corresponding NCT image of the plurality of NCT images. The labelled training set may be suitable for training an image segmentation algorithm, for example a neural network, to identify structural features of a blood vessel in a NCT image. The labelled training set may be suitable for training a classification algorithm, such as a random forest classification algorithm, to identify structural features of a blood vessel in a NCT image.

According to an aspect of the invention, a computing apparatus is provided. The computing apparatus is suitable for establishing a labelled training set for training a machine learning image segmentation algorithm to identify structural features of a blood vessel in a non-contrast computed tomography (NCT) image for identifying structural features of a blood vessel in an unlabelled non-contrast computed tomography (NCT) image. The apparatus comprises one or more memory units. The apparatus further comprises one or more processors configured to execute instructions stored in the one or more memory units to perform a method as described herein for establishing a training set.

According to an aspect of the invention, a method is described herein for training a machine learning image segmentation algorithm to identify structural features of a blood vessel in a non-contrast computed tomography (NCT) image. The method comprises receiving a labelled training set for the machine learning image segmentation algorithm. The labelled training set comprises a plurality of NCT images, each NCT image of the plurality of NCT images showing a targeted region of a subject, the targeted region including at least one blood vessel. The labelled training set further comprises a corresponding plurality of segmentation masks, each segmentation mask labelling at least one structural feature of a blood vessel in a corresponding NCT image of the plurality of NCT images. The method further comprises training a machine learning image segmentation algorithm, using the plurality of NCT images and the corresponding plurality of segmentation masks, to learn features of the NCT images that correspond to structural features of the blood vessels labelled in the segmentation masks, and output a trained image segmentation model. The method further comprises outputting the trained image segmentation model usable for identifying structural features of a blood vessel in an NCT image. Advantageously, such a trained image segmentation model can be used to identify structural features of a blood vessel in an NCT image.

The labelled training set may or may not have been established using a method as described further above. Each segmentation mask may have been generated from a corresponding contrast computed tomography (CCT) image, each CCT image corresponding to an NCT image of the plurality of NCT images and showing the features of the blood vessel in the targeted region of the corresponding NCT image.

The method may further comprise generating the labelled training set. Generating the labelled training set may comprise performing a method as described herein for establishing a labelled training set.

The machine learning image segmentation algorithm may be any suitable machine learning image segmentation algorithm. For example, the machine learning image segmentation algorithm may comprise a neural network. For example, the machine learning image segmentation algorithm may comprise a convolutional neural network. The machine learning image segmentation algorithm may be trained by minimising a cost function involving the segmentation mask information ("ground truth") and the output of the final layer of the network. The cost function may comprise any suitable cost function such as a quadratic cost function, a cross-entropy cross function, a log-likelihood cost function. The minimisation may be performed for example by gradient descent, stochastic gradient descent or variations thereof, using backpropagation to adjust weights and biases within the neural network accordingly. Training may involve the use of further techniques known to the skilled person, such as regularization. Mini-batch sizes and numbers of epochs may be selected and fine-tuned during training. The neural network may comprise several layers of neurons (which may be, for example, perceptrons, sigmoid neurons, tanh neurons, or rectified linear units/rectified linear neurons), and may include one or more convolution layers, and may include one or more max-pool layers, and may include a soft-max layer.

A trained image segmentation model may accordingly be understood to include all information determined in training. For example, the trained image segmentation model may include the complete collection of weights and biases for neurons established during training and details of hyperparameters such as the learning rate and mini-batch size.

The trained segmentation model may be validated using metrics such as the Sorensen-Dice coefficient, also known as a DICE score, which is a statistic used to gauge the similarity of two samples. That is, one may validate the model by calculating a DICE score or some other metric for a known segmentation mask ("ground truth") and a segmentation mask output from the model.

According to an aspect of the invention, a computer-readable medium is described herein. The computer-readable medium has instructions stored thereon which, when executed by one or more processors, cause the one or more processors to implement a method for training a machine learning image segmentation algorithm as described herein. The computer-readable medium may comprise a non-transitory computer-readable medium. The computer-readable medium may comprise, for example, a USB stick, a hard drive, or some other memory unit.

According to an aspect of the invention, a computing apparatus is provided herein. The computing apparatus is suitable for training a machine learning image segmentation algorithm to identify structural features of a blood vessel in a non-contrast computed tomography (NCT) image. The apparatus comprises one or more memory units. The computing apparatus further comprises one or more processors configured to execute instructions stored in the one or more memory units to perform a method for training a machine learning image segmentation algorithm as described herein.

According to an aspect of the invention, a method is described herein for identifying structural features of a blood vessel in an unlabelled non-contrast computed tomography (NCT) image. The method comprises providing the NCT image to a trained image segmentation model, the trained image segmentation model trained to learn features of NCT images that correspond to structural features of blood vessels. The method further comprises generating, using the trained image segmentation model, predicted segmentation data for the provided NCT image, the predicted segmentation data for identifying the features of the blood vessel in the provided NCT image. Advantageously, such a method can be used to identify structural features of blood vessels in NCT images for which no corresponding CCT images were ever taken. That is, the method may be used to reconstruct the blood vessel (e.g. the aorta) from a non-contrast CT scan, thereby meaning that the subject need not also be injected with a contrast agent and need not be required to have a contrast-enhanced CT scan performed. Structural features of arteries/veins can thus be analysed even in historic NCT scan images. The trained image segmentation model may have been trained according to a method as described herein.

The predicted segmentation data/predicted segmentation mask may be understood to mean the labelling of the NCT image output from the method. That is, the predicted segmentation mask/predicted segmentation data/predicted segmentation template comprises the labelling used to identify segments in the NCT image. The predicted segmentation mask may be output in suitable form, for example as a digital file that can be mapped by the user on to the NCT image. Additionally or alternatively, the predicted segmentation mask may be provided in an adapted version of the NCT image containing, for example, a colouring in or highlighting of a segmented region. The predicted segmentation mask may even be presented as a pseudo-contrast computed tomography (PCT) image.

According to an aspect of the invention, a computer-readable medium is described herein. The computer-readable medium has stored thereon predicted segmentation data generated using a method as described herein. The computer-readable medium may comprise a non-transitory computer-readable medium. The computer-readable medium may comprise, for example, a USB stick, a hard drive, or some other memory unit.

According to an aspect of the invention, a computer-readable medium is described herein. The computer-readable medium has stored thereon computer-readable code representative of the trained image segmentation model. The computer-readable medium may comprise a non-transitory computer-readable medium. The computer-readable medium may comprise, for example, a USB stick, a hard drive, or some other memory unit.

According to an aspect of the invention, a computer-readable medium is described herein. The computer-readable medium may further have instructions stored thereon which, when executed by one or more processors, cause the one or more processors to implement a method as described herein to identify structural features of a blood vessel in a non-contrast computed tomography image. The computer-readable medium may comprise a non-transitory computer-readable medium. The computer-readable medium may comprise, for example, a USB stick, a hard drive, or some other memory unit.

According to an aspect of the invention, a computing apparatus is described herein. The computing apparatus is suitable for identifying structural features of a blood vessel in an unlabelled non-contrast computed tomography (NCT) image. The apparatus comprises one or more memory units. The apparatus further comprises one or more processors configured to execute instructions stored in the one or more memory units to perform a method as described herein to identify structural features of a blood vessel in a non-contrast computed tomography image.

According to an aspect of the invention, a method is described herein for training a classification algorithm to identify structural features of a blood vessel in a non-contrast computed tomography (NCT) image. The method comprises receiving a labelled training set for the classification algorithm. The labelled training set comprises a plurality of NCT images, each NCT image of the plurality of NCT images showing a targeted region of a subject, the targeted region including at least one blood vessel. The labelled training set further comprises a corresponding plurality of segmentation masks, each segmentation mask labelling at least one structural feature of a blood vessel in a corresponding NCT image of the plurality of NCT images. The method further comprises dividing each NCT image and corresponding segmentation mask into sub-volumes, each sub-volume of the corresponding segmentation mask labelling at least one feature in a corresponding sub-volume in the corresponding NCT image. The method further comprises extracting, from each sub-volume of the NCT image, radiomic feature values for a set of radiomic features. The method further comprises training a classification algorithm, using the extracted feature values for each sub-volume of each NCT image and the corresponding sub-volume of the corresponding segmentation masks, to learn features of the NCT images that correspond to structural features of the blood vessels labelled in the segmentation masks and output a trained classification model. The method further comprises outputting the trained classification model usable for identifying structural features of a blood vessel in an NCT image. Advantageously, such a trained classification algorithm can be used to identify structural features of a blood vessel in an NCT image.

The classification algorithm may comprise any suitable classification algorithm. For example, the classification algorithm may comprise for example be based on regression modelling. In examples described herein, a classification algorithm comprises a random forest classification algorithm.

Random forest or random decision forest or random forest classification algorithm is an ensemble learning method which is used for classification, regression and other tasks that operate by constructing a multitude of decision trees during training of the algorithm and outputting the class that is the mode of the classes (classification) or mean prediction (regression) of the individual trees. Random forests are trained via the bagging method. Bagging or Bootstrap Aggregating, consists of randomly sampling subsets of the training data, fitting a model to these smaller data sets, and aggregating the predictions trained via the bagging method. The random forest classification algorithm may be trained using a labelled training set established as described further above. Each segmentation mask may have been generated from a corresponding contrast computed tomography (CCT)

image, each CCT image corresponding to an NCT image of the plurality of NCT images and showing the features of the blood vessel in the targeted region of the corresponding NCT image.

The volume subsamples may be of any suitable size, for example 1 cm×1 cm×1 cm. Subsamples may overlap. For example, the stride length between subsamples may be less than the size of the volume subsample.

According to an aspect of the invention, a computer-readable medium is described herein. The computer-readable medium has instructions stored thereon which, when executed by one or more processors, cause the one or more processors to implement a method for training a classification algorithm as described herein. The computer-readable medium may comprise a non-transitory computer-readable medium. The computer-readable medium may comprise, for example, a USB stick, a hard drive, or some other memory unit.

According to an aspect of the invention, a computer-readable medium is described herein. The computer-readable medium has stored thereon computer-readable code representative of the trained classification algorithm.

According to an aspect of the invention, a method is described herein for identifying structural features of a blood vessel from a non-contrast computed tomography (NCT) image, the NCT image showing a targeted region of a subject, the targeted region including at least one blood vessel. The method comprises for each of a plurality of sub-volumes of the NCT image: sampling radiomic feature values for a set of radiomic features from the sub-volume, classifying the sub-volume as belonging to a structural feature of a set of structural features based on the sampled radiomic feature values; and identifying, from the classifications of the plurality of sub-volumes of the NCT image, structural features of a blood vessel shown in the targeted region. Advantageously, such a method can be used to identify structural features of blood vessels in NCT images for which no corresponding CCT images were ever taken. That is, the method may be used to reconstruct the blood vessel (e.g. the aorta) from a non-contrast CT scan, thereby meaning that the subject need not also be injected with a contrast agent and need not be required to have a contrast-enhanced CT scan performed. Structural features of arteries/veins can thus be analysed even in historic NCT scan images. According to an aspect of the invention, a computer-readable medium is provided, the computer-readable medium having instructions stored thereon which, when executed by one or more processors, cause the one or more processors to implement such a method for identifying structural features of a blood vessel in a non-contrast computed tomography image.

Classifying the sub-volume as belonging to a structural feature of a set of structural features based on the sampled radiomic features may comprise using a trained random forest classification algorithm trained according to the method described herein. However, the sub-volumes may be classified using different methods unrelated to random forests, for example using other classification algorithms or other method entirely. For example, in some examples, classifying the sub-volume as belonging to a structural feature of a set of structural features based on the sampled radiomic features comprises comparing radiomic features with corresponding threshold values. Comparing radiomic feature values with corresponding thresholds may comprise checking for at least a 10-fold difference between the radiomic feature values and the threshold values. Comparing radiomic features with corresponding thresholds may comprise checking for at least a 20-fold difference between the radiomic features and the threshold values.

According to an aspect of the invention, a method is described herein. The method comprises training a generative adversarial network (GAN) to generate a pseudo-contrast computed tomography (PCT) image from a non-contrast computed tomography (NCT) image, the GAN comprising a generator network and a discriminator network. The method comprises receiving a training set, wherein the training set comprises: a plurality of NCT images, each NCT image of the plurality of NCT images showing at least one anatomical structure, and a plurality of contrast computed tomography (CCT) images, each CCT image showing at least one anatomical structure. The method further comprises training the GAN, wherein training the GAN comprises: training the generator network, using the plurality of NCT images and feedback from the discriminator network, to generate PCT images, and training the discriminator network, using the generated PCT images and the plurality of CCT images, to classify received images as PCT images or CCT images and to provide feedback to the generator network. The method further comprises outputting a trained generator model to translate an input NCT image to a PCT image showing at least one anatomical structure.

The anatomical structure may be, for example, a blood vessel or features of a blood vessel. The anatomical structure may comprise an organ, for example a kidney.

A GAN is a class of machine learning frameworks, in which two neural networks—the generator network and the discriminator network—contest with each other in a game. The discriminator network is trained to distinguish between genuine CCT images and the artificial PCT images generated by the generator network, while the generator network is trained to produce candidate PCT images that can "fool" the discriminator. A known dataset serves as the initial training data for the discriminator network. Training it involves presenting it with samples from the training dataset, until it achieves acceptable accuracy. The generator network trains based on whether it succeeds in fooling the discriminator. PCT images synthesized by the generator are evaluated by the discriminator network. Backpropagation is applied in both networks so that the generator network produces better PCT images, while the discriminator becomes more skilled at discriminating between the PCT images and genuine CCT images.

A discrimination may comprise any suitable classifier, for example a neural network or a random forest. A generator may comprise any network suitable for generating images based on input images, for example a neural network. The generator may comprise a UNET. A GAN may comprise multiple generators and multiple discriminators (for example, in a cycle-GAN).

Advantageously, for a GAN to be trained the training set need not comprise NCT images and corresponding segmentation masks generated from CCT images of the same subject(s). Instead a GAN may be trained using NCT images and CCT images.

The GAN may comprise a Conditional-GAN (CGAN). A CGAN may be trained with paired NCT images and CCT images.

The GAN may comprise a cycle-GAN. Advantageously, a cycle-GAN does not require paired NCT images and CCT images in training. Instead, the NCT images used to train the generative network may even be of a different patient set to the CCT images used to help train the discriminator network. Accordingly, historical NCT images for which no corresponding CCT image is available can be included in the training set, and similarly historical CCT images for which no corresponding NCT image is available can be included in the training set. The training set for a cycle-GAN may comprise paired or unpaired NCT and CCT images.

The term "training set" as used herein in reference to training a GAN is understood to mean the dataset obtained from a plurality of non-contrast and contrast CT images of multiple patients which is used to train a GAN to generate one or more PCT images from NCT images, and which may be different to the "training set" defined above to train a machine learning image segmentation algorithm or a classification algorithm. In establishing the training set for training a GAN, one or more CCT and NCT images of several patients may be used. The training set may be established from CT scan data for many patients, with many CT images for each patient. The training set may include a plurality of NCT images and a plurality of CCT images.

The generative adversarial network (GAN) trained to generate a pseudo-contrast computed tomography (PCT) image may be a cycle-GAN or a conditional GAN (CGAN) architecture or any other generative adversarial network (GAN) architecture.

According to an aspect of the invention, a computer-readable medium is described herein. The computer-readable medium has instructions stored thereon which, when executed by one or more processors, cause the one or more processors to implement a method for training a generative adversarial network (GAN) as described herein. The computer-readable medium may comprise a non-transitory computer-readable medium. The computer-readable medium may comprise, for example, a USB stick, a hard drive, or some other memory unit.

According to an aspect of the invention, a method is described herein for identifying anatomical structures in a non-contrast computed tomography (NCT) image. The method comprises providing the NCT image to a trained generator model, the generator model trained as part of a generative adversarial network, the generator model trained to translate an input NCT image to a pseudo-contrast PCT image showing at least one anatomical structure. The method further comprises generating, using the trained generator model, a PCT image corresponding to the provided NCT image. The method further comprises outputting a trained generator model to translate an input NCT image to a PCT image showing at least one anatomical structure. The method further comprising identifying, from the PCT image, structural features of the at least one anatomical structure. Advantageously, such a method can be used to identify structural features of anatomical structures in NCT images for which no corresponding CCT images were ever taken.

According to an aspect of the invention, a computer-readable medium is described herein. The computer-readable medium has stored thereon computer-readable code representative of a trained generator model to translate an input NCT image to a PCT image showing at least one anatomical structure. The computer-readable medium may further have instructions stored thereon which, when executed by one or more processors, cause the one or more processors to implement a method as described herein to generate a PCT image from a NCT image. The computer-readable medium may comprise a non-transitory computer-readable medium. The computer-readable medium may comprise, for example, a USB stick, a hard drive, or some other memory unit.

According to an aspect of the invention, a method is described herein. The method comprises sending an unla-belled non-contrast computed tomography (NCT) image to a server, the NCT image showing a targeted region of a subject including at least one anatomical structure. The method further comprises receiving, from the server, predicted segmentation data for the NCT image, the predicted segmentation data labelling structural features of the at least anatomical structure. According to an aspect of the invention, a computing apparatus is provided for performing such a method. The apparatus may comprise one or more memory units. The computing apparatus may further comprise one or more processors configured to execute instructions stored in the one or more memory units to perform such a method. The server may perform a method for identifying structural features in an unlabelled non-contrast computed tomography (NCT) image as described herein. The server may be held by a third party.

The computer program and/or the code for performing such methods as described herein may be provided to an apparatus, such as a computer, on the computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid-state memory, magnetic tape, a removable computer diskette, a random-access memory (RAM), a read-only memory (ROM), a rigid magnetic disc, and an optical disk, such as a CD-ROM, CD-R/W or DVD.

Many modifications and other embodiments of the inventions set out herein will come to mind to a person skilled in the art to which these inventions pertain in light of the teachings presented herein. Therefore, it will be understood that the disclosure herein is not to be limited to the specific embodiments disclosed herein. Moreover, although the description provided herein provides example embodiments in the context of certain combinations of elements, steps and/or functions may be provided by alternative embodiments without departing from the scope of the invention.

BRIEF DESCRIPTION OF THE FIGURES

Embodiments of the invention will now be described by way of example only, with reference to the accompanying figures, in which:

FIG. 1A shows a non-contrast CT image of an abdominal aortic region;

FIG. 1B shows a contrast CT image of an abdominal aortic region;

FIG. 5 shows a flowchart;

FIG. 8 shows a flowchart;

FIG. 15A shows a table summarising the number of volume subsamples taken for a first experiment (Experiment 1) using the methodology of FIG. 14, and further shows an ROC curve;

FIG. 15B shows a confusion matrix for the results of the first experiment (Experiment 1);

FIG. 19 shows a flowchart;

FIG. 20 shows a flowchart;

FIG. 28A shows a confusion matrix comparing ILT regional classifications between generated images and ground truth segmentations derived from the Conditional-GAN model output;

FIG. 28B shows a confusion matrix comparing ILT regional classifications between generated images and ground truth segmentations derived from the Cycle-GAN model output;

FIG. 30 shows a flowchart;

FIG. 31 shows a flowchart; and

Throughout the description and the drawings, like reference numerals refer to like parts.

DETAILED DESCRIPTION

Figures 2A, 2B, 2C, 2D:
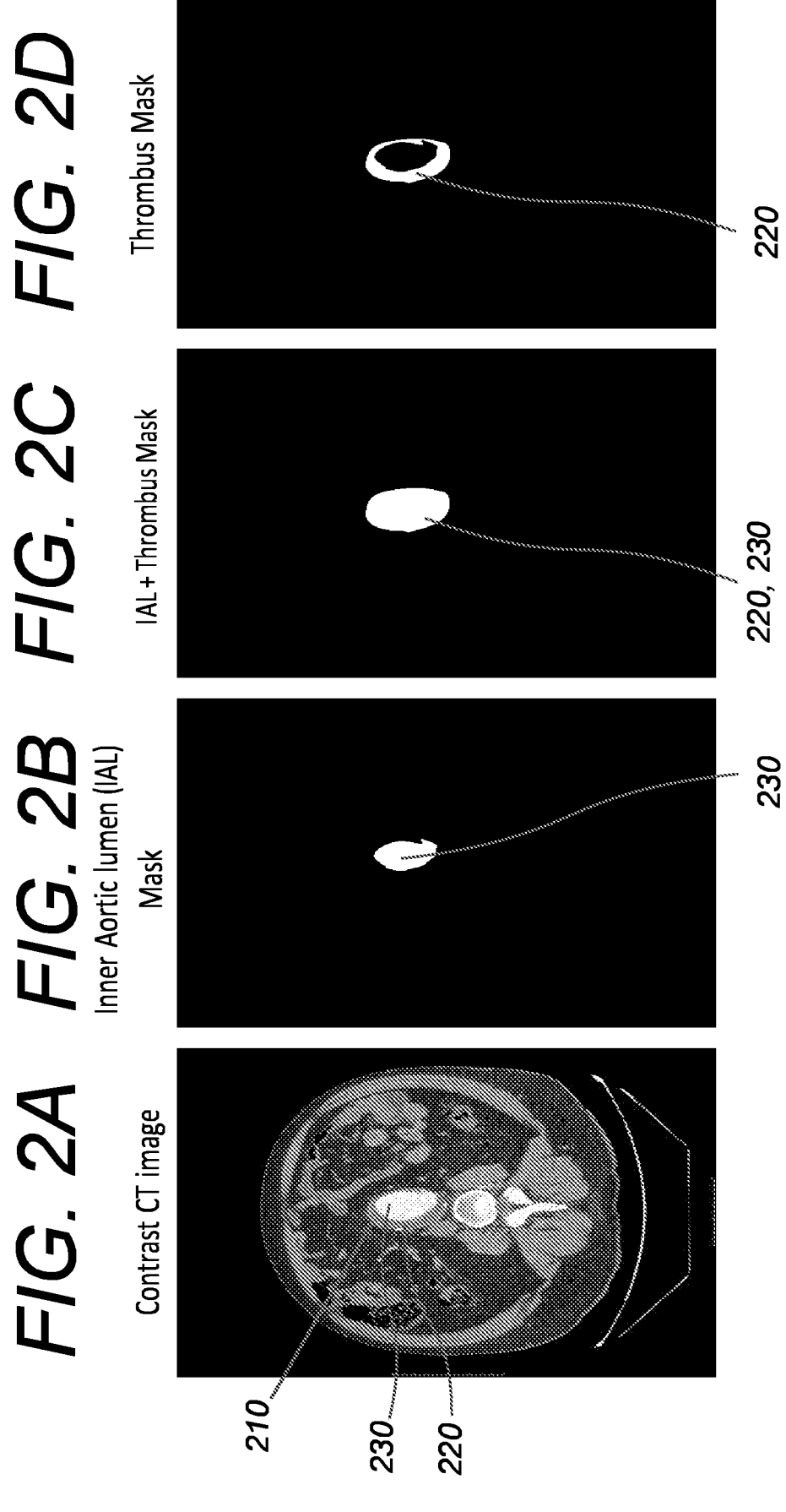
FIG. 2A shows a contrast CT image of an abdominal aortic region.
FIGS. 2B-2D show image masks obtained from the contrast CT image shown in FIG. 2A.

The present disclosure provides ways of training a machine learning algorithm, for example an image segmentation or random forest algorithm or a generative adversarial network (GAN), to identify anatomical structures, for example structural features of a blood vessel, in a non-contrast computed tomography (NCT) image, and further discloses methods for establishing a training set used to train the machine learning algorithm to identify such anatomical structures in an NCT image. The present disclosure further provides other ways of identifying structural features in an NCT image. Whilst various embodiments are described below, the invention is not limited to these embodiments, and variations of these embodiments may well fall within the scope of the invention which is to be limited only by the appended claims.

CT angiograms (CTAs) are widely used in all fields of cardiovascular surgery/medicine. When treatment of an artery, for example the aorta, is being considered, a medical/surgical professional usually requires a detailed view of the artery to differentiate the morphology/anatomy of the arterial structures. In the case of abdominal aortic aneurysms (AAAs), there is usually thrombus lining within the aneurysm sac. Full visualisation of the thrombus morphology, and its relation to the artery wall, is important for planning surgical intervention, for example by stenting or open repair.

Figures 1A, 1B:
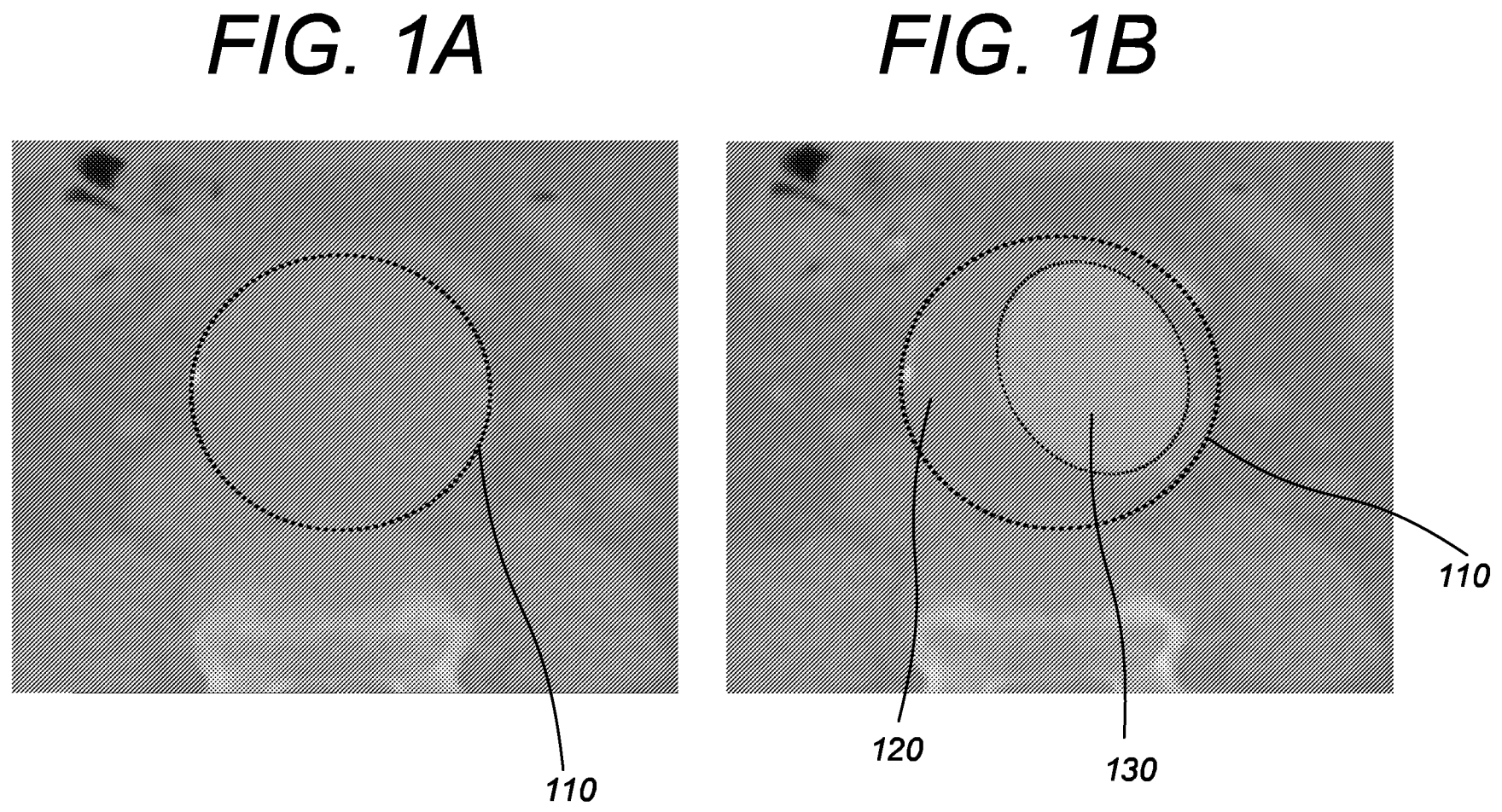

FIGS. 1A and 1B show axial slices of an abdominal aortic region obtained from a non-contrast CT scan and a contrast CT scan respectively. The aneurysm lies within region 110 of FIGS. 1A and 1B. As described above, to enable a surgeon or other medical professional to monitor the growth of the aneurysm and/or plan for surgery, full visualisation of the thrombus morphology, and its relation to the artery wall is important. The contrast CT image of FIG. 1B clearly shows the interface between the thrombus 120 and the aortic inner lumen 130. These structural features 120 and 130 of the targeted region 110 are very difficult to distinguish in the NCT image with the naked eye, as is apparent from viewing FIG. 1A.

The inventors have discovered that although the structural features 120 and 130 are difficult to distinguish using an NCT image, there is a difference in radiodensity between the subregions that is identifiable from information embedded in an NCT image. This information can be exploited by a machine learning algorithm to identify structural features such as 120 and 130 of a targeted region like 110. For example, blood, thrombus, and arterial walls are all made up of different substances and differ in their densities. Blood is predominantly fluid, whereas thrombus is predominantly fibrinous and collagenous, with red cells/platelets, and arterial walls are predominantly smooth muscle cells, with collagen. Although it is difficult for the human eye to detect the difference between these entities, the inventors have shown that due to the distinct nature of these entities, raw data obtained from an NCT image contains information which enables a machine learning algorithm to discern one from the other. This has the advantage of overcoming the problems described above associated with administering a patient with a contrast agent.

The inventors were able to determine that there is a difference in Hounsfield unit intensity between different structural features of a blood vessel embedded in an NCT image, by first manually segmenting structural features, such as the thrombus and the inner lumen, from a CCT image of an abdominal aortic region of a patient as discussed in relation to FIG. 2A-2D below.

The inventors were also able to show that due to the distinct nature of the structural features of a blood vessel, such as structural features 120 and 130, the radiomic signatures of these regions are distinct. The inventors were able to exploit the distinct radiomic signatures of the regions within a blood vessel and devised a method for training a machine learning algorithm, such as a random forest classification algorithm, to identify structural features of a blood vessel from a NCT image as discussed below. Even without the use of a machine learning algorithm, the radiomic features values may be used to identify structural features.

FIG. 2A shows an axial slice of an abdominal aortic region obtained from a CCT scan of a patient, and the image masks, FIG. 2B-2D, obtained from the CCT scan shown in FIG. 2A. The image masks shown in FIGS. 2B-2D are generated by manually segmenting the structural features 220 and 230 from the targeted region 210 of the CCT image based on an analysis of the Hounsfield units of the voxels in the CCT image. FIG. 2B shows the segmentation of the aortic inner lumen 230 from the targeted region 210. FIG. 2C shows the segmentation of both the aortic inner lumen 230 and the thrombus 220 from the targeted region 210. FIG. 2D shows the segmentation of solely the thrombus 220, which is obtained by subtracting the inner aortic mask, FIG. 2B, from the inner aortic and thrombus mask, FIG. 2C. The generated masks from the CCT image were then reoriented into the NCT image plane and were used to demarcate the boundary between the structural features in a corresponding NCT image, as discussed in relation to FIG. 3 below.

Figures 3A, 3B, 3C, 3D:
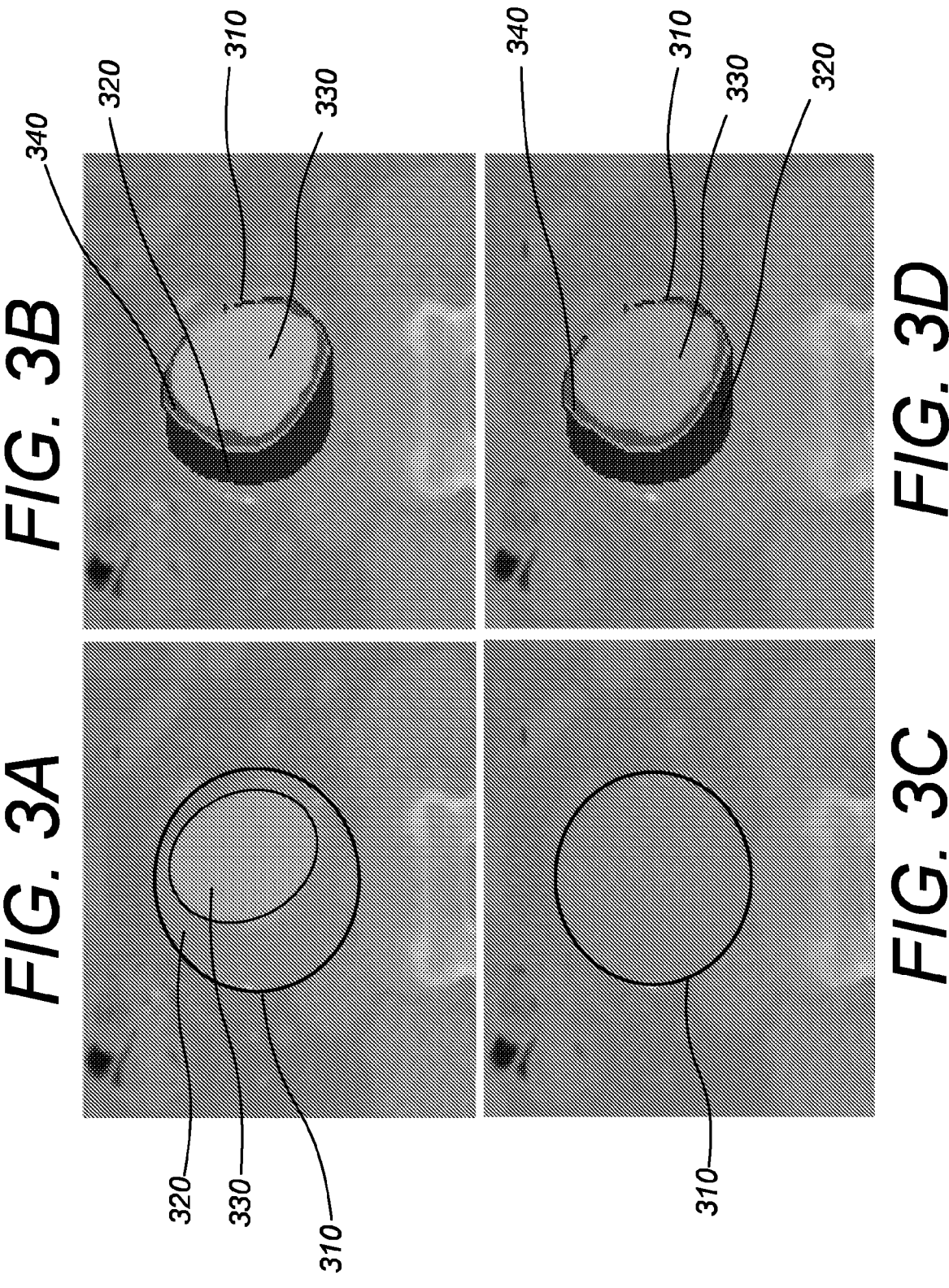
FIG. 3A shows a contrast CT image of an abdominal aortic region.
FIG. 3B shows a reoriented CT image of an abdominal aortic region with a mask demarcating subregions.
FIG. 3C shows a non-contrast CT image of an abdominal aortic region.
FIG. 3D shows a non-contrast CT image of an abdominal aortic region mapped with a mask demarcating subregions.

FIGS. 3A and 3C show axial slices of an abdominal aortic region of a patient obtained from a CCT scan and an NCT scan, respectively, as previously shown in FIGS. 1A and 1B. FIGS. 3B and 3D show the CCT image and the NCT image, respectively, with segmentation masks demarcating the boundaries between structural features of the targeted region 310. The demarcated regions display the thrombus 320, the inner aortic lumen 330 and the interface between the regions 340. The CCT image and the generated masks have been rescaled and/or reshaped and/or reoriented into the NCT image plane to account for voluntary and involuntary movements by the patient between the CCT scan and the NCT scan. As shown in FIG. 3D, the reoriented masks demarcate in the NCT image a boundary between the structural features, 320, 330, and 340 of the targeted region 310.

Figure 4:
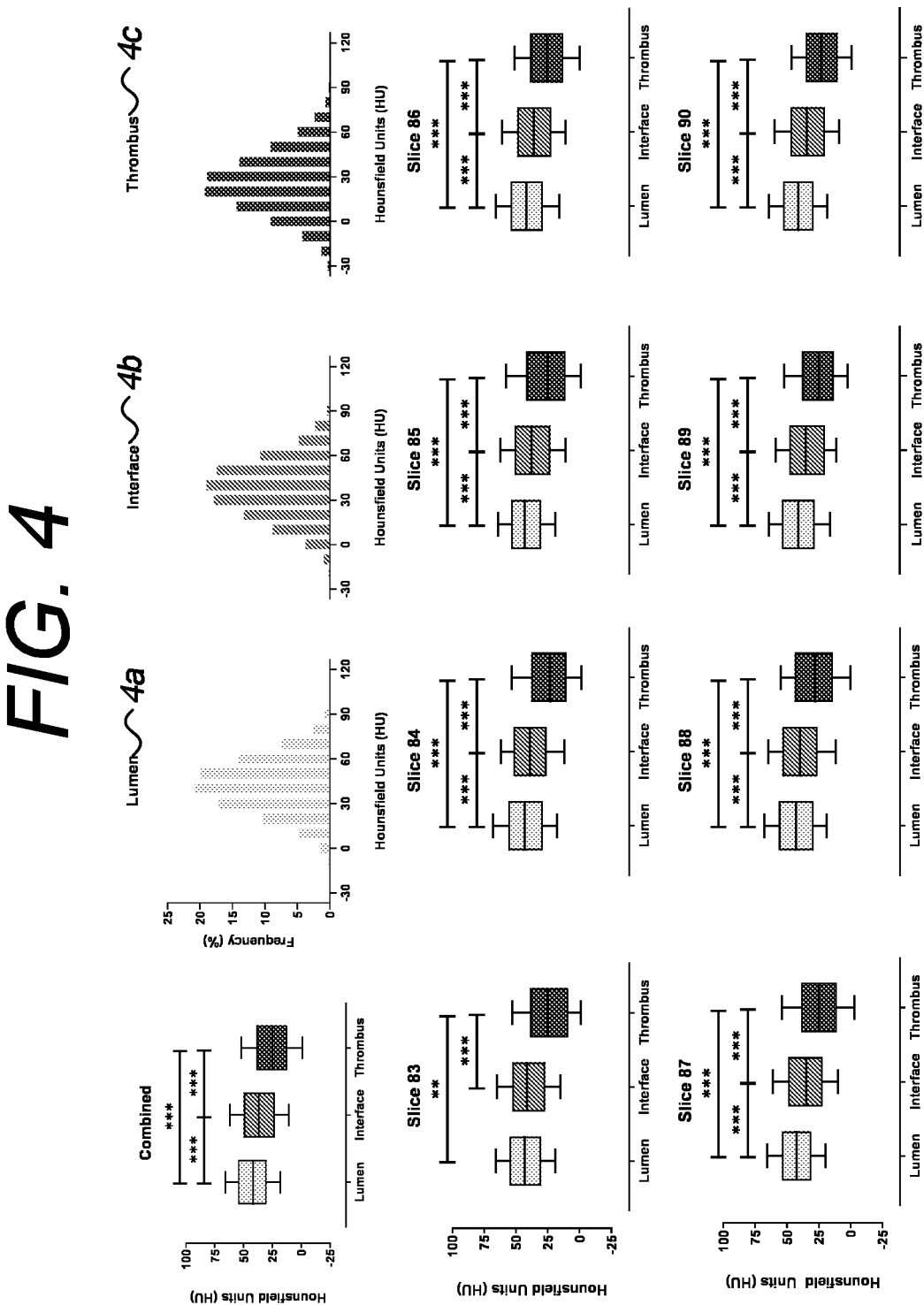
FIG. 4 illustrates the differences in Hounsfield unit intensity between several structural features of blood vessels for 8 axial slices obtained from NCT scans of a patient.

Once the boundary between the structural features was determined, the inventors were able to compare the Hounsfield unit intensity of the different structural features 320, 330, and 340 of the NCT image. FIG. 4 illustrates the differences in Hounsfield unit intensity between the structural features 320, 330, and 340 for 8 axial slices, slice 83, slice 84, slice 85, slice 86, slice 87, slice 88, slice 89, and slice 90 obtained from NCT scans of a patient. It can be seen that the average Hounsfield unit intensity for the thrombus was significantly lower when compared to that of the lumen for all axial slices sampled. Furthermore, the interface was also significantly different from the other two regions, indicating a gradual change in pixel intensity from the centre lumen to the peripheral thrombus. FIG. 4 also shows histograms, 4a, 4b, and 4c. Histograms corresponding to the Hounsfield unit frequencies for each region had considerable overlap, however a slight difference in spread can be noted. In this patient, a greater proportion of the lower/negative intensity Hounsfield units were observed within the thrombus. Given that the difference in Hounsfield units between the lumen and thrombus spans only a few Hounsfield units and is nearly impossible to differentiate by the unaided clinical observer, this analysis shows for the first time that there is information relating to Hounsfield units embedded in a non-contrast CT image which can be exploited by a machine learning image segmentation algorithm to identify structural features of a blood vessel in a non-contrast CT image.

A method for establishing a labelled training set for training a machine learning image segmentation algorithm or a classification algorithm (such as a random forest) to identify structural features of a blood vessel in an NCT image will now be described in relation to the flowchart shown in FIG. 5. The method may be performed by any suitable computing apparatus, such as the computing apparatus 600 described in relation to FIG. 6 below. The method may be stored in machine/computer-readable form on a machine-readable/computer-readable medium, such as machine readable medium 3300 described in relation to FIG. 33. The labelled training set may be stored in machine/computer-readable form on a machine-readable/computer-readable medium, such as machine readable medium 3300 described in relation to FIG. 33.

At 510, the method comprises receiving a plurality of NCT images, each NCT image showing a targeted region of a subject, such as the targeted region 110 shown in FIG. 1A where the targeted region comprises the abdominal aorta.

At 520, the method comprises receiving a plurality of CCT images, where each CCT image corresponds to an NCT image of the plurality of NCT images and shows the corresponding targeted region of the subject.

At 530, the method comprises adapting the plurality of CCT images to substantially align with the corresponding NCT images, where adapting the plurality of CCT images comprises orienting and scaling the plurality of CCT images to substantially align with the corresponding NCT images.

At 540, the method comprises segmenting the plurality of adapted CCT images to generate a corresponding plurality of segmentation masks, where each segmentation mask labels at least one structural feature of the at least one blood vessel of the targeted region in the corresponding adapted CCT image.

At 550, a labelled training set is established, wherein the labelled training set includes pairs of NCT images and segmentation masks, where each pair comprises a segmentation mask and the NCT image to which the adapted CCT image substantially aligns.

Figure 6:
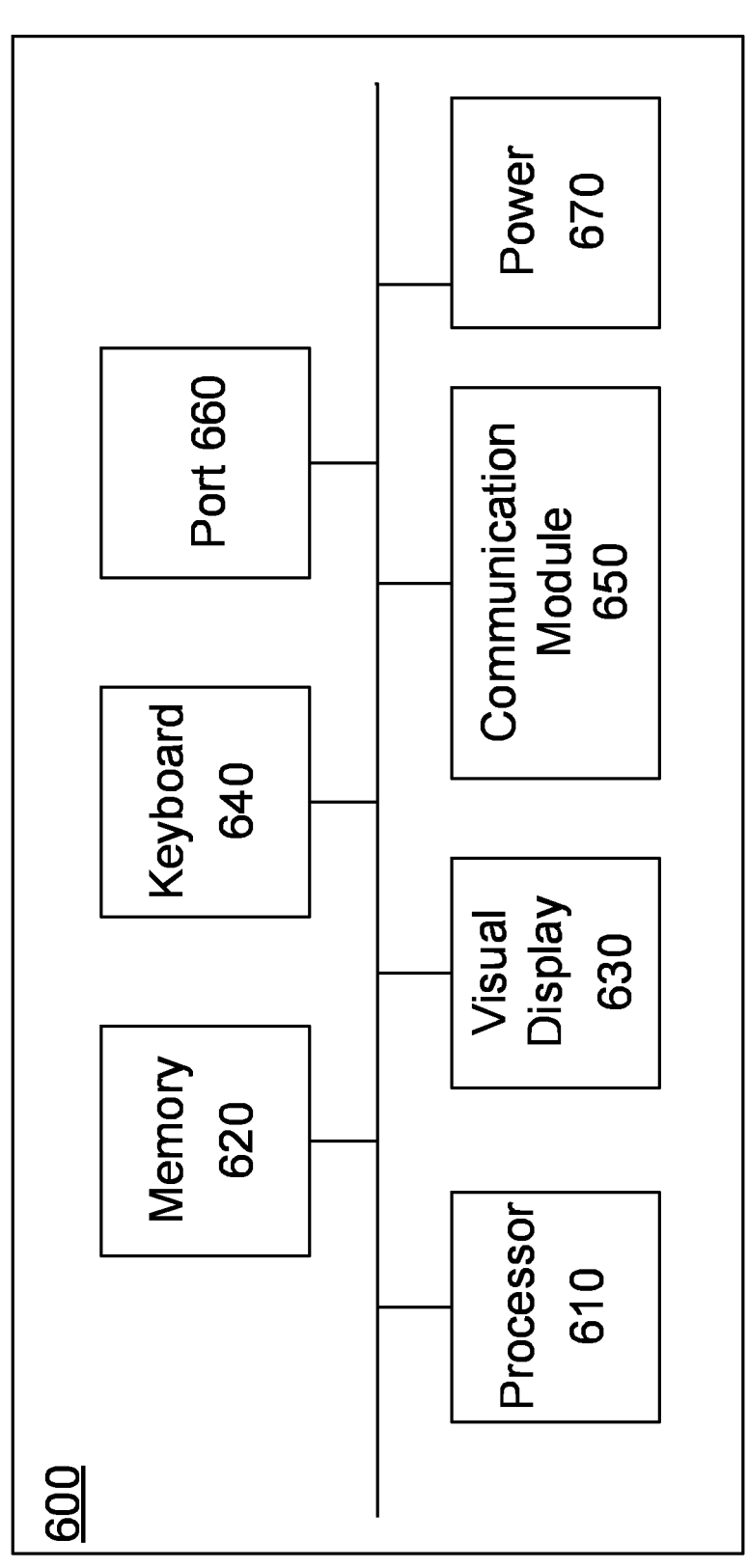
FIG. 6 shows a block diagram of a computing apparatus.

The method for establishing a labelled training set used to train a machine learning image segmentation algorithm or a classification algorithm, as described in FIG. 5, is suitable for performance by a computing apparatus such as computing apparatus 600 as shown in FIG. 6 and described below.

Computing apparatus 600 may comprise a computing device, a server, a mobile or portable computer and so on. Computing apparatus 600 may be distributed across multiple connected devices. Other architectures to that shown in FIG. 6 may be used as will be appreciated by the skilled person.

Referring to FIG. 6, computing apparatus 600 includes one or more processors 610, one or more memories 620, a number of optional user interfaces such as visual display 630 and virtual or physical keyboard 640, a communications module 650, and optionally a port 660 and optionally a power source 670. Each of components 610, 620, 630, 640, 650, 660, and 670 are interconnected using various busses. Processor 610 can process instructions for execution within the computing apparatus 600, including instructions stored in memory 620, received via communications module 650, or via port 660.

Memory 620 is for storing data within computing apparatus 600. The one or more memories 620 may include a volatile memory unit or units. The one or more memories may include a non-volatile memory unit or units. The one or more memories 620 may also be another form of computer-readable medium, such as a magnetic or optical disk. One or more memories 620 may provide mass storage for the computing apparatus 600. Instructions for performing a method as described herein may be stored within the one or more memories 620.

The apparatus 600 includes a number of user interfaces including visualising means such as a visual display 630 and a virtual or dedicated user input device such as keyboard 640.

The communications module 650 is suitable for sending and receiving communications between processor 610 and remote systems.

The port 660 is suitable for receiving, for example, a non-transitory computer readable medium containing one or more instructions to be processed by the processor 610.

The processor 610 is configured to receive data, access the memory 620, and to act upon instructions received either from said memory 620 or a computer-readable storage medium connected to port 660, from communications module 650 or from user input device 640.

The computing apparatus 600 may receive, via the communications module 650, data representative of a plurality of non-contrast CT scans of a targeted region of a subject and data representative of a plurality of contrast CT scans of a targeted region of a subject. The data received via the communications module 650 relating to a non-contrast CT scan may be received prior to or subsequent to a contrast CT scan, and may comprise information relating to the measured intensity of the x-rays impinging the targeted region of the subject. The processor 610 may be configured to follow instructions stored in one or more memories 620 to use the received data to reconstruct the corresponding non-contrast and contrast CT images using various CT reconstruction techniques. Each CCT image that is reconstructed corresponds to a reconstructed NCT image of the plurality of reconstructed NCT images.

Processer 610 may be configured to follow instructions stored in the memory 620 to adapt the plurality of CCT images by orienting and scaling the plurality of CCT images to substantially align with the corresponding NCT images.

The processor 610 may be configured to follow further instructions stored in the memory 620 to segment the plurality of adapted CCT images to generate a corresponding plurality of segmentation masks, each segmentation mask labelling at least one structural feature of the at least one blood vessel of the targeted region in the corresponding adapted CCT image. The reconstructed CCT image comprises voxels/pixels, and the generated plurality of segmentation masks may be binary segmentation masks, where the voxels/pixels comprising structural feature of the blood vessel of the targeted region may be labelled with a 1 and the voxels/pixels comprising features in the image which are not structural features of the blood vessel may be labelled with a 0 (for example).

The processor 610 may be configured to follow instructions stored in the memory 620 to pair a generated segmentation mask with a corresponding NCT image to which the adapted CCT image substantially aligns.

Based on the above description, computing apparatus 600 can be used to establish a labelled training set for training a machine learning image segmentation algorithm or a classification algorithm, where the established labelled training set includes information relating to pairs of NCT images and segmentation masks, where each pair comprises a segmentation mask and the NCT image to which the corresponding adapted CCT image substantially aligns. The skilled person would appreciate that other architectures to that shown in FIG. 6 may be used.

Figure 7:
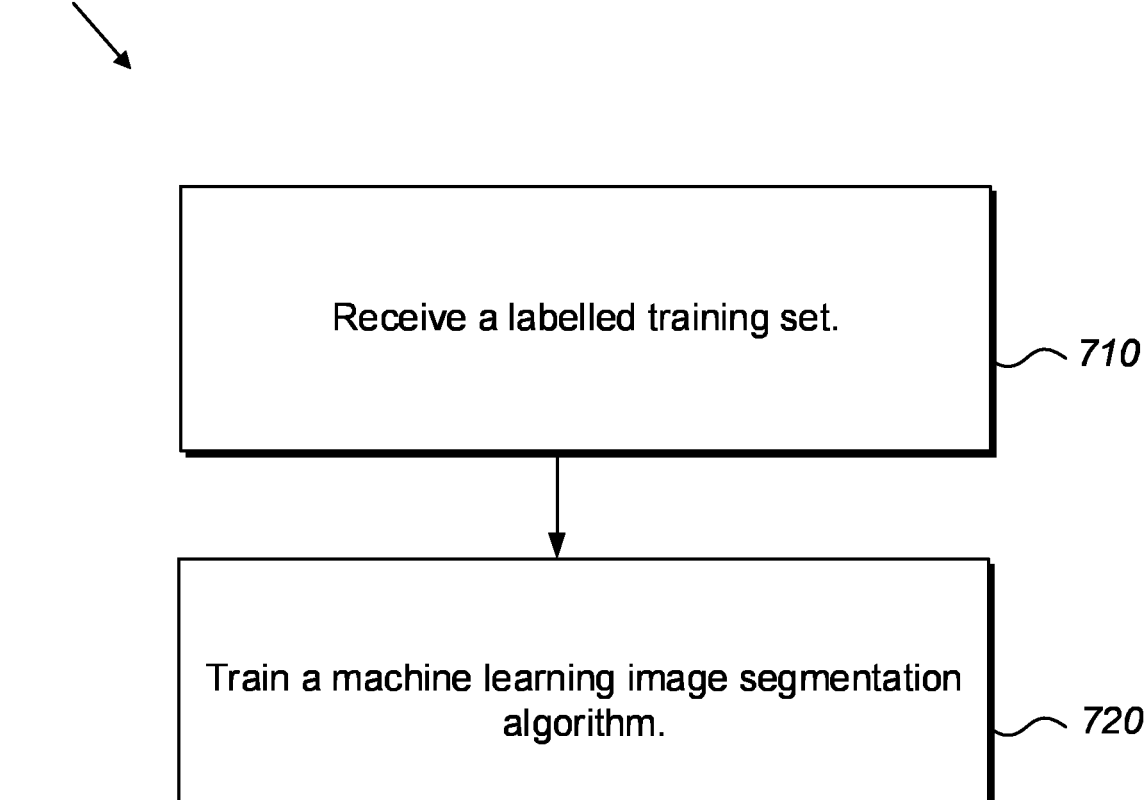
FIG. 7 shows a flowchart.

FIG. 7 shows a flowchart of a method for training a machine learning image segmentation algorithm, using a training set such as that described above in relation to FIG. 5, to identify structural features of a blood vessel in an NCT image.

At step 710, the method comprises receiving a labelled training set, such as the labelled training set described above in relation to FIG. 5. The labelled training set comprises information relating to a plurality of NCT images, where each NCT image of the plurality of NCT images shows a targeted region of a subject which includes at least one blood vessel. The training set further comprises a corresponding plurality of segmentation masks, where the segmentation masks are generated from a CCT image corresponding to an NCT image of the plurality of NCT images and each segmentation mask labels at least one structural feature of a blood vessel in a corresponding NCT image of the plurality of NCT images.

At step 720, the method comprises training a machine learning segmentation algorithm using the plurality of NCT images and the corresponding plurality of segmentation masks, to learn features of the NCT images that correspond to structural features of the blood vessels labelled in the segmentation masks.

At step 730, the method comprises output of a trained image segmentation model usable for identifying structural features of a blood vessel in an NCT image.

The method for training a machine learning image segmentation algorithm, as described above in relation to FIG. 7, is suitable for performance by a computing apparatus such as computing apparatus 600 as shown in FIG. 6.

The processor 610 may be configured to train a machine learning image segmentation algorithm to learn the features of NCT images that correspond to structural features of blood vessels of the targeted region using the plurality of NCT images and the corresponding plurality of segmentation masks. For each NCT image and the corresponding segmentation mask, the processor 610 may follow instructions stored in one or more memories 620 to compare the segmentation mask with the corresponding NCT image and adjust the internal weights of the image segmentation algorithm via backpropagation. Several iterations of the comparison between the NCT image and the corresponding segmentation mask may be performed for each NCT image from the plurality of NCT images and the corresponding segmentation masks until a substantially optimized setting for the internal weights is achieved. The processor 610 may follow further instructions stored in one or more memories 620 to perform image transformations at each iteration for each NCT image of the plurality of NCT images to diversify the input data set and maximise learning.

The processor 610 may be configured to follow further instructions to output the trained image segmentation model and store the trained image segmentation model in one or more memories 620. The trained image segmentation model may comprise for example the weights and biases established during training, along with any selected hyperparameters such as minibatch size or learning rate.

FIG. 8 shows a flowchart of a method for identifying structural features of a blood vessel in an unlabelled NCT image.

At step 810, the method comprises providing the NCT image to a trained image segmentation model which may be trained according to the method described above in relation to FIG. 7. The trained image segmentation model is trained to learn features of NCT images that correspond to structural features such as the thrombus 320 and/or the lumen 330 of a blood vessel.

At step 820, the method comprises generating, using the trained image segmentation model, predicted segmentation data for the provided NCT image. The predicted segmentation data identifies features of the blood vessel in the provided NCT image.

The method for identifying structural features of a blood vessel in an unlabelled NCT image, as described above in relation to FIG. 8, is suitable for performance by a computing apparatus such as computing apparatus 600 as shown in FIG. 6.

The computing apparatus 600 may receive, via the communications module 650, data from an NCT scan of a subject. The received data may comprise information relating to the measured intensity of the x-rays impinging the targeted region of the subject.

The computing apparatus 600 may store a trained image segmentation model in one or more memories 620 of the computing apparatus 600, where the trained image segmentation model is trained to learn features of NCT images that correspond to structural features of blood vessels of a targeted region. The processor 610 may be configured to input the received data from the NCT scan to the trained image segmentation model.

The processor 610 may follow further instructions stored in memory 620 of the computing apparatus 600 to generate, using the trained image segmentation model, a predicted segmentation mask for the provided NCT image. The predicted segmentation mask identifies the structural features of the at least one blood vessel in a targeted region of the provided NCT image.

Figure 9:
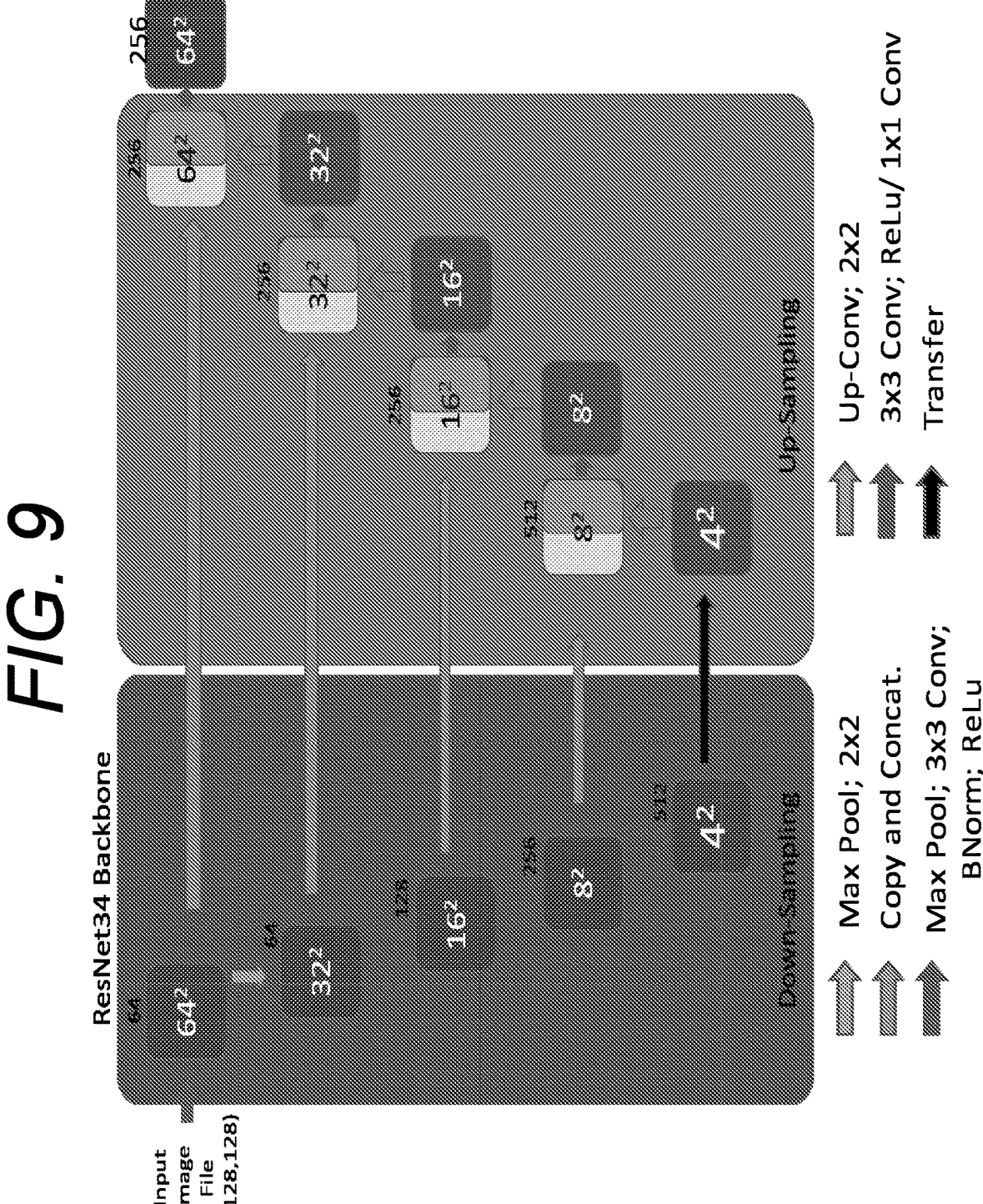
FIG. 9 illustrates an example machine learning image segmentation algorithm.
Figure 10:
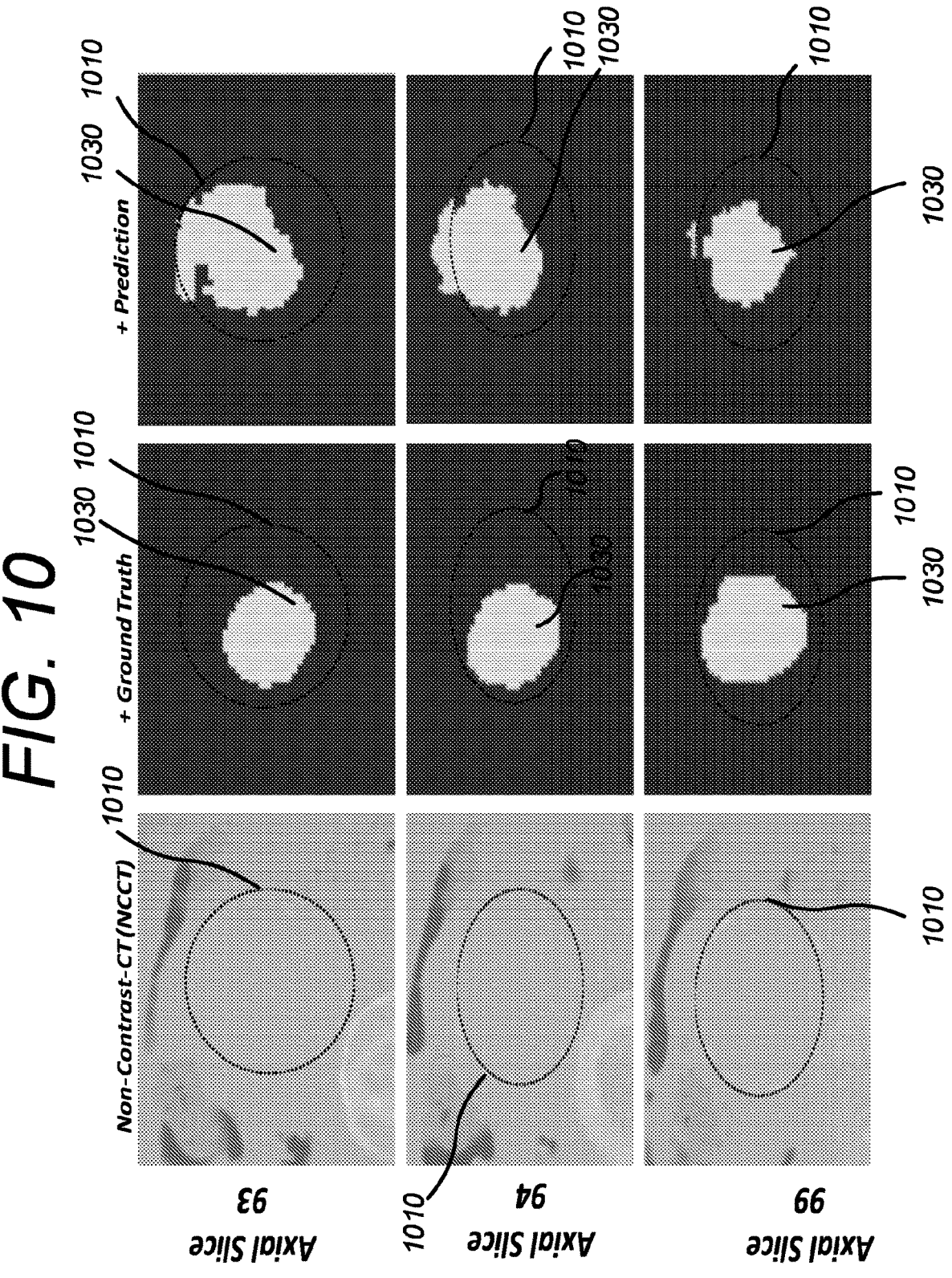
FIG. 10 shows predicted segmentation masks of a non-contrast CT image obtained using a trained machine learning image segmentation algorithm.

FIGS. 9 and 10 illustrate a machine learning image segmentation algorithm and the corresponding output of test data. The algorithm utilises deep learning and is based on a modified U-NET architecture. U-NET is very good for biomedical image segmentation tasks.

The general U-NET architecture used for the experiment comprises two components: a downsampling/contraction path (as shown on the left in FIG. 9) and an upsampling/expanding path (as shown on the right in FIG. 9). The contraction path serves to extract information and capture the context of the image at the expense of losing spatial information. This is achieved through a series of algebraic manipulations (convolutions and max-pooling/averaging) as shown in FIG. 9. During this iterative step, the size of the input image is gradually reduced from 256×256×3 to 4×4× 512. This is followed by an expansion path, where the size of the image gradually increases from 4×4×512 to 256× 256×1 to produce a predictive binary segmentation mask. This is accomplished using similar algebraic methods. The lost spatial information is restored using skip connections that connect the output of the down-sampling path with the feature maps/input of the up-sampling path at the same level. After each skip connection, two consecutive convolutions are used to integrate the spatial and contextual information to assemble a more precise output.

The inventors sought to use a modified version of this established U-NET to predict aneurysmal components from a non-contrast CT scan. The architecture used in this experiment is illustrated clearly in FIG. 9. The down-sampling path was a pre-trained residual network (in particular a ResNET-34 model), which had been pre-trained on a large visual database of over 14 million images. The training of neural networks (ex. ResNet50) on large and diverse image databases (ex. ImageNet) has expedited training and resulted in higher predictive accuracies in other classification problems. While the pre-training images were not biomedical in nature, they served to teach the model to understand important features common to most images (corners, edges, shapes etc.). The model was then trained and tested over multiple iterations to achieve a particular task, in this case to segment to aortic inner lumen from the non-contrast CT images.

By training the model on the ImageNet database, the inventors sought to first teach the algorithm to classify the aorta from surrounding structures, and then to extend its performance to aortic segmentation.

Each axial CT slice and their respective image masks/segmentation masks were augmented through image transformations (shear, divergence) to diversify the input data set and maximize learning. The initial learning rate and weight decay was set to $4.0 \times 10^{-2}$ and $1.0 \times 10^{-7}$, respectively. The first training loop included a batch size of 25 images and was trained for a total of 16 cycles. Subsequently, the earlier pre-trained layers, which have learned to identify features common to all images (ex. edges, corners, shapes, etc.) were fine-tuned using differential learning rates for an additional 10 cycles. During the training paradigm, the DICE score metric, which reflects the similarity of the inner mask prediction to the ground truth inner mask, increased from 8.6% to approximately 69%.

FIG. 10 shows the "ground truth" adjacent to the trained model's prediction. This suggests that this neural network can discern the location of the inner lumen. Further training is being undertaken to improve performance.

FIG. 10 in particular shows predictions of the location of the inner aortic lumen 1030 in a region of interest 1010 for three non-contrast axial slices 93, 94 and 99 as output from a trained segmentation model. The non-contrast CT column shows three non-contrast CT axial slices 93, 94 and 99 of the abdominal aortic region of a patient. The trained model received the 3 non-contrast CT axial slices 93, 94 and 99 as input data and was able to output predictions of the inner aortic lumen for each axial slice, as shown in the "prediction" column. The predicted output when compared to the ground truth (that is, to a segmented contrast CT image) for each axial slice shows that the model can discern the location of the inner aortic lumen 1030.

Figure 11:
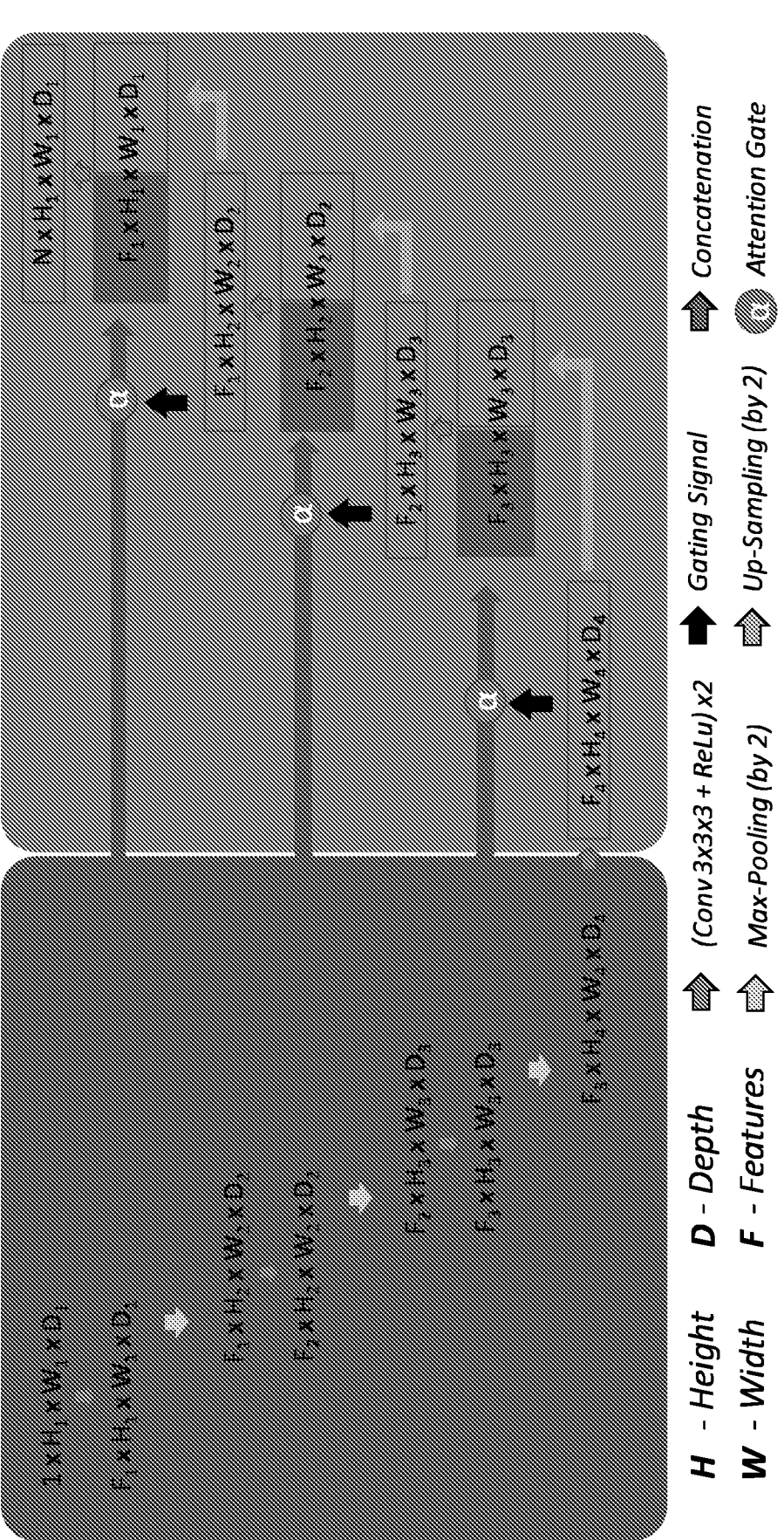
FIG. 11 shows another example machine learning image segmentation algorithm.

FIG. 11 illustrates a machine learning image segmentation algorithm. The algorithm utilises deep learning and is based on a modified U-NET architecture that uses attention gating. Attention gates are used to focus on target structures without the need for additional training/supervision. The attention gates filter along both the forward and backward directions. Gradients originating from the background regions are down-weighted during the backward pass allowing model parameters to be updated mostly based on spatial regions relevant to the given task. Accordingly, the attention gates reduce the need for hard attention/external organ localisation (region-of-interest) models in image segmentation frameworks.

Figure 12:
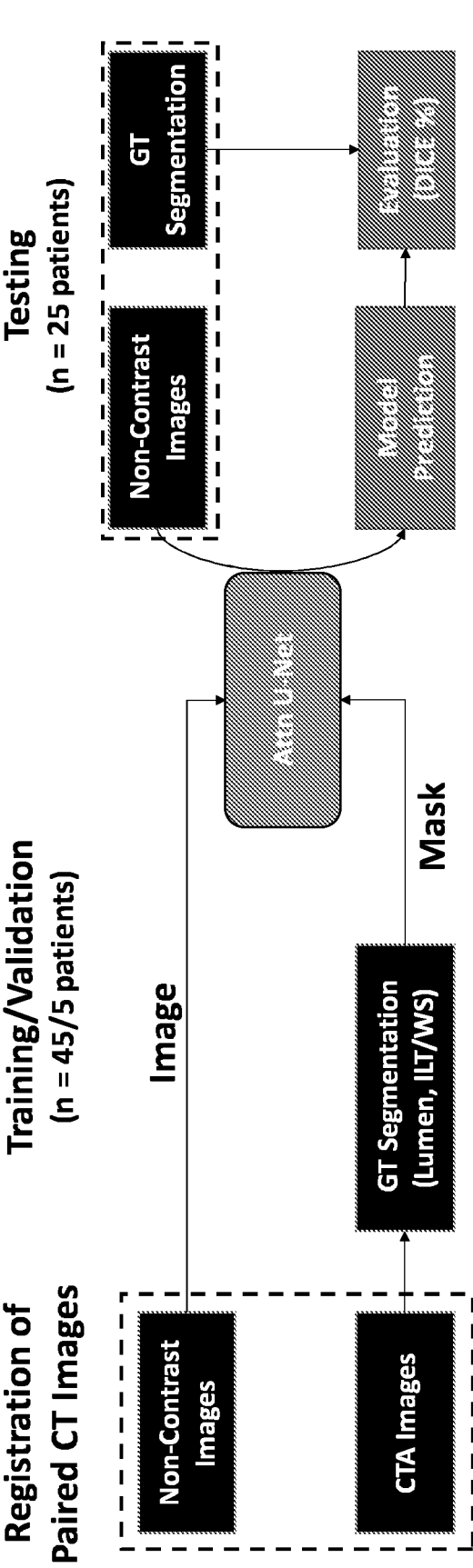
FIG. 12 illustrates a methodology of an experiment performed to investigate whether deep learning image segmentation methods can be used to define and extract the subtle differences between the various components of the soft tissue (inner lumen and intra-lumen thrombus (ILT) regions) directly from NCT images.
Figure 13:
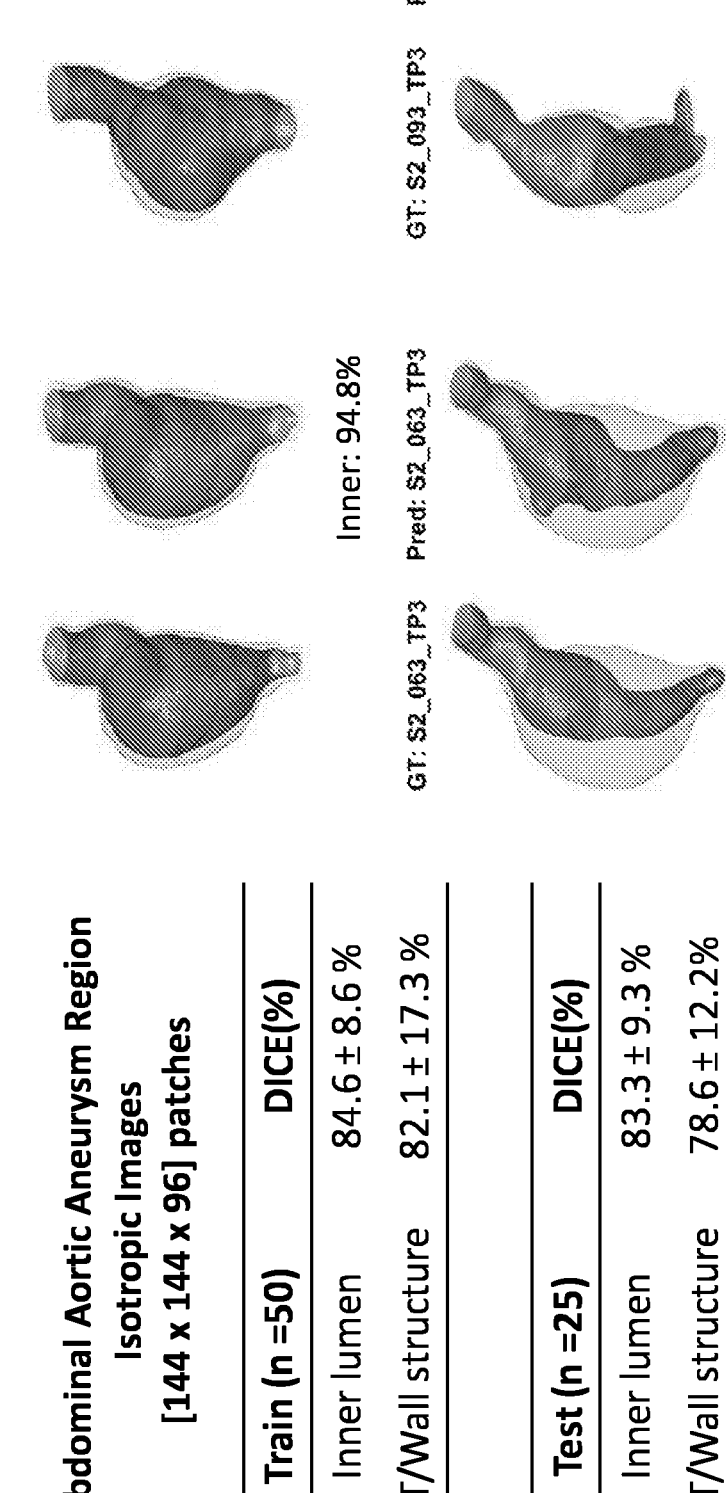
FIG. 13 shows the DICE accuracy for inner and outer lumen reconstruction from NCT images and further shows visualisations of the overlap of volumes of inner and outer lumen.

An experiment was performed to further investigate whether deep learning segmentation methods can be used to define and extract the subtle differences between the various components of the soft tissue (inner lumen and intra-lumen thrombus (ILT)/WS regions) directly from NCT images. The methodology is illustrated in FIG. 12. Paired Non-contrast CT and contrast CT images (obtained during the same visit) were paired using a rigid registration algorithm. In this case, the CCT images came from a CT angiogram (CTA). The registered NCT and CCT images were segmented using an automatic deep learning segmentation algorithm. The training data for this attention-based U-Net (labelled as Attn U-Net in FIG. 12) were NCT images and the multi-label segmentation masks (labelled as ground truth GT Segmentation in FIG. 12) generated from the CCT images (n=50; 45 for training and 5 for validation). The algorithm was trained for a total of 2000 epochs (Learning Rate=1.0×10⁻⁴, Batch Size=2). The trained model was evaluated on a set of 25 patients. The model predictions of these 25 patients were compared against the GT segmentations. The DICE accuracy for the inner lumen reconstruction from NCT images was approximately 84% (see FIG. 13). Model predictions and the corresponding DICE scores of inner lumen for four patients within the testing cohort are displayed in FIG. 13 alongside the GT segmentations and display considerable concordance.

Figure 14:
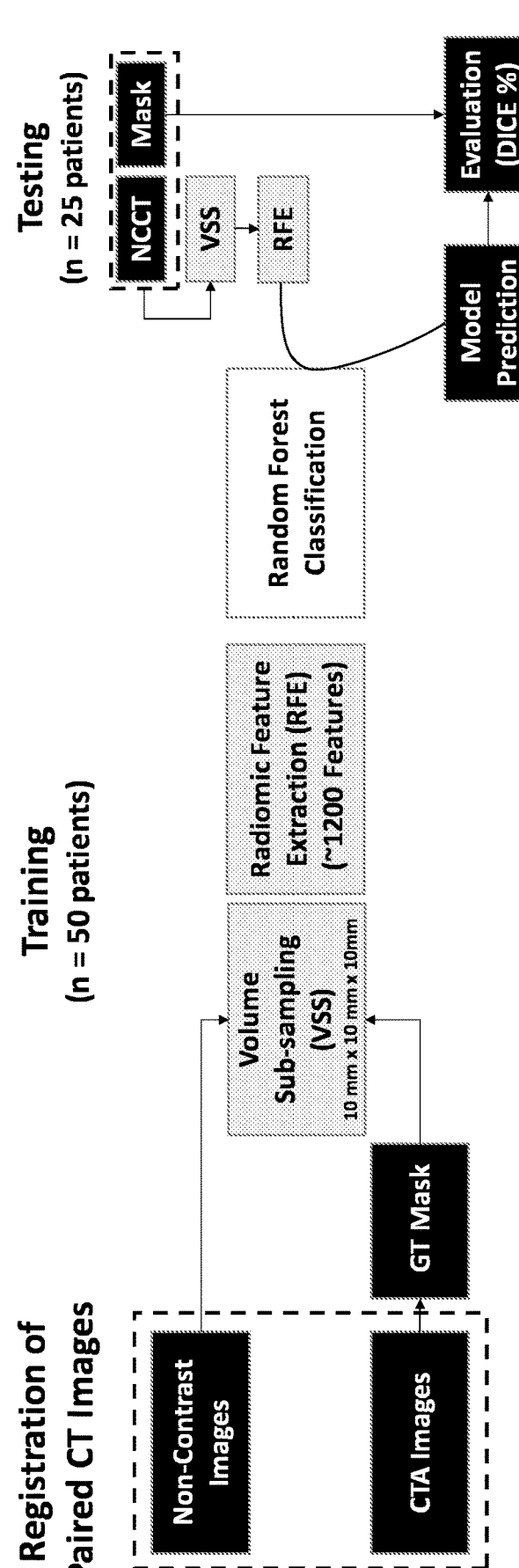
FIG. 14 illustrates a methodology for investigating whether random forest classification algorithms can be used to define and extract the subtle differences between the various components of the soft tissue (inner lumen and intra-lumen thrombus (ILT)/WS regions) directly from NCT images.

The above discussion illustrates that a machine learning image segmentation algorithm can be used to identify structural features in an NCT image. There is accordingly enough information in an NCT image to be able to identify structural features of a blood vessel. With this in mind, the inventors hypothesised that, given the different biochemical properties of blood within the lumen and intra-lumen thrombus, the radiomic features of these regions are distinct. This hypothesis was tested, and the methodology is illustrated in FIG. 14. Paired NCT and CCT images (obtained during the same visit) were paired using a registration algorithm. The registered NCT and CCT images were segmented using an automatic deep learning segmentation algorithm. Non-contrast CT image and segmentation volumes were divided into sub-volumes (VSS) of size 1 cm×1 cm×1 cm with a stride of 5 mm. 1200 radiomic features were extracted from the sub-volumes using the pyradiomics python package. The training data (50 patients) for this random forest classification algorithm consisted of the radiomic features for each sub-volume and the classification of that sub-volume (Thrombus/ILT-0, Lumen-1). The trained classification model was evaluated on a set of 25 patients. The model predictions of these 25 patients were compared against the ground truth (GT) segmentations.

The inventors devised two experiments to show how manual classification of radiomic features can be used to differentiate visually indistinct regions on non-contrast CT images. The two experiments and their results referenced herein as experiments 1 and 2 will be described below.

In the first experiment (experiment 1), the methodology of FIG. 14 was followed, and the sub-volumes that were sampled were entirely within the lumen and ILT segmentation masks. Sub-volumes at the interface between the two regions were excluded. This experiment aimed to investigate if there is a difference in radiomic signature between these two regions.

The table in FIG. 15A shows the number of sub-volumes sampled in relation to the inner lumen and thrombus for the training/validation cohort which consisted of 50 patients (n=50) and the number of sub-volumes sampled in relation to the inner lumen and thrombus region for the testing cohort which consisted of a set of 25 (n=25) patients not presented during model training and validation. FIG. 15A also shows the receiver operating characteristic curve (ROC) for the model in relation to the validation cohort. The ROC suggests that this classification model is able to differentiate between the two regions.

FIG. 15B indicates the accuracy of the random forest classification model at predicting the thrombus and the inner lumen regions in a NCT image on the testing cohort used for experiment 1. The confusion matrix in FIG. 15B shows that the random forest classification model accurately determined the thrombus at a rate of 83.3% and the inner lumen at a rate of 90.4%. The results on the testing cohort, which consisted of a set of 25 patients not presented during model training and validation, suggest that this classification model is not only able to differentiate between the two regions but is also robust.

Figure 16:
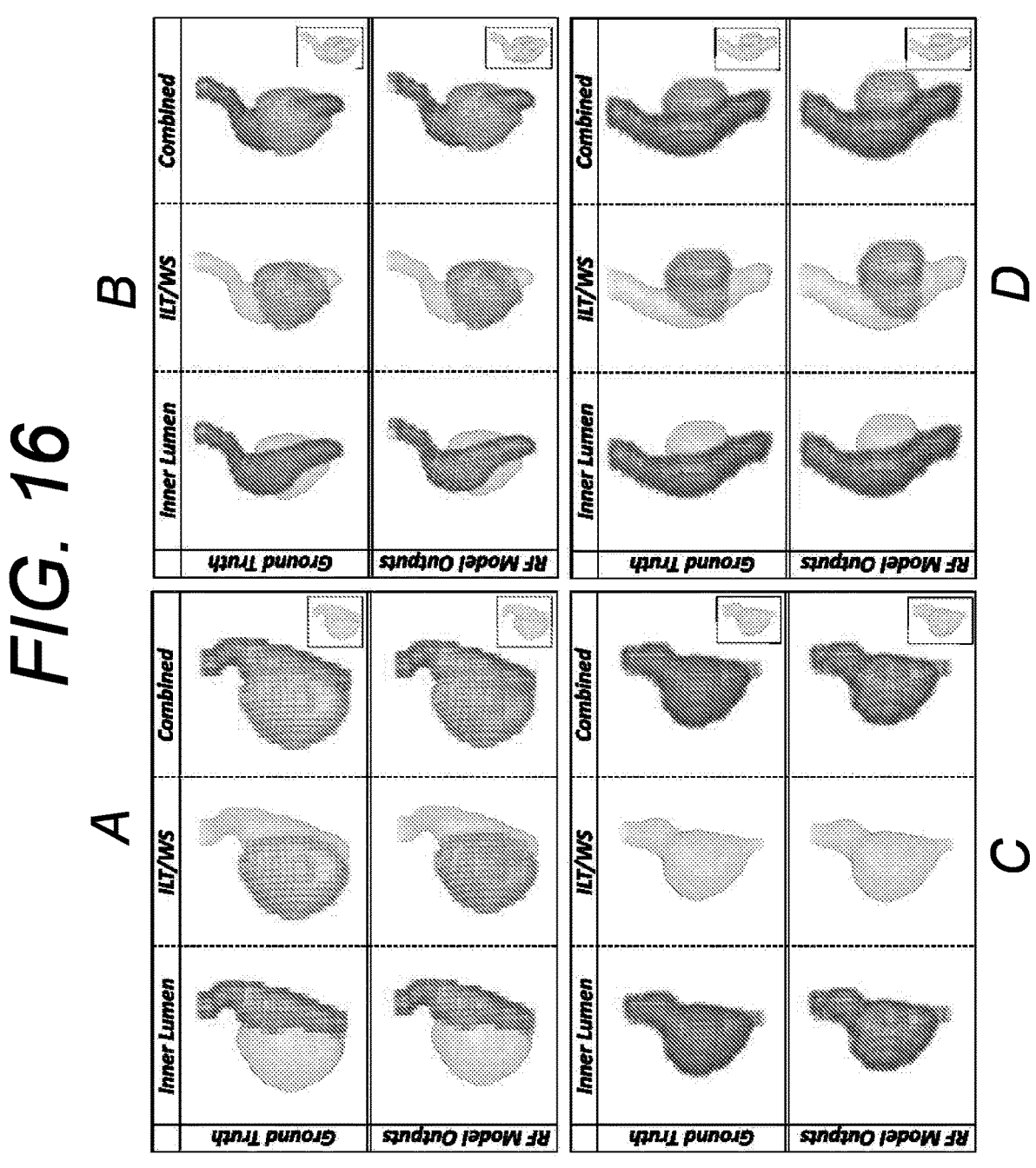
FIG. 16 shows a visualisation of the classification outputs of the first experiment (Experiment 1)

FIG. 16 shows a 3D reconstruction of structural features within an aneurysmal region of NCT images obtained from 4 different patients (A-D) of the above mentioned testing cohort of 25 patients. For each patient A-D, FIG. 16 shows the ground truth in relation to the inner lumen, the interluminal thrombus (ILT), and a combination of the inner lumen and wall structure/ILT in the top row and the outputs from a random forest classification algorithm of the inner lumen, the inter-luminal thrombus (ILT), and a combination of the inner lumen and ILT in the bottom row. The results provide support for the hypothesis that the radiomic signatures of the lumen and thrombus can be used to differentiate visually indistinct regions on non-contrast CT images.

Next, in Experiment 2 the inventors increased the size of the testing data set and modified the sub-sampling parameters. Once again, the methodology of FIG. 14 was used. Experiment 2 involved training a random forest classifier on all sub-volumes within the aorta from NCT images. Sub-volumes were classified as either inner lumen or wall structure/TLT based on the volume of each region (Lumen/wall structure) within each sub-volume. Sub-volumes at the interface between the two regions were excluded. This experiment aimed to investigate if the different regions as well as the thrombus-lumen interface can be extracted from a NCT image.

Figures 17A, 17B:
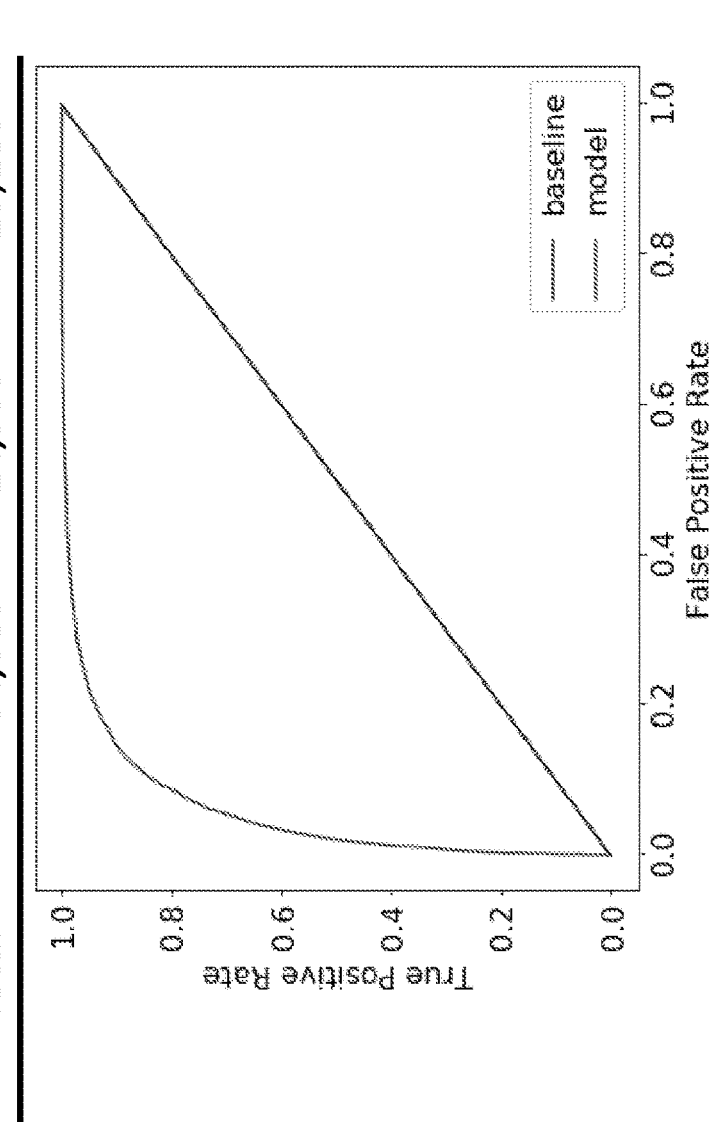
FIG. 17A shows a table summarising the number of volume subsamples taken for a second experiment (Experiment 2) as part of a first fold using the methodology of FIG. 14.
FIG. 17B shows an ROC curve for the first fold of Experiment 2.
Figures 17C, 17D:
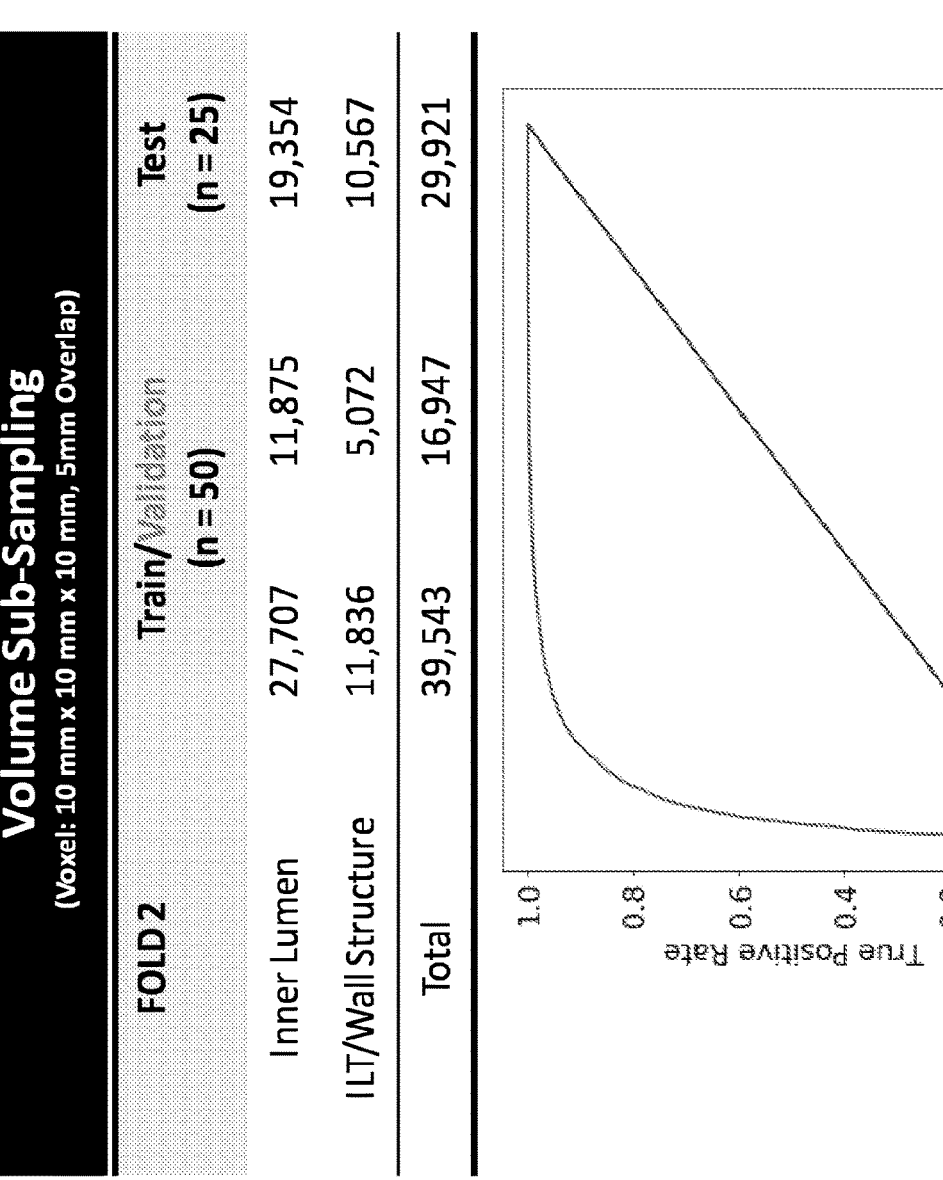
FIG. 17C shows a table summarising the number of volume subsamples taken for a second experiment (Experiment 2) as part of a second fold using the methodology of FIG. 14.
FIG. 17D shows an ROC curve for the second fold of Experiment 2.
Figures 17E, 17F:
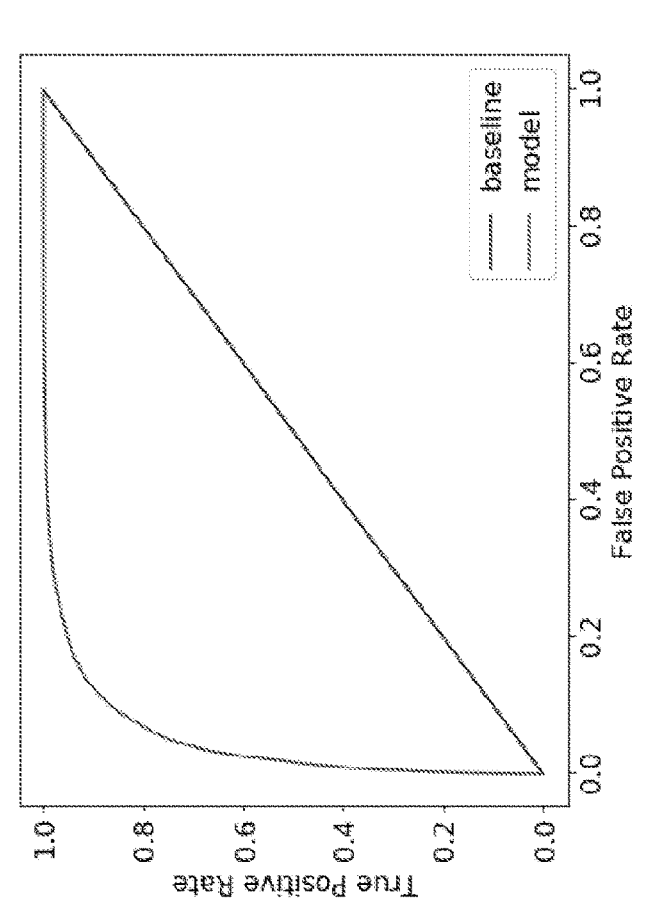
FIG. 17E shows a table summarising the number of volume subsamples taken for a second experiment (Experiment 2) as part of a third fold using the methodology of FIG. 14.
FIG. 17F shows an ROC curve for the third fold of Experiment 2.
Figure 18A:
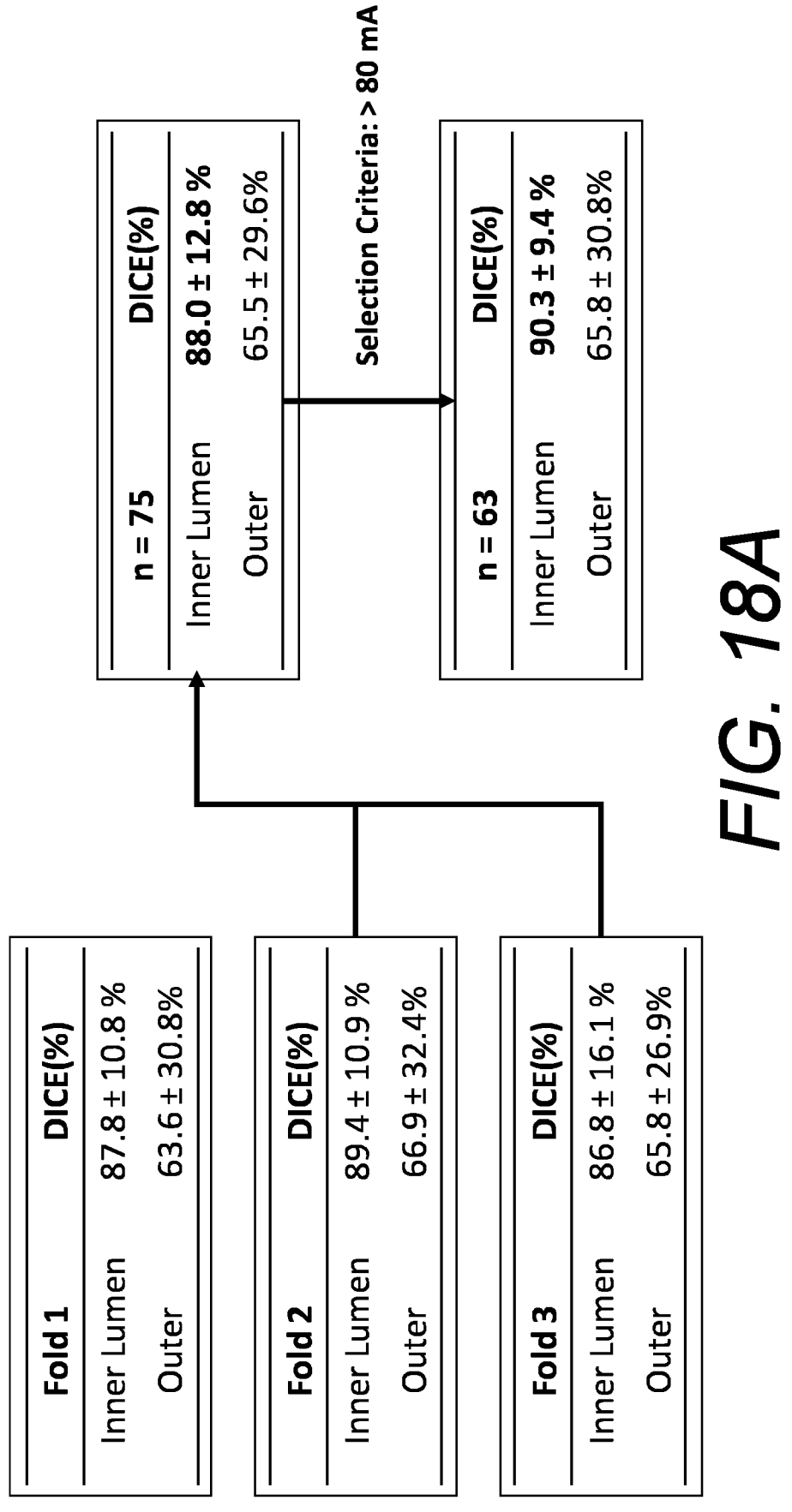
FIG. 18A shows tables summarising the results of Experiment 2.
Figure 18B:
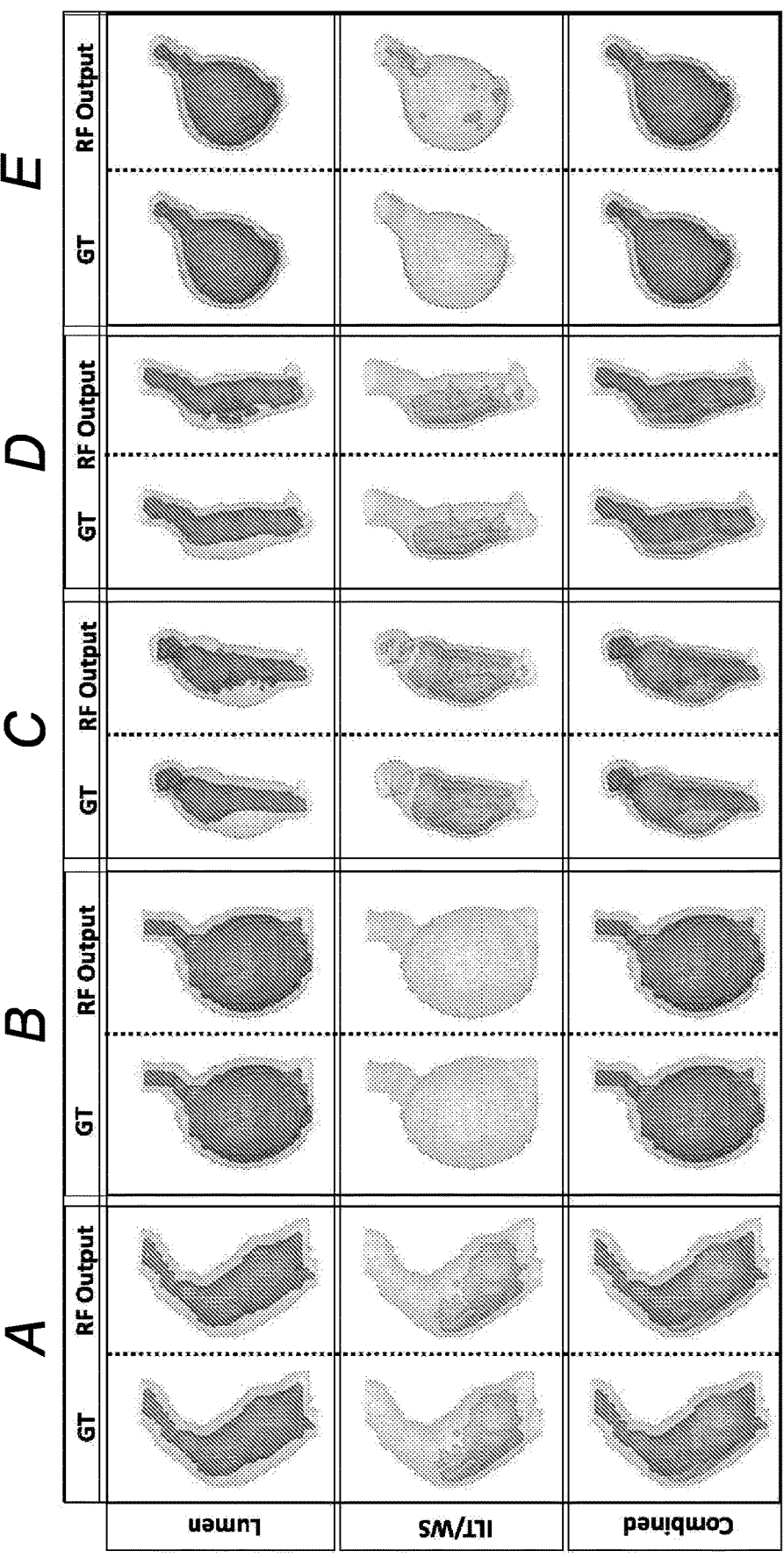
FIG. 18B shows a visualisation of the classification outputs of the second experiment (Experiment 2)

A 3-fold cross validation approach was employed to train and assess the random forest classifier. That is, the datasets for the same 75 patients were used three times with different randomly selected training/validation data and test data. The tables shown in FIGS. 17A, 17C, and 17E show the number of sub-volumes sampled in relation to the inner lumen and thrombus for the training/validation cohort which consisted of 50 patients (n=50) and the number of sub-volumes sampled in relation to the inner lumen and thrombus region for the testing cohort which consisted of a set of 25 (n=25) patients not presented during model training and validation. The table of FIG. 17A relates to Fold 1 and the corresponding ROC is shown in FIG. 17B. The table of FIG. 17C relates to Fold 2 and the corresponding ROC is shown in FIG. 17D. The table of FIG. 17E relates to Fold 3 and the corresponding ROC is shown in FIG. 17F. The results on the validation cohort suggest that this classification model is able to differentiate between the two regions. The results for this experiment were comparable to that of experiment 1. In addition, the random forest classification outputs were reconstructed into segmentation maps (FIG. 18B shows this for 5 patients A-E) and the DICE score metric (see FIG. 18A) was used to assess classification accuracy. This was used to investigate the classification accuracy at the thrombus-lumen interface. Patient-based evaluation classification outputs (Experiment 2) as assessed by DICE score was ~88.0% as shown in FIG. 18A. Excluding the images obtained with tube currents <80 mA increased the segmentation accuracy to ~90%. This suggests that low tube currents are associated with decreased CT image quality, and so by excluding those images obtained with such low tube currents one is better able to train the random forest classifier.

FIG. 18B shows the ground truth and the 3D reconstruction of the classification outputs, identifying the structural features within an aneurysmal region of NCT images obtained from 5 different patients (A-E). For each patient A-E, FIG. 18B shows the ground truth in relation to the inner lumen, the aneurysm wall structure, intra-luminal thrombus (ILT/WS), and a combination of the inner lumen and ILT in the first column and the outputs from a random forest classification algorithm of the inner lumen, the wall structure, intra-luminal thrombus (ILT/WS), and a combination of the inner lumen and ILT in the second column. The results provide support that the radiomic signatures of the lumen and thrombus can be used to differentiate visually indistinct regions on NCT images.

The above discussion illustrates that radiomic features can be used to train a random forest classification algorithm to identify structural features within an NCT image. FIG. 19 shows a flowchart of a method for training a random forest classification algorithm usable for identifying structural features of a blood vessel in an NCT image. The skilled person would appreciate that the method 1900 of FIG. 19 may be extended to any suitable classification algorithm.

At step 1910, the method comprises receiving a labelled training set. The labelled training set comprises information relating to a plurality of NCT images, where each NCT image of the plurality of NCT images shows a targeted region of a subject which includes at least one blood vessel. The training set further comprises a corresponding plurality of segmentation masks, where the segmentation masks are generated from a CCT image corresponding to an NCT image of the plurality of NCT images and each segmentation mask labels at least one structural feature of a blood vessel in a corresponding NCT image of the plurality of NCT images. The labelled training set may be similar to that described above in relation to the image segmentation model. The labelled training set may be generated by following the method described in relation to FIG. 5. In some examples, the labelled training set comprises NCT images taken with a tube current greater than a predetermined threshold current, for example 80 mA.

At step 1920, the method comprises dividing each NCT image and the corresponding segmentation mask into sub-volumes, where each sub-volume of the corresponding segmentation mask labels at least one feature in a corresponding sub-volume in a corresponding NCT image. In some examples, the sub-volumes have a volume of 10 mm×10 mm×10 mm. However, it will be appreciated that the sub-volumes may be greater or smaller than 10 mm×10 mm×10 mm.

At step 1930, the method comprises extracting, from each sub-volume of the NCT image, radiomic feature values for a set of radiomic features.

At step 1940, the method comprises training a random forest classification algorithm, using the extracted radiomic feature values for each sub-volume of each NCT image and the corresponding sub-volume of the corresponding segmentation masks, to learn features of the NCT images that correspond to structural features of the blood vessels labelled in the segmentation masks.

At step 1950, the method comprises output of a trained random forest classification model usable for identifying structural features of a blood vessel in an NCT image.

The method for training a random forest classification algorithm, as described above in relation to FIG. 19, is suitable for performance by a computing apparatus such as computing apparatus 600 as shown in FIG. 6. The method may be stored in machine/computer-readable form on a machine-readable/computer-readable medium, such as machine readable medium 3300 described in relation to FIG. 33. The trained random forest classification algorithm may be stored in machine/computer-readable form on a machine-readable/computer-readable medium, such as machine readable medium 3300 described in relation to FIG. 33.

FIG. 20 shows a flowchart 2000 of a method for identifying structural features of a blood vessel in a NCT image.

At step 2010, the method comprises sampling radiomic feature values for a set of radiomic features for each of a plurality of sub-volumes of a NCT image, wherein the NCT image shows a targeted region of a subject, the targeted region including at least one blood vessel.

At step 2020, the method comprises classifying the sub-volume as belonging to a structural feature of a set of structural features based on the sampled radiomic feature values. Classifying may be performed by a trained random forest classification algorithm such as that output by the process of FIG. 19. Alternatively, a random forest classification algorithm need not be used. One may, for example, compare radiomic feature values of the subvolumes against threshold radiomic feature values known to be indicative of a particular structural feature. Comparing radiomic feature values with corresponding thresholds may comprise checking for at least a 10-fold difference between the radiomic feature values and the threshold values. Comparing radiomic features with corresponding thresholds may comprise checking for at least a 20-fold difference between the radiomic features and the threshold values.

At step 2030, the method comprises identifying, from the classifications of the plurality of sub-volumes of the NCT image, structural features of a blood vessel shown in the targeted region.

The method for identifying structural features of a blood vessel in a NCT image, as described above in relation to FIG. 20, is suitable for performance by a computing apparatus such as computing apparatus 600 as shown in FIG. 6. The method may be stored in machine/computer-readable form on a machine-readable/computer-readable medium, such as machine readable medium 3300 described in relation to FIG. 33.

The discussion above has demonstrated that a trained machine learning image segmentation model can be used to identify structural features of blood vessels in a NCT image, and similarly a trained random forest classification algorithm can be used to identify structural features of blood vessels in a NCT image.

Generative adversarial networks (GANs) have also been investigated. GANS are an approach to generative modelling using deep learning methods, for example convolutional networks. GANS are a class of deep learning architectures whereby two networks train simultaneously, with one network focused on data generation (generator) and the other network focused on data discrimination (discriminator). The generator network and the discriminator network 'compete' against each other, learning the statistical distribution of the training data, which in turn enables the generator to generate new examples from the same distribution. A known dataset serves as the initial training data for the discriminator network. Training the discriminator involves presenting it with samples from the training dataset, until it achieves acceptable accuracy. The generator network trains based on whether it succeeds in fooling the discriminator.

The inventors have demonstrated that GANs can be used to generate/produce a pseudo-contrast computed tomography (PCT) image from an input non-contrast computed tomography (NCT) image.

A conditional GAN (CGAN) is an extension to the GAN idea. In a conditional GAN, the generative model can be trained to generate new examples from the input domain, where the random vector from the latent space is provided with/conditioned by some additional value, such as a class value, a digit or so on. The discriminator model is also trained by being provided with both an input image that is real or fake and the additional input.

A cycle-GAN is an extension to the GAN idea. Traditionally, training an image-to-image translation model requires a dataset comprising many paired examples of input images and corresponding expected output images. A cycle-GAN is an approach to training image-to-image translation using the GAN model architecture, in which the generator models and discriminator models can be trained without the need for paired examples in the training data. A cycle-GAN may comprise two generator networks and two discriminator networks. One generator may take images from the first domain as input and output images for the second domain, and the second generator may take images from the second domain and generate images for the first domain. A first discriminator may determine the plausibility of the output image from the first generator and the second discriminator may determine the plausibility of the output image from the second network. Additionally, the output images from the first generator may be input to the second generator and vice versa in order to encourage cycle consistency—if an original input image is input to the first generator and the generated output image is input to the second generator, then it is desirable that the output from the second generator substantially matches the original image. Accordingly, a cycle-GAN may be thought of as two inter-related CGANS each comprising a generator and a discriminator, whereby each CGAN is trained to synthesize an image given an input image. A loss function is further used to update each of the CGANs based on cycle consistency. Cycle consistency loss compares an image input to the cycle-GAN with the generated output and updates the generator models in each training iteration.

In a test, 75 patients for which paired NCT and CCT images were available were randomly selected from an approved clinical study. A 2-D cycle-GAN and a CGAN were trained and evaluated for the purposes of generating a pseudo-contrast computed tomography (PCT) image from an input NCT image, using a 3-fold cross-validation approach with a training/testing split of 50:25 patients (a total of 11,243 images) respectively. The accuracies of the generated outputs were assessed using four metrics of clinical importance (aneurysm diameter, area, lumen/thrombus volume, and thrombus morphology) against that obtained from CCT images (ground truth). It was found that the generated PCT images bear a strong concordance with the ground truth and enable the assessment of important clinical metrics.

Figure 21:
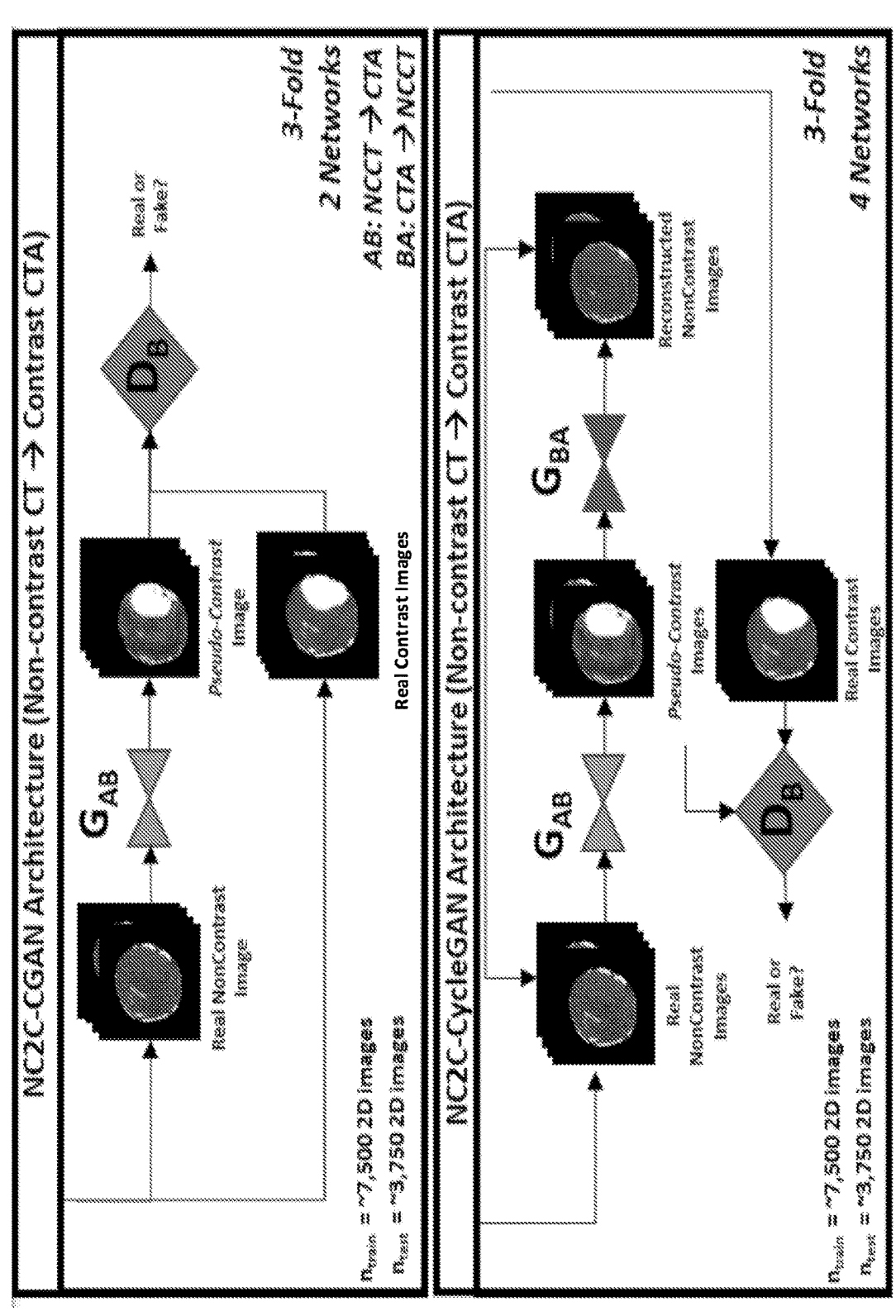
FIG. 21 illustrates a Conditional-GAN architecture and a Cycle-GAN architecture for generating pseudo-contrast computed tomography images based on an input NCT image.

FIG. 21 illustrates the two GAN architectures used. The upper box in FIG. 21 illustrates the CGAN architecture (labelled NC2C-CGAN Architecture in the figure) for generating a PCT image from an NCT image. The lower box in FIG. 21 illustrates the cycle-GAN architecture (labelled NC2C-CycleGAN Architecture in the figure) for generating a PCT image from an NCT image.

The Non-Contrast-to-Contrast-Cycle-GAN (NC2C-Cycle-GAN) architecture comprises of 4 networks, where 2 of the networks are generator networks ($G_{AB}$, and $G_{BA}$) and 2 discriminator networks (only one of which, $D_B$ is shown in the figure). The generator networks and discriminator networks comprised neural networks. The generator and discriminator components in the NC2C-Cycle-GAN model architecture were explicitly defined as least-squares GAN and a 70×70 PatchGAN, respectively. The NC2C-Cycle-GAN model incorporates an additional least-squares loss function for the discriminator, which in turn, improves the training of the generative model. On the other hand, the discriminator $D_B$ goes through the image pairs, in 70×70 patches, and is trained to classify whether the image under question is "real" or "fake".

The CGAN comprised a pixel to pixel CGAN (Pix2Pix-CGAN). Unlike the cycle-GAN, CGANs require paired non-contrast and contrast images. The generator ($G_{BA}$) and discriminator ($D_B$) components in the NC2C-Conditional GAN model (NC2C-CGAN) architecture were identical to those used in the NC2C-Cycle GAN (least-squares GAN and a 70×70 PatchGAN discriminator). Once again, the discriminator and the generator comprised neural networks.

A 3-fold cross-validation training paradigm with a training to testing data split of 50:25 patients (~7,500: ~3,750 2D axial slices) was employed for both deep learning architectures. Both deep learning GAN architectures were trained with a learning rate of $2.0\times10^{-5}$ for 200 epochs on 256×256 images centered around the aorta. For the NC2C-Cycle-GAN architecture, four networks (2 generators+2 discriminators) were trained simultaneously and various loss functions were evaluated at each iteration to document model training. In addition to the loss metrics inherent to the networks, both an identity mapping function and a cycle consistency loss function were included to ensure appropriate style transfer and regularization of the generator to allow for image translation, respectively. On the other hand, two networks (1 generator+1 discriminator) were trained for the NC2C-CGAN architecture. Model weights were saved every 10 epochs and intermediate model predictions were generated from the NCT images within the training cohort. The generated PCT images were independently evaluated against the ground truth to assess model training and generated image quality.

Each testing cohort contained a unique set of 25 patients. During model training, the root-mean-square error (RMSE) between the generated PCT image and its corresponding CTA image decreases with epoch duration to plateau at 8.0±1.2 and 8.5±1.4 for the CGAN and cycle-GAN respectively. Similarly, the $DICE_I$ coefficient (which quantifies the similarity of segmented regions) increases with epoch duration to plateau at 91.8±0.6% and 92±0.4% for the CGAN and cycle-GAN respectively. The latest model from each fold was used for subsequent analysis.

Figure 22:
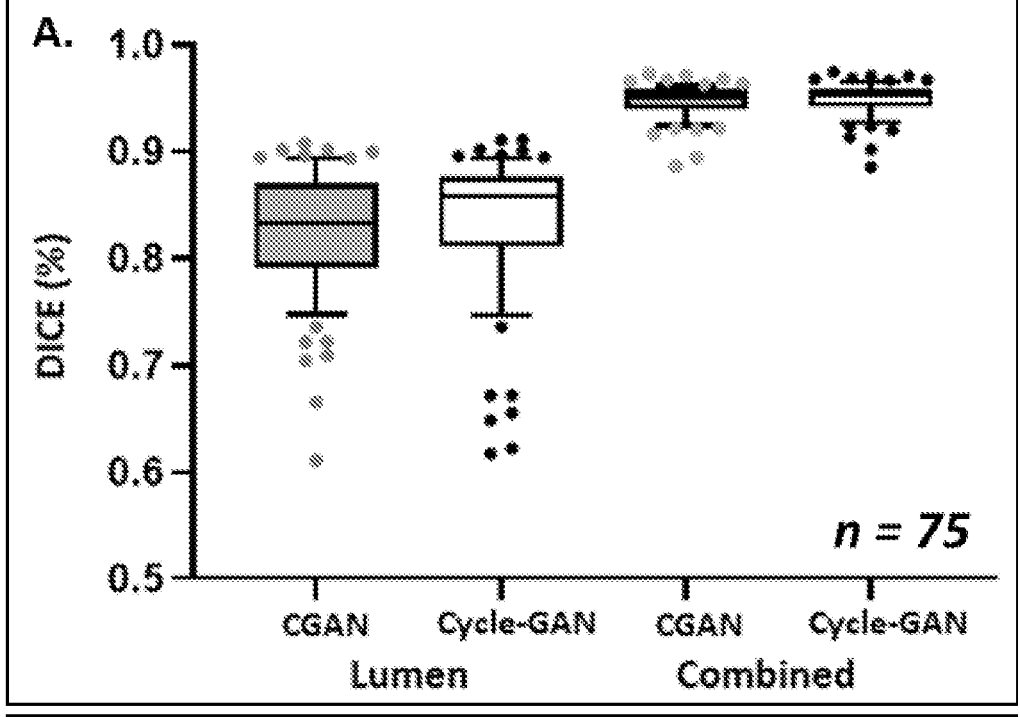
FIG. 22 shows Box Plots of Averaged DICE scores per patient within the testing cohort for the lumen ($DICE_I$) and the combined aortic mask ($DICE_C$) segmentations (box A), and further shows Root Mean Square Error (RMSE) and DICE scores of generated pseudo-contrast axal images (box B)

FIG. 22 indicates the RMSE and DICE scores for the 2D-axial pseudo-contrast images generated from the testing cohorts across the three folds using both GAN architectures (n=11,243 images, 75 patients). Both models displayed similar performances with regards to these metrics. A per-patient reconstruction accuracy was derived by grouping the 2D-axial images and their respective DICE scores by patient. Box plots of DICE scores for the inner lumen ($DICE_I$) and combined aortic region ($DICE_C$) as derived by the deep learning models are displayed. The whiskers of the plot represent the $10^{th}$ and $90^{th}$ percentile. With regards to $DICE_I$, the median performance of the cycle-GAN is greater than that of the CGAN. Of note, there is multiple overlap between the outliers below the $10^{th}$ percentile of cycle-GAN and CGAN (6/7) networks. This suggests that there may be image properties inherent to this subgroup of patients leading to decreased transformation accuracy.

Figures 23A, 23B:
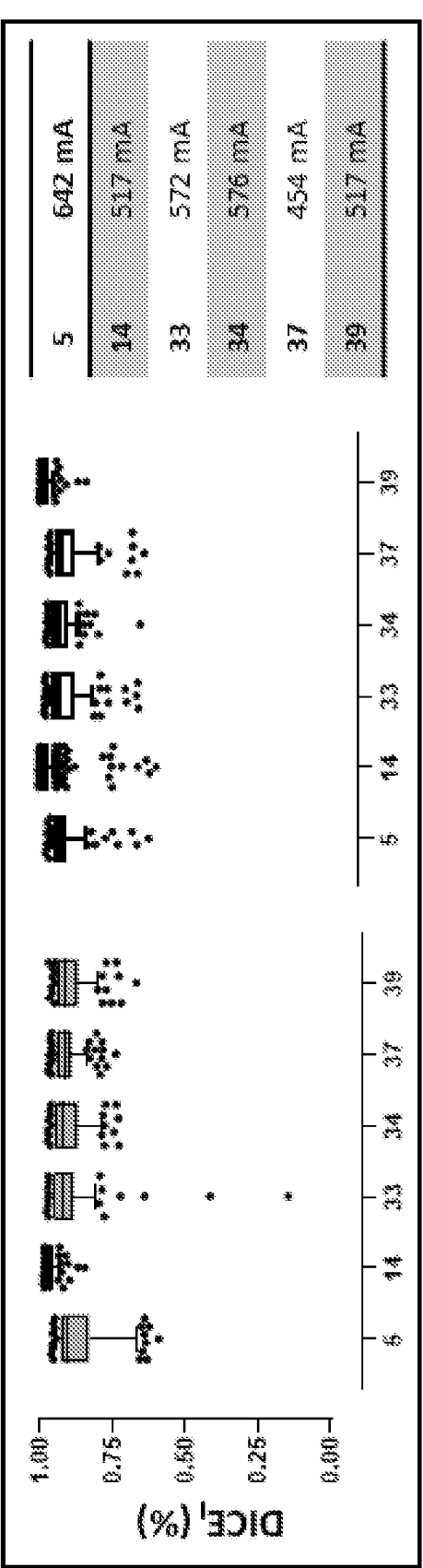
FIGS. 23A and 23B show increased DICE score variability in NCT images obtained with low X-Ray tube currents (mA)—patients (n=6) with the lowest reconstruction accuracy (FIG. 23A) are compared against those (n=6) with the highest reconstruction accuracy (FIG. 23B), and X-ray tube currents for the NCT images are shown accordingly.
Figure 24:
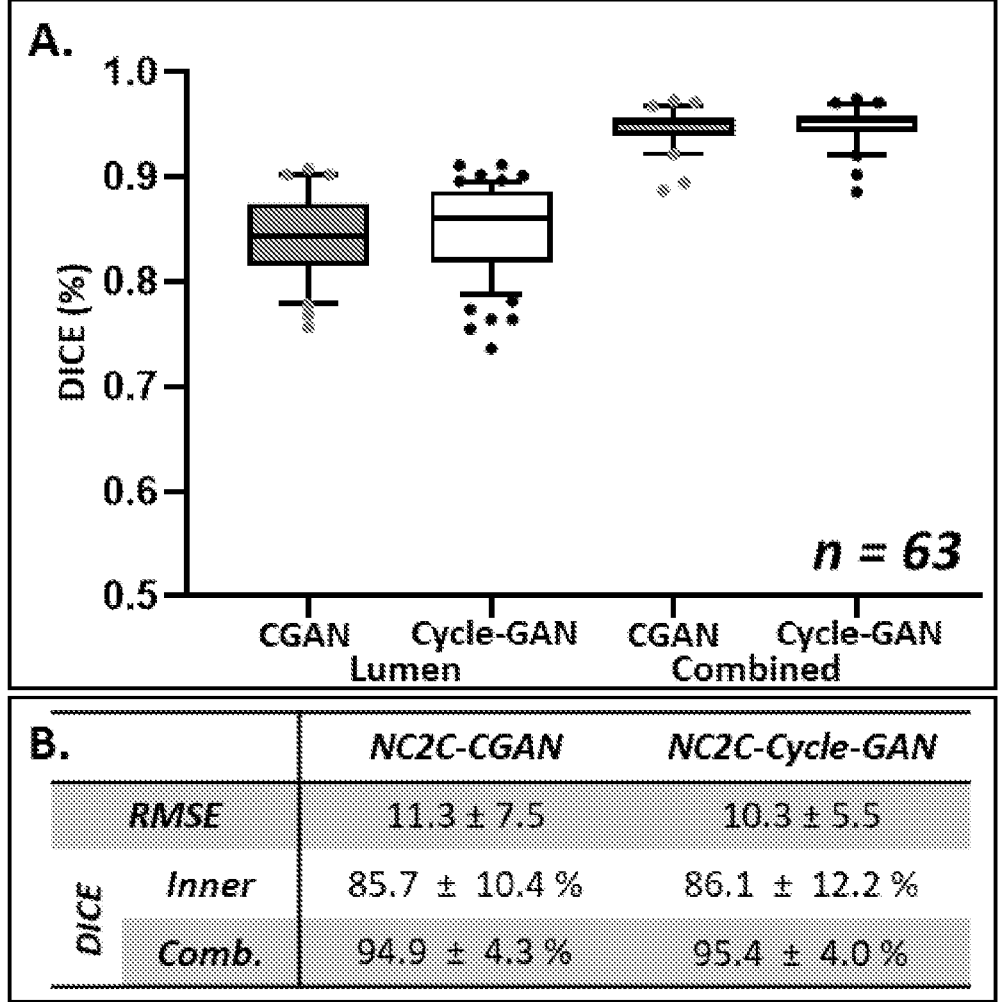
FIG. 24 shows Box Plots of averaged DICE scores per patient within a refined cohort (tube current >80 mA, n=63) for the lumen ($DICE_I$) and the combined aortic mask ($DICE_C$) segmentations, and further shows overall RMSE and DICE scores of pseudo-contrast images from NCT images obtained at >80 mA.

Comparison of the image properties of the NCT scans below the $10^{th}$ percentile and above the $90^{th}$ percentile mark highlighted one prominent difference with regards to the x-ray tube current used during image acquisition. Scans obtained with lower tube current values tended to produce images with poorer transformation accuracy. FIG. 23A highlights six of these patients with highly variable inner lumen reconstructions as denoted by a large spread of axial $DICE_I$ scores. These scans were obtained with an average tube current of 73.3±3.67 mA. FIG. 23B shows six patients within the testing cohort with the best inner lumen reconstructions. Correspondingly, these images were obtained using an average tube current of 546.3±64.7 mA. Based on this finding, the tube current for all images within the testing cohort was subsequently extracted. At this point, a stringent threshold criteria of utilizing NCT images above the $15^{th}$ percentile was utilized to exclude potential outliers. This equated to a selection criterion of images obtained with tube current >80 mA. Exclusion of these 12 images, resulted in a decrease in RMSE, and a corresponding increase in $DICE_I$ for both generative models (FIG. 24). $DICE_C$ scores remained unaffected by this exclusion.

Figure 25:
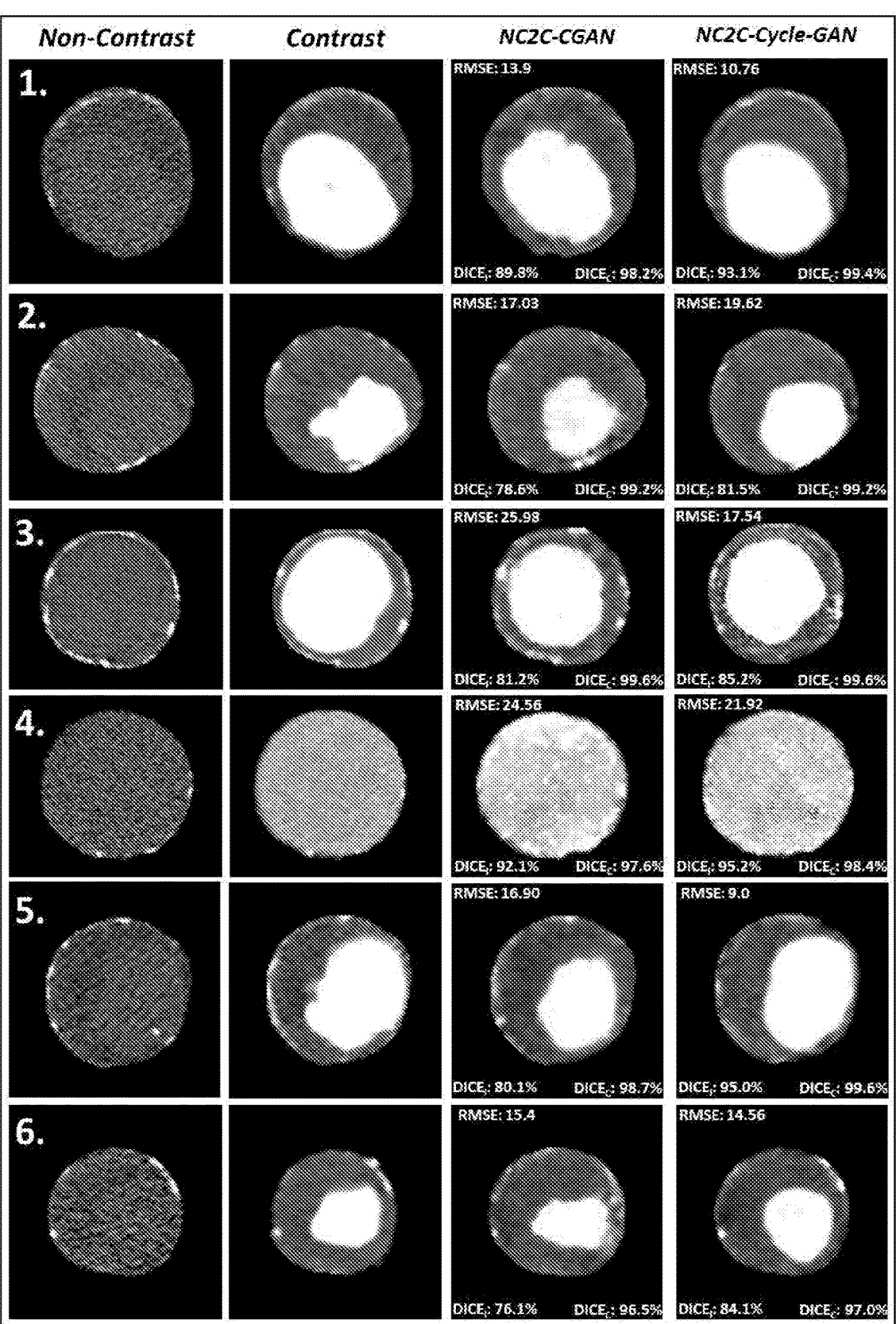
FIG. 25 shows sample NCT, CCT and PCT images for 6 patients, the PCT images generated using a trained Conditional-GAN and a trained Cycle-GAN.

FIG. 25 highlights six CCT and NCT axial slices alongside their generated PCT images which were generated using the NC2C-GAN and the NC2C-Cycle-GAN. These slices were obtained from 6 different patients (1-6) within the testing cohort. For each patient (1-6), FIG. 25 shows the NCT image, the CCT image, the NC2C-CGAN generated PCT image, and the NC2C-Cycle-GAN generated PCT image. The generated PCT images for each patient also show two DICE scores ($DICE_I$ and $DICE_C$) which quantify the similarity of segmented regions to the ground truth. The $DICE_I$ score corresponds to the score for the inner lumen, whereas the $DICE_C$ score corresponds to the combined aortic region. The lumen region generated from the NC2C-Cycle-GAN for each patient bears close resemblance to the ground truth image as compared to that generated by the NC2C-C-GAN. This is also reflected by the superior $DICE_I$ scores. On the other hand, $DICE_C$ scores were identical for both sets of model predictions.

Figure 26:
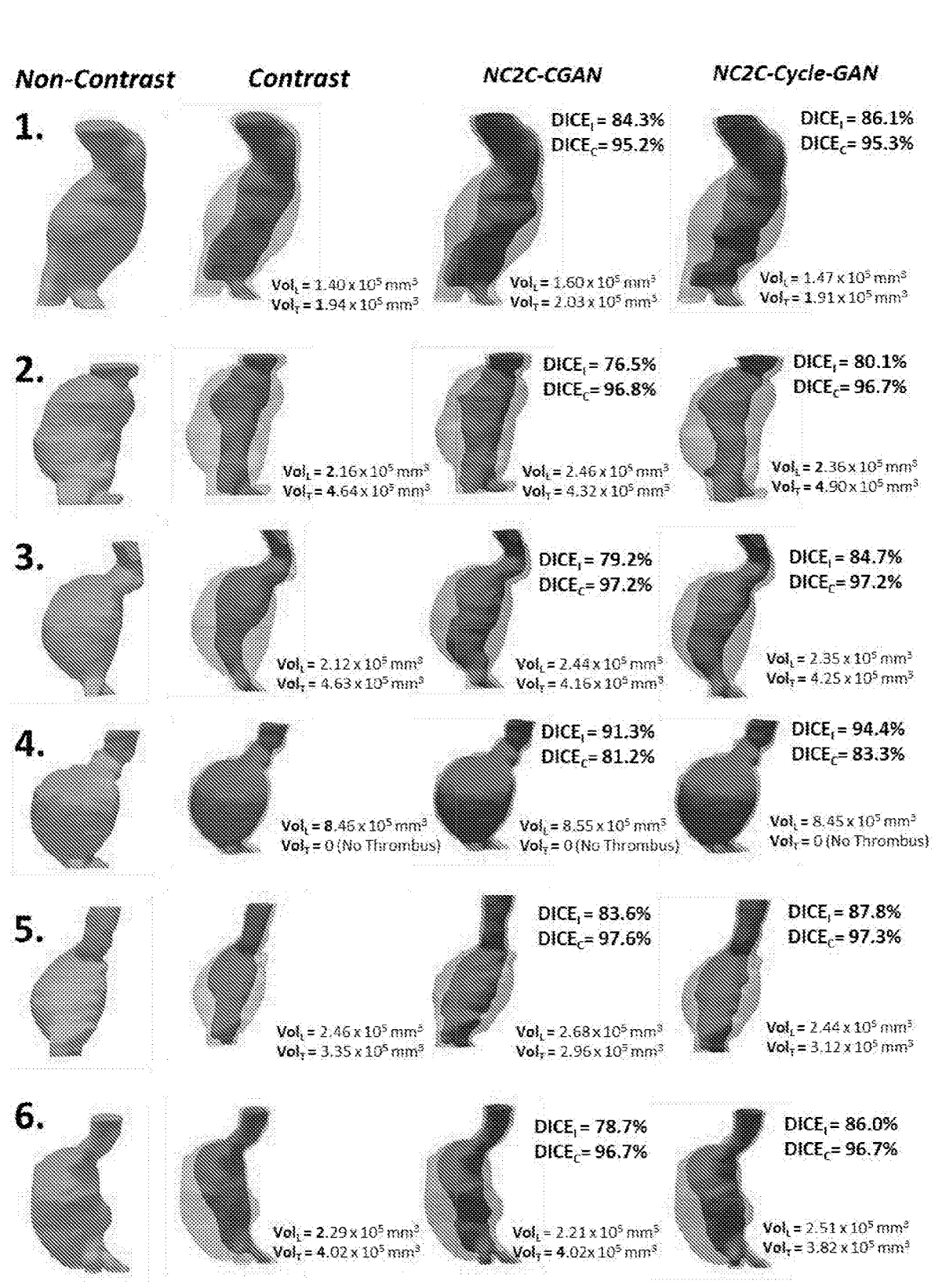
FIG. 26 shows volume reconstructions from PCT images including those of FIG. 25.

From the generated 2D-axial slices, the 3D volumes of these 6 patients were reconstructed. The aneurysmal regions for each of these patients are illustrated in FIG. 26.

Evaluation of aneurysm morphology was performed using 4 metrics including diameter, area and volume measurements as well as overall ILT spatial morphology. This information is useful in defining the biological behaviour of an AAA during the natural history of the disease. Measurements derived from the two GAN models' outputs were compared against those obtained from GT segmentations. The NC2C-Cycle-GAN model was better at approximating the maximum lumen diameter per axial slice when compared with that of the NC2C-CGAN model (panel A of FIG. 27). The bias is closer to zero [95% CI of −17.5:11.0 mm]. On the other hand, both models have similar biases in determining the outer vessel wall diameter (Panel B of FIG. 27). Maximum inner lumen and outer vessel wall diameters extracted from the model outputs are strongly correlated against GT measurements (NC2C-CGAN, ρ=0.83 and 0.98; NC2C-Cycle-GAN, ρ=0.85 and 0.99, p<0.01; where ρ is the Spearman coefficient).

Figure 27:
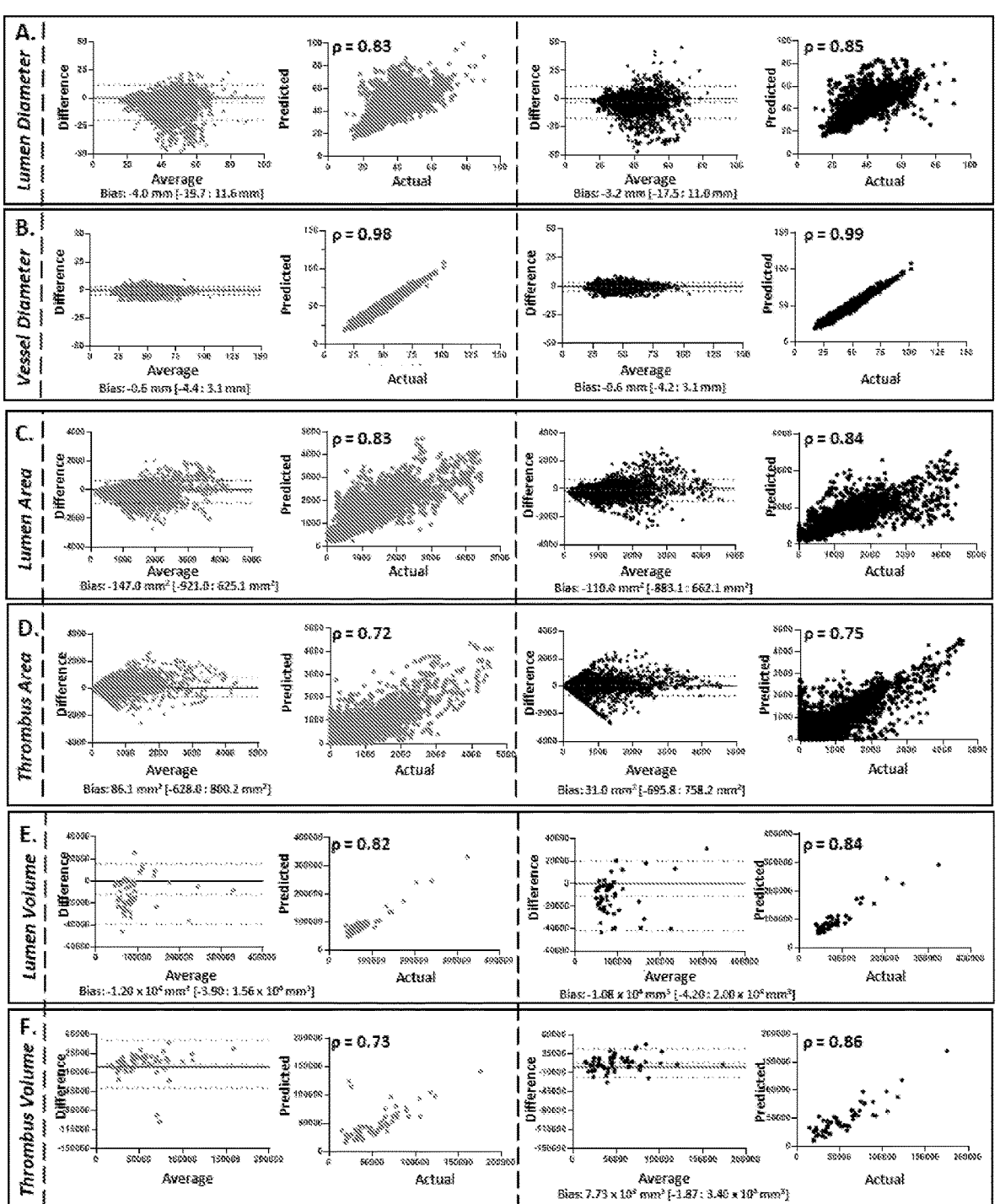
FIG. 27 shows several Bland-Altman plots and correlation-coefficient analyses comparing the measurements of generated images compared against those derived from ground truth segmentations—Spearman coefficients ($\rho$) are indicated on the graphs and p<0.01 for all comparisons.

For both 2-D measurements, the NC2C-Cycle-GAN model had a lower bias and a narrower CI range when compared to that of the NC2C-CGAN model (panels C and D of FIG. 27). Thrombus area in each axial slice as determined by the NC2C-CGAN and NC2C-Cycle-GAN models is on average 9.4±12.2% and 9.3±11.5% different from GT measurements of thrombus area. Additionally, the NC2C-Cycle-GAN was able to better approximate the 3D-lumen and thrombus volume measurements when compared with that of the NC2C-CGAN (panels E and F of FIG. 27). Thrombus volumes derived from the CGAN show a strong correlation with GT measurements (p=0.73, p<0.01). Lumen volumes derived from both models (NC2C-CGAN: ρ=0.82, NC2C-Cycle-GAN: ρ=0.84, p<0.01) and thrombus volumes (ρ=0.86, p<0.01) from the NC2C-Cycle-GAN are very strongly correlated with the manually derived measurements.

Figures 28A, 28B:
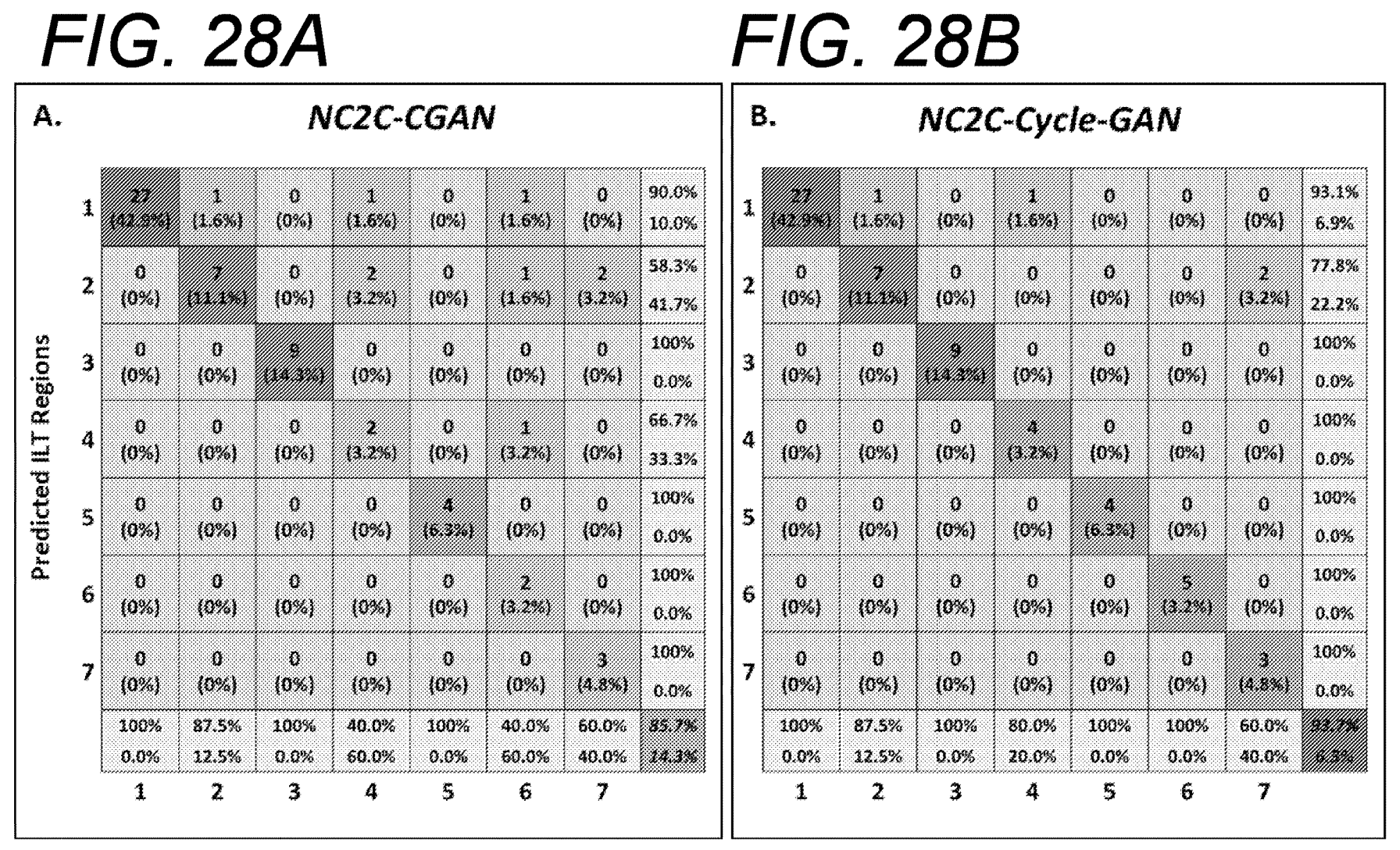

Classification of ILT morphology within the aneurysmal sac was assessed by first isolating the aneurysmal region in the generative model outputs and the GT segmentations. Overall, this was documented by compiling the axial regional ILT classifications and identifying the predominant classification type. Pseudo-contrast images within the aneurysmal region produced by NC2C-Cycle-GAN (FIG. 28A) had an ILT classification accuracy of 93.5%, which outperformed that produced by the generative images of the NC2C-CGAN model (85.7%, FIG. 28B).

Figure 29:
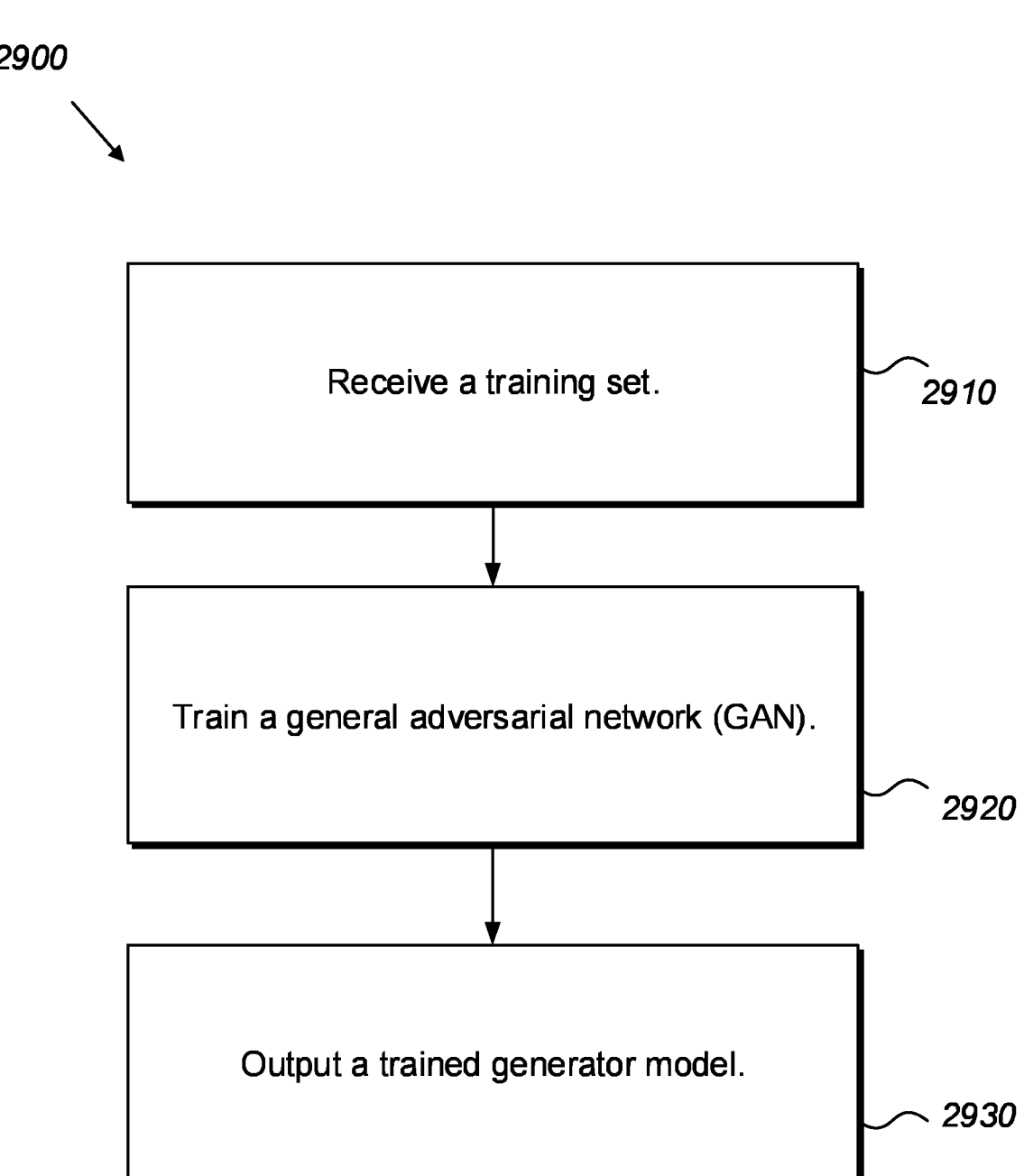
FIG. 29 shows a flowchart.

FIG. 29 shows a flowchart of a method for training a general adversarial network (GAN) to generate a pseudo-contrast computed tomography (PCT) image from a non-contrast computed tomography (NCT) image. The GAN comprises a generator network and a discriminator network.

At step 2910, the method comprises receiving a training set, where the training set comprises: a plurality of NCT images, each NCT image of the plurality of NCT images showing at least one blood vessel, and a plurality of contrast computed tomography (CCT) images, each CCT image showing at least one blood vessel.

At step 2920, the method comprises training the GAN by training the generator network and the discriminator network, where training the generator network comprises using the plurality of NCT images and feedback from the discriminator network, to generate PCT images and training the discriminator network comprises using the generated PCT images and the plurality of CCT images, to classify received images as PCT images or CCT images and to provide feedback to the generator network.

At step 2930, the method comprises outputting a trained generator model to translate an input NCT image to a PCT image showing at least one blood vessel.

The method for training a GAN as described above in relation to FIG. 29, is suitable for performance by a computing apparatus such as computing apparatus 600 as shown in FIG. 6. Instructions for implementing the method may be stored in computer-readable form on a machine-readable medium such as machine-readable storage medium 3300.

FIG. 30 shows a flowchart of a method identifying structural features of a blood vessel in a non-contrast computed tomography (NCT) image.

At step 3010, the method comprises providing the NCT image to a trained generator model, the trained generator model trained as part of a generative adversarial network, as described above in relation to FIG. 26, where the generator model is trained to translate an input NCT image to a pseudo-contrast PCT image showing at least one blood vessel.

At step 3020, the method comprises generating, using the trained generator model, a PCT image corresponding to the provided NCT image.

At step 3030, the method comprises identifying, from the PCT image, structural features of the at least one blood vessel.

The method for identifying structural features of a blood vessel in a NCT image, as described above in relation to FIG. 30, is suitable for performance by a computing apparatus such as computing apparatus 600 as shown in FIG. 6. Instructions for implementing the method may be stored in computer-readable form on a machine-readable medium such as machine-readable storage medium 3300.

FIG. 31 shows a flowchart of a method for obtaining labelled structural features for an unlabelled NCT image.

At step 3110, the method comprises sending an unlabelled NCT image to a server, where the NCT image comprises a targeted region of a subject including at least one blood vessel. The server may contain instructions for identifying structural features of a blood vessel in an unlabelled NCT image.

At step 3120, the method comprises receiving, from the server, information indicative of a predicted segmentation mask for the NCT image, where the predicted segmentation mask labels structural features of the at least one blood vessel of the targeted region.

The method for obtaining structural features for an unlabelled NCT image, as described above in relation to FIG. 31, is suitable for performance by a computing apparatus such as computing apparatus 600 as shown in FIG. 6. Instructions for implementing the method may be stored in computer-readable form on a machine-readable medium such as machine-readable storage medium 3300.

Figure 32:
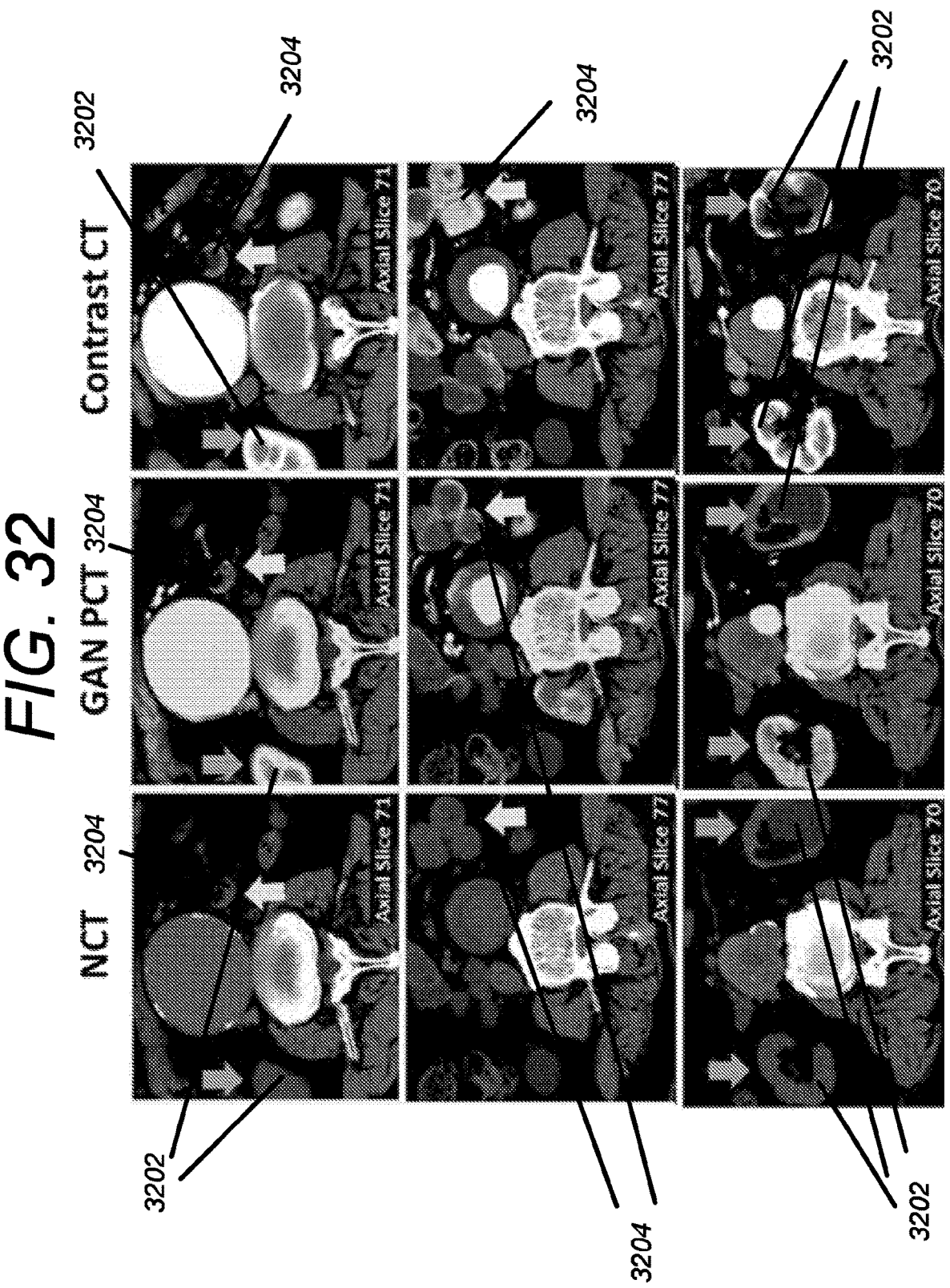
FIG. 32 shows three NCT images and corresponding CCT images and PCT images as generated by a GAN.

The methods described above in relation to FIGS. 29-31 may be applied to other anatomical structures, for example organs. FIG. 32 shows the results of a GAN used to identify a kidney. In FIG. 32, the left hand column shows three NCT image slices, the middle column shows three GAN generated PCT images based on the corresponding NCT images, and the right hand column shows three equivalent CCT images (the "ground truth"). In each image, the kidney(s) 3202 (blue arrows) and bowel 3204 (yellow arrows) are labelled. In the top row, a kidney and bowel are visible in all three images. In the middle row, only the bowel is visible. In the bottom row, the two kidneys are visible in all three images. In the GAN-generated PCT images, the images of the kidneys and bowel are enhanced when compared to their respective NCT images.

Figure 33:
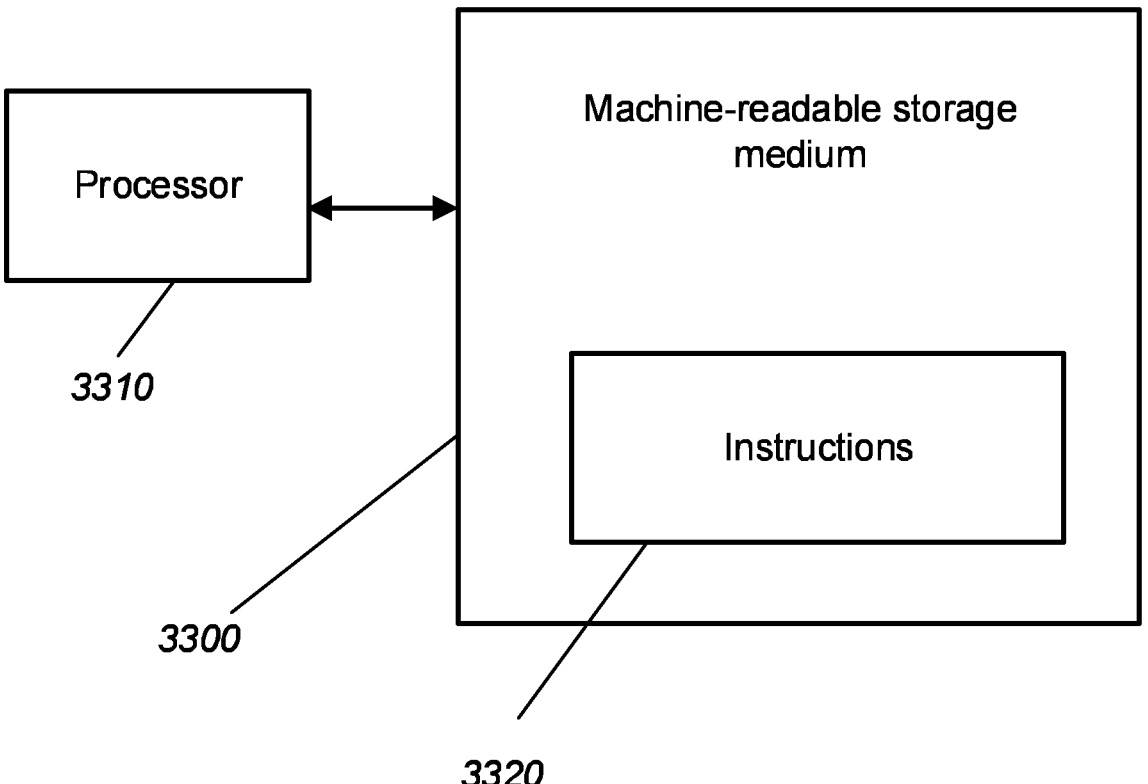
FIG. 33 is a block diagram of a machine-readable medium according to some examples.

FIG. 33 illustrates a computer readable medium 3300 according to some examples. The computer readable medium 3300 stores units, with each unit including instructions 3320 that, when executed, cause a processor 3310 or other processing/computing device or apparatus to perform particular operations.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine-readable storage storing such a program. Still further, embodiments of the present invention may be conveyed electronically via any medium such as a communication signal carried over a wired or wireless connection and embodiments suitably encompass the same.

Many variations of the methods described herein will be apparent to the skilled person. For example, the methods described herein can be used to identify/segment features in other blood vessels besides the aorta (e.g. other arteries or veins). Furthermore, the methods described herein can be used to analyse the behaviour of other organs, for example in the liver, bowel, spleen, or kidney.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method for training a generative adversarial network (GAN) to generate a pseudo-contrast computed tomography (PCT) image from a non-contrast computed tomography (NCT) image, the GAN comprising a generator network and a discriminator network, the method comprising:

receiving a training set comprising:

a plurality of NCT images, each NCT image of the plurality of NCT images showing at least one anatomical structure; and a plurality of contrast computed tomography (CCT) images, each CCT image showing at least one anatomical structure;

training the GAN, wherein training the GAN comprises:

training the generator network, using the plurality of NCT images and feedback from the discriminator network, to generate PCT images;

training the discriminator network, using the generated PCT images and the plurality of CCT images, to classify received images as PCT images or CCT images and to provide feedback to the generator network; and outputting a trained generator model to translate an input NCT image to a PCT image showing at least one anatomical structure.

2. The method according to claim 1, wherein the GAN is a conditional GAN.

3. The method according to claim 1, wherein the GAN is a cycle-GAN.

4. The method according to claim 1, wherein the generator network comprises a U-NET architecture.

5. The method according to claim 1, wherein the anatomical structure comprises a blood vessel.

6. The method according to claim 1, wherein the anatomical structure comprises a bowel.

7. A computer-readable medium having instructions stored thereon which, when executed by one or more processors, cause the one or more processors to implement a method for training a generative adversarial network (GAN) according to claim 1.

8. A method for identifying anatomical structures in a non-contrast computed tomography (NCT) image, the method comprising:

providing the NCT image to a trained generator model, the trained generator model as part of a generative adversarial network, the generator model trained to translate an input NCT image to a pseudo-contrast computed tomography (PCT) image showing at least one anatomical structure; and generating, using the trained generator model, a PCT image corresponding to the provided NCT image; and identifying, from the PCT image, structural features of the at least one anatomical structure.

9. The method of claim 1, wherein the discriminator network comprises a neural network or a random forest.

10. The computer-readable medium according to claim 7, further having stored thereon instructions which when executed by one or more processors, cause the one or more processors to implement the steps of:

providing an input NCT image to the trained generator model, the trained generator model as part of the generative adversarial network (GAN), the generator model trained to translate the input NCT image to a pseudo-contrast computed tomography (PCT) image showing at least one anatomical structure; and generating, using the trained generator model, a PCT image corresponding to the provided NCT image; and identifying, from the PCT image, structural features of the at least one anatomical structure.

11. A computing apparatus for identifying anatomical structures in a non-contrast computed tomography (NCT) image, the apparatus comprising:

one or more memory units; and one or more processors configured to execute instructions stored in the one or more memory units to perform the method of claim 1.

12. The method of claim 1, wherein the anatomical structure comprises an organ.

13. The method of claim 12, wherein the organ is an abdominal organ, a chest organ, or a pelvic organ.

14. The method of claim 12, wherein the organ is a kidney, liver, spleen, pancreas, prostate, small intestine, large intestine, stomach, gall bladder, oesophagus, heart, or lung.

15. The method of claim 1, wherein the anatomical structure comprises a muscle, adipose tissue, or both.

\* \* \* \* \*